(12) United States Patent
Finlay

(10) Patent No.: US 10,858,435 B2
(45) Date of Patent: Dec. 8, 2020

(54) PD1 BINDING AGENTS

(71) Applicant: ULTRAHUMAN NINE LIMITED, Sandwich (GB)

(72) Inventor: William James Jonathan Finlay, Sandwich (GB)

(73) Assignee: ULTRAHUMAN NINE LIMITED, Sandwich (GB)

(*) Notice: Subject to any disclaimer, the term of this patent is extended or adjusted under 35 U.S.C. 154(b) by 0 days.

(21) Appl. No.: 16/912,023

(22) Filed: Jun. 25, 2020

(65) Prior Publication Data

US 2020/0332006 A1 Oct. 22, 2020

Related U.S. Application Data

(63) Continuation of application No. PCT/EP2019/055927, filed on Mar. 8, 2019.

(30) Foreign Application Priority Data

Mar. 8, 2018 (GB) .................................. 1803746.5
Aug. 16, 2018 (GB) .................................. 1813405.6

(51) Int. Cl.
*C07K 16/28* (2006.01)

(52) U.S. Cl.
CPC ...... *C07K 16/2818* (2013.01); *C07K 2317/24* (2013.01); *C07K 2317/33* (2013.01); *C07K 2317/52* (2013.01); *C07K 2317/55* (2013.01); *C07K 2317/565* (2013.01); *C07K 2317/76* (2013.01); *C07K 2317/94* (2013.01)

(58) Field of Classification Search
None
See application file for complete search history.

(56) References Cited

U.S. PATENT DOCUMENTS 8,735,553 B1 5/2014 Li et al.

FOREIGN PATENT DOCUMENTS

| EP | 3 081 576 A1 | 10/2016 |
|---|---|---|
| WO | WO 2006/121168 A1 | 11/2006 |
| WO | WO 2017/055404 A1 | 4/2017 |
| WO | WO 2019/170885 A1 | 9/2019 |

OTHER PUBLICATIONS

International Search Report and Written Opinion dated Jun. 7, 2019 for International Application No. PCT/EP2019/055901, 14 pages.
International Search Report and Written Opinion dated Jun. 11, 2019 for International Application No. PCT/EP2019/055927, 14 pages.
Finlay, W. J. J. et al., "Anti-PD1 'SHR-1210' aberrantly targets proangiogenic receptors and this polyspecificity can be ablated by paratope refinement," mAbs, 11(1):26-44 (2019).
Townsend, S. et al., "Augmented Binary Substitution: Single-pass CDR germlining and stabilization of therapeutic antibodies," PNAS, 112(50):15354-15359 (2015).

*Primary Examiner* — Amy E Juedes
*Assistant Examiner* — Brian Hartnett
(74) *Attorney, Agent, or Firm* — Cooley LLP; Ivor Elrifi

(57) ABSTRACT

Provided herein are antibody molecules that bind specifically to Programmed cell death 1 (PD1) and related nucleic acid molecules, vectors and host cells. Also provided herein are medical uses of such antibody molecules.

20 Claims, 17 Drawing Sheets
Specification includes a Sequence Listing.

SEQUENCE LISTING

<160> NUMBER OF SEQ ID NOS: 416

<210> SEQ ID NO 1
<211> LENGTH: 118
<212> TYPE: PRT
<213> ORGANISM: Artificial Sequence
<220> FEATURE:
<223> OTHER INFORMATION: Antibody MH8 heavy chain variable (VH) region

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Asn Ile Trp Gln Asp Gly Ser Thr Lys Tyr Val Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Ala Tyr Gly Asn Tyr Trp Tyr Ile Asp Arg Trp Gly Gln Gly Thr
            100                 105                 110

Thr Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Antibody MH8 light chain variable (VL) region

<400> SEQUENCE: 2

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Asn Asp
            20                  25                  30

Val Ala Trp Tyr Gln Gln Lys Pro Gly Gln Pro Pro Lys Leu Leu Ile
        35                  40                  45

Asn Tyr Ala Tyr His Arg Phe Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Thr Pro Tyr
                85                  90                  95

Thr Phe Gly Gln Gly Thr Lys Leu Glu Ile Lys
            100                 105

<210> SEQ ID NO 3
<211> LENGTH: 118
<212> TYPE: PRT
<213> ORGANISM: Artificial Sequence
<220> FEATURE:
<223> OTHER INFORMATION: Antibody MH4 heavy chain variable (VH) region

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Met Ser Trp Val Arg Gln Ala Pro Gly Lys Gly Leu Glu Trp Val
        35                  40                  45

Ala Val Ile Trp Gln Asp Gly Ser Thr Asn Tyr Val Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Ala Tyr Gly Asn Tyr Trp Tyr Ile Asp Arg Trp Gly Gln Gly Thr
            100                 105                 110

Thr Val Thr Val Ser Ser
        115
```

<210> SEQ ID NO 4
<211> LENGTH: 107
<212> TYPE: PRT
<213> ORGANISM: Artificial Sequence
<220> FEATURE:
<223> OTHER INFORMATION: Antibody MH4 light chain variable (VL) region

<400> SEQUENCE: 4

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Asn Asp
            20                  25                  30

Val Ala Trp Tyr Gln Gln Lys Pro Gly Gln Pro Pro Lys Leu Leu Ile
        35                  40                  45

Asn Tyr Ala Tyr His Arg Phe Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Thr Pro Tyr
                85                  90                  95

Thr Phe Gly Gln Gly Thr Lys Leu Glu Ile Lys
            100                 105
```

<210> SEQ ID NO 5
<211> LENGTH: 118
<212> TYPE: PRT
<213> ORGANISM: Artificial Sequence
<220> FEATURE:
<223> OTHER INFORMATION: Antibody MH12 heavy chain variable (VH) region

<400> SEQUENCE: 5

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Asn Ile Trp Gln Asp Gly Ser Glu Lys Tyr Val Asp Ser Val Lys
50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Ala Tyr Gly Asn Tyr Trp Tyr Ile Asp Arg Trp Gly Gln Gly Thr
            100                 105                 110

Thr Val Thr Val Ser Ser
        115

<210> SEQ ID NO 6
<211> LENGTH: 107
<212> TYPE: PRT
<213> ORGANISM: Artificial Sequence
<220> FEATURE:
<223> OTHER INFORMATION: Antibody MH12 light chain variable (VL) region

<400> SEQUENCE: 6

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Asn Asp
            20                  25                  30

Val Ala Trp Tyr Gln Gln Lys Pro Gly Gln Pro Pro Lys Leu Leu Ile
        35                  40                  45

Asn Tyr Ala Tyr His Arg Phe Thr Gly Val Pro Asp Arg Phe Ser Gly
50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Thr Pro Tyr
                85                  90                  95

Thr Phe Gly Gln Gly Thr Lys Leu Glu Ile Lys
            100                 105

<210> SEQ ID NO 7
<211> LENGTH: 118
<212> TYPE: PRT
<213> ORGANISM: Artificial Sequence
<220> FEATURE:
<223> OTHER INFORMATION: Antibody 09C06 heavy chain variable (VH) region

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Trp Val
        35                  40                  45

Ala Asn Ile Trp Gln Asp Gly Ser Thr Asn Tyr Val Asp Ser Val Lys
50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95
```

```
Arg Ala Tyr Gly Asn Tyr Trp Tyr Ile Asp Arg Trp Gly Gln Gly Thr
            100                 105                 110

Thr Val Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: Antibody 09C06 light chain variable (VL) region

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Ser Asn Asp
            20                  25                  30

Val Ala Trp Tyr Gln Gln Lys Pro Gly Gln Pro Pro Lys Leu Leu Ile
        35                  40                  45

Asn Tyr Ala Ser His Arg Phe Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Thr Pro Tyr
                85                  90                  95

Thr Phe Gly Gln Gly Thr Lys Leu Glu Ile Lys
            100                 105

<210> SEQ ID NO 9
<211> LENGTH: 327
<212> TYPE: PRT
<213> ORGANISM: Homo sapiens

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 10
<211> LENGTH: 327
<212> TYPE: PRT
<213> ORGANISM: Homo sapiens

<400> SEQUENCE: 10

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220
```

```
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 11
<211> LENGTH: 330
<212> TYPE: PRT
<213> ORGANISM: Homo sapiens

<400> SEQUENCE: 11

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
```

```
              260                 265                 270
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 12
<211> LENGTH: 330
<212> TYPE: PRT
<213> ORGANISM: Homo sapiens

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
            290                 295                 300
```

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 13
<211> LENGTH: 326
<212> TYPE: PRT
<213> ORGANISM: Homo sapiens

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 14

<211> LENGTH: 330
<212> TYPE: PRT
<213> ORGANISM: Homo sapiens

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 15
<211> LENGTH: 329
<212> TYPE: PRT
<213> ORGANISM: Homo sapiens

<400> SEQUENCE: 15

Ala Ser Thr Lys Gly Pro Ser Val Phe Pro Leu Ala Pro Ser Ser Lys
1               5                   10                  15

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 16
<211> LENGTH: 288
<212> TYPE: PRT
<213> ORGANISM: Homo sapiens

<400> SEQUENCE: 16

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
```

```
                 50                  55                  60
Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
                115                 120                 125

Ala Pro Lys Ala Gln Ile Lys Glu Ser Leu Arg Ala Glu Leu Arg Val
                130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
                210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285

<210> SEQ ID NO 17
<211> LENGTH: 288
<212> TYPE: PRT
<213> ORGANISM: Macaca fascicularis

<400> SEQUENCE: 17

Met Gln Ile Pro Gln Ala Pro Trp Pro Val Val Trp Ala Val Leu Gln
 1                   5                  10                  15

Leu Gly Trp Arg Pro Gly Trp Phe Leu Glu Ser Pro Asp Arg Pro Trp
                 20                  25                  30

Asn Ala Pro Thr Phe Ser Pro Ala Leu Leu Leu Val Thr Glu Gly Asp
                 35                  40                  45

Asn Ala Thr Phe Thr Cys Ser Phe Ser Asn Ala Ser Glu Ser Phe Val
                 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Arg Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
                115                 120                 125

Ala Pro Lys Ala Gln Ile Lys Glu Ser Leu Arg Ala Glu Leu Arg Val
                130                 135                 140
```

```
Thr Glu Arg Arg Ala Glu Val Pro Thr Ala His Pro Ser Pro Ser Pro
145                 150                 155                 160

Arg Pro Ala Gly Gln Phe Gln Ala Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Gln Gly Thr Ile Glu Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Ala Pro
225                 230                 235                 240

Cys Val Pro Glu Gln Thr Glu Tyr Ala Thr Ile Val Phe Pro Ser Gly
                245                 250                 255

Leu Gly Thr Ser Ser Pro Ala Arg Arg Gly Ser Ala Asp Gly Pro Arg
            260                 265                 270

Ser Pro Arg Pro Leu Arg Pro Glu Asp Gly His Cys Ser Trp Pro Leu
        275                 280                 285
```

```
<210> SEQ ID NO 18
<211> LENGTH: 5
<212> TYPE: PRT
<213> ORGANISM: Homo sapiens

<400> SEQUENCE: 18

Arg Asp Glu Leu Thr
1               5

<210> SEQ ID NO 19
<211> LENGTH: 4
<212> TYPE: PRT
<213> ORGANISM: Homo sapiens

<400> SEQUENCE: 19

Arg Glu Glu Met
1

<210> SEQ ID NO 20
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1
<220> FEATURE:
<221> NAME/KEY: misc_feature
<222> LOCATION: (3)..(3)
<223> OTHER INFORMATION: Xaa is Thr or a conservative substitution of
      Thr
<220> FEATURE:
<221> NAME/KEY: misc_feature
<222> LOCATION: (4)..(4)
<223> OTHER INFORMATION: Xaa is Phe or a conservative substitution of
      Phe
<220> FEATURE:
<221> NAME/KEY: misc_feature
<222> LOCATION: (5)..(5)
<223> OTHER INFORMATION: Xaa is Ser or a conservative substitution of
      Ser
<220> FEATURE:
<221> NAME/KEY: misc_feature
<222> LOCATION: (8)..(8)
<223> OTHER INFORMATION: Xaa is Gly or any other amino acid
<220> FEATURE:
<221> NAME/KEY: misc_feature
<222> LOCATION: (9)..(9)
```

<223> OTHER INFORMATION: Xaa is Met or a conservative substitution of
      Met
<220> FEATURE:
<221> NAME/KEY: misc_feature
<222> LOCATION: (10)..(10)
<223> OTHER INFORMATION: Xaa is Ser or any other amino acid

<400> SEQUENCE: 20

Gly Phe Xaa Xaa Xaa Ser Tyr Xaa Xaa Xaa
1               5                   10

<210> SEQ ID NO 21
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2
<220> FEATURE:
<221> NAME/KEY: misc_feature
<222> LOCATION: (1)..(1)
<223> OTHER INFORMATION: Xaa is Val or a conservative substitution of
      Val
<220> FEATURE:
<221> NAME/KEY: misc_feature
<222> LOCATION: (2)..(2)
<223> OTHER INFORMATION: Xaa is Ala or a conservative substitution of
      Ala
<220> FEATURE:
<221> NAME/KEY: misc_feature
<222> LOCATION: (3)..(3)
<223> OTHER INFORMATION: Xaa is Val or Asn
<220> FEATURE:
<221> NAME/KEY: misc_feature
<222> LOCATION: (5)..(5)
<223> OTHER INFORMATION: Xaa is Trp or Lys
<220> FEATURE:
<221> NAME/KEY: misc_feature
<222> LOCATION: (6)..(6)
<223> OTHER INFORMATION: Xaa is Gln or Ala
<220> FEATURE:
<221> NAME/KEY: misc_feature
<222> LOCATION: (7)..(7)
<223> OTHER INFORMATION: Xaa is Asp or Gly
<220> FEATURE:
<221> NAME/KEY: misc_feature
<222> LOCATION: (10)..(10)
<223> OTHER INFORMATION: Xaa is Thr or Glu
<220> FEATURE:
<221> NAME/KEY: misc_feature
<222> LOCATION: (11)..(11)
<223> OTHER INFORMATION: Xaa is Asn, Lys, or Ser
<220> FEATURE:
<221> NAME/KEY: misc_feature
<222> LOCATION: (13)..(13)
<223> OTHER INFORMATION: Xaa is Asn or Val

<400> SEQUENCE: 21

Xaa Xaa Xaa Ile Xaa Xaa Xaa Gly Ser Xaa Xaa Tyr Xaa Asp Ser Val
1               5                   10                  15

Lys Gly

<210> SEQ ID NO 22
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3
<220> FEATURE:
<221> NAME/KEY: misc_feature
<222> LOCATION: (1)..(1)
<223> OTHER INFORMATION: Xaa is Ala or any other amino acid
<220> FEATURE:

```
<221> NAME/KEY: misc_feature
<222> LOCATION: (2)..(2)
<223> OTHER INFORMATION: Xaa is Tyr or a conservative substitution of
      Tyr
<220> FEATURE:
<221> NAME/KEY: misc_feature
<222> LOCATION: (4)..(4)
<223> OTHER INFORMATION: Xaa is Asn or any other amino acid
<220> FEATURE:
<221> NAME/KEY: misc_feature
<222> LOCATION: (5)..(5)
<223> OTHER INFORMATION: Xaa is Tyr or a conservative substitution of
      Tyr
<220> FEATURE:
<221> NAME/KEY: misc_feature
<222> LOCATION: (6)..(6)
<223> OTHER INFORMATION: Xaa is Trp or any other amino acid
<220> FEATURE:
<221> NAME/KEY: misc_feature
<222> LOCATION: (8)..(8)
<223> OTHER INFORMATION: Xaa is Ile or any other amino acid
<220> FEATURE:
<221> NAME/KEY: misc_feature
<222> LOCATION: (9)..(9)
<223> OTHER INFORMATION: Xaa is Asp or a conservative substitution of
      Asp
<220> FEATURE:
<221> NAME/KEY: misc_feature
<222> LOCATION: (10)..(10)
<223> OTHER INFORMATION: Xaa is Val or any other amino acid

<400> SEQUENCE: 22

Xaa Xaa Gly Xaa Xaa Xaa Tyr Xaa Xaa Xaa
1               5                   10

<210> SEQ ID NO 23
<211> LENGTH: 10
<212> TYPE: PRT
<213> ORGANISM: Mus musculus

<400> SEQUENCE: 23

Gly Phe Ser Leu Thr Ser Tyr Gly Val His
1               5                   10

<210> SEQ ID NO 24
<211> LENGTH: 16
<212> TYPE: PRT
<213> ORGANISM: Mus musculus

<400> SEQUENCE: 24

Val Ile Trp Ala Gly Gly Ser Thr Asn Tyr Asn Ser Ala Leu Met Ser
1               5                   10                  15

<210> SEQ ID NO 25
<211> LENGTH: 10
<212> TYPE: PRT
<213> ORGANISM: Mus musculus

<400> SEQUENCE: 25

Ala Tyr Gly Asn Tyr Trp Tyr Ile Asp Val
1               5                   10

<210> SEQ ID NO 26
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      portion LCDR1
<220> FEATURE:
<221> NAME/KEY: misc_feature
```

```
<222> LOCATION: (4)..(4)
<223> OTHER INFORMATION: Xaa is Gln or Glu
<220> FEATURE:
<221> NAME/KEY: misc_feature
<222> LOCATION: (7)..(7)
<223> OTHER INFORMATION: Xaa is Ser or a conservative substitution of
      Ser
<220> FEATURE:
<221> NAME/KEY: misc_feature
<222> LOCATION: (10)..(10)
<223> OTHER INFORMATION: Xaa is Leu or a conservative substitution of
      Leu

<400> SEQUENCE: 26

Lys Ser Ser Xaa Ser Val Xaa Asn Asp Xaa Ala
1               5                   10

<210> SEQ ID NO 27
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      portion LCDR2
<220> FEATURE:
<221> NAME/KEY: misc_feature
<222> LOCATION: (3)..(3)
<223> OTHER INFORMATION: Xaa is Phe or any other amino acid
<220> FEATURE:
<221> NAME/KEY: misc_feature
<222> LOCATION: (4)..(4)
<223> OTHER INFORMATION: Xaa is His or any other amino acid
<220> FEATURE:
<221> NAME/KEY: misc_feature
<222> LOCATION: (7)..(7)
<223> OTHER INFORMATION: Xaa is Ser or a conservative substitution of
      Ser

<400> SEQUENCE: 27

Tyr Ala Xaa Xaa Arg Phe Xaa
1               5

<210> SEQ ID NO 28
<211> LENGTH: 9
<212> TYPE: PRT
<213> ORGANISM: Artificial Sequence
<220> FEATURE:
<223> OTHER INFORMATION: anti-PD1 antibody molecule or antigen-binding
      portion LCDR3
<220> FEATURE:
<221> NAME/KEY: misc_feature
<222> LOCATION: (1)..(1)
<223> OTHER INFORMATION: Xaa is Gln or any other amino acid
<220> FEATURE:
<221> NAME/KEY: misc_feature
<222> LOCATION: (3)..(3)
<223> OTHER INFORMATION: Xaa is Ala or any other amino acid
<220> FEATURE:
<221> NAME/KEY: misc_feature
<222> LOCATION: (6)..(6)
<223> OTHER INFORMATION: Xaa is Thr or any other amino acid
<220> FEATURE:
<221> NAME/KEY: misc_feature
<222> LOCATION: (8)..(8)
<223> OTHER INFORMATION: Xaa is Tyr or any other amino acid

<400> SEQUENCE: 28

Xaa Gln Xaa Tyr Ser Xaa Pro Xaa Thr
1               5

<210> SEQ ID NO 29
<211> LENGTH: 11
<212> TYPE: PRT
```

```
<213> ORGANISM: Mus musculus

<400> SEQUENCE: 29

Lys Ala Ser Gln Ser Val Ser Asn Asp Val Ala
1               5                   10

<210> SEQ ID NO 30
<211> LENGTH: 11
<212> TYPE: PRT
<213> ORGANISM: Mus musculus

<400> SEQUENCE: 30

Lys Ser Ser Gln Glu Val Ser Asn Asp Val Ala
1               5                   10

<210> SEQ ID NO 31
<211> LENGTH: 7
<212> TYPE: PRT
<213> ORGANISM: Mus musculus

<400> SEQUENCE: 31

Tyr Ala Phe His Arg Phe Thr
1               5

<210> SEQ ID NO 32
<211> LENGTH: 9
<212> TYPE: PRT
<213> ORGANISM: Mus musculus

<400> SEQUENCE: 32

His Gln Ala Tyr Ser Ser Pro Tyr Thr
1               5

<210> SEQ ID NO 33
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 33

Gly Phe Thr Phe Ser Ser Tyr Gly Met Ser
1               5                   10

<210> SEQ ID NO 34
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 34

Val Ala Asn Ile Trp Gln Asp Gly Ser Thr Lys Tyr Val Asp Ser Val
1               5                   10                  15

Lys Gly

<210> SEQ ID NO 35
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3
```

```
<400> SEQUENCE: 35

Ala Tyr Gly Asn Tyr Trp Tyr Ile Asp Arg
1               5                   10

<210> SEQ ID NO 36
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      portion LCDR1

<400> SEQUENCE: 36

Lys Ser Ser Gln Ser Val Thr Asn Asp Val Ala
1               5                   10

<210> SEQ ID NO 37
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      portion LCDR2

<400> SEQUENCE: 37

Tyr Ala Tyr His Arg Phe Thr
1               5

<210> SEQ ID NO 38
<211> LENGTH: 9
<212> TYPE: PRT
<213> ORGANISM: Artificial Sequence
<220> FEATURE:
<223> OTHER INFORMATION: anti-PD1 antibody molecule or antigen-binding
      portion LCDR3

<400> SEQUENCE: 38

His Gln Ala Tyr Ser Ser Pro Tyr Thr
1               5

<210> SEQ ID NO 39
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 39

Gly Phe Ser Leu Ser Ser Tyr Gly Met Ser
1               5                   10

<210> SEQ ID NO 40
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 40

Val Ala Val Ile Trp Gln Asp Gly Ser Thr Asn Tyr Val Asp Ser Val
1               5                   10                  15

Lys Gly

<210> SEQ ID NO 41
```

```
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 41

Val Ala Asn Ile Trp Gln Asp Gly Ser Glu Lys Tyr Val Asp Ser Val
1               5                   10                  15

Lys Gly

<210> SEQ ID NO 42
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 42

Gly Phe Ser Phe Ser Ser Tyr Gly Met His
1               5                   10

<210> SEQ ID NO 43
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 43

Val Ala Asn Ile Trp Gln Asp Gly Ser Thr Asn Tyr Val Asp Ser Val
1               5                   10                  15

Lys Gly

<210> SEQ ID NO 44
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      portion LCDR1

<400> SEQUENCE: 44

Lys Ser Ser Gln Ser Val Ser Asn Asp Val Ala
1               5                   10

<210> SEQ ID NO 45
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      portion LCDR2

<400> SEQUENCE: 45

Tyr Ala Ser His Arg Phe Thr
1               5

<210> SEQ ID NO 46
<211> LENGTH: 9
<212> TYPE: PRT
<213> ORGANISM: Artificial Sequence
<220> FEATURE:
<223> OTHER INFORMATION: anti-PD1 antibody molecule or antigen-binding
``` portion LCDR3

<400> SEQUENCE: 46

His Gln Ala Tyr Ser Thr Pro Tyr Thr
1               5

<210> SEQ ID NO 47
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 47

Gly Phe Ser Phe Thr Ser Tyr Gly Met Ser
1               5                   10

<210> SEQ ID NO 48
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 48

Leu Ala Asn Ile Trp Gln Asp Gly Ser Thr Asn Tyr Val Asp Ser Val
1               5                   10                  15

Lys Gly

<210> SEQ ID NO 49
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 49

Gly Phe Thr Phe Ser Ser Tyr Gly Val His
1               5                   10

<210> SEQ ID NO 50
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 50

Val Gly Val Ile Trp Gln Asp Gly Ser Glu Asn Tyr Val Asp Ser Val
1               5                   10                  15

Lys Gly

<210> SEQ ID NO 51
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      portion LCDR1

<400> SEQUENCE: 51

Lys Ser Ser Gln Ser Val Ser Asn Asp Leu Ala

<210> SEQ ID NO 52
<211> LENGTH: 9
<212> TYPE: PRT
<213> ORGANISM: Artificial Sequence
<220> FEATURE:
<223> OTHER INFORMATION: anti-PD1 antibody molecule or antigen-binding
      portion LCDR3

<400> SEQUENCE: 52

Gln Gln Ala Tyr Ser Thr Pro Tyr Thr
1               5

<210> SEQ ID NO 53
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 53

Leu Ala Asn Ile Trp Gln Asp Gly Ser Glu Asn Tyr Val Asp Ser Val
1               5                   10                  15

Lys Gly

<210> SEQ ID NO 54
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 54

Gly Phe Thr Leu Ser Ser Tyr Gly Met His
1               5                   10

<210> SEQ ID NO 55
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 55

Leu Ala Val Ile Trp Ala Asp Gly Ser Thr Asn Tyr Val Asp Ser Val
1               5                   10                  15

Lys Gly

<210> SEQ ID NO 56
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 56

Ala Tyr Gly Asn Tyr Met Tyr Ile Asp Val
1               5                   10

<210> SEQ ID NO 57
<211> LENGTH: 10

```
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 57

Gly Phe Thr Phe Ser Ser Tyr Gly Met His
1               5                   10

<210> SEQ ID NO 58
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 58

Val Gly Val Ile Lys Gln Asp Gly Ser Glu Asn Tyr Val Asp Ser Val
1               5                   10                  15

Lys Gly

<210> SEQ ID NO 59
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 59

Gly Phe Ser Phe Thr Ser Tyr Gly Met His
1               5                   10

<210> SEQ ID NO 60
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 60

Val Gly Val Ile Trp Gln Asp Gly Ser Thr Asn Tyr Val Asp Ser Val
1               5                   10                  15

Lys Gly

<210> SEQ ID NO 61
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 61

Gly Tyr Gly Asn Tyr Trp Tyr Ile Asp Val
1               5                   10

<210> SEQ ID NO 62
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1
```

```
<220> FEATURE:
<221> NAME/KEY: misc_feature
<222> LOCATION: (9)..(9)
<223> OTHER INFORMATION: Xaa is Met or Val
<220> FEATURE:
<221> NAME/KEY: misc_feature
<222> LOCATION: (10)..(10)
<223> OTHER INFORMATION: Xaa is Ser or His

<400> SEQUENCE: 62

Gly Phe Thr Phe Ser Ser Tyr Gly Xaa Xaa
1               5                   10

<210> SEQ ID NO 63
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2
<220> FEATURE:
<221> NAME/KEY: misc_feature
<222> LOCATION: (3)..(3)
<223> OTHER INFORMATION: Xaa is Val or Asn
<220> FEATURE:
<221> NAME/KEY: misc_feature
<222> LOCATION: (5)..(5)
<223> OTHER INFORMATION: Xaa is Trp or Lys
<220> FEATURE:
<221> NAME/KEY: misc_feature
<222> LOCATION: (10)..(10)
<223> OTHER INFORMATION: Xaa is Glu or Thr
<220> FEATURE:
<221> NAME/KEY: misc_feature
<222> LOCATION: (11)..(11)
<223> OTHER INFORMATION: Xaa is Asn or Lys
<220> FEATURE:
<221> NAME/KEY: misc_feature
<222> LOCATION: (13)..(13)
<223> OTHER INFORMATION: Xaa is Val or Asn

<400> SEQUENCE: 63

Val Ala Xaa Ile Xaa Gln Asp Gly Ser Xaa Xaa Tyr Xaa Asp Ser Val
1               5                   10                  15

Lys Gly

<210> SEQ ID NO 64
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3
<220> FEATURE:
<221> NAME/KEY: misc_feature
<222> LOCATION: (1)..(1)
<223> OTHER INFORMATION: Xaa is Ala, Asp, Glu, Gly, His, Ile, Lys, Leu,
      Gln, Ser, Val or Trp
<220> FEATURE:
<221> NAME/KEY: misc_feature
<222> LOCATION: (2)..(2)
<223> OTHER INFORMATION: Xaa is Tyr, Phe or Trp
<220> FEATURE:
<221> NAME/KEY: misc_feature
<222> LOCATION: (4)..(4)
<223> OTHER INFORMATION: Xaa is Asn, Ala, Glu, Phe, Gly, His, Ile, Gln,
      Arg, Ser, Thr, Val, Trp or Tyr
<220> FEATURE:
<221> NAME/KEY: misc_feature
<222> LOCATION: (5)..(5)
<223> OTHER INFORMATION: Xaa is Tyr, Val or Trp
<220> FEATURE:
<221> NAME/KEY: misc_feature
<222> LOCATION: (6)..(6)
```

```
<223> OTHER INFORMATION: Xaa is Trp, Phe, His, Met, Pro, Gln, Ser or Val
<220> FEATURE:
<221> NAME/KEY: misc_feature
<222> LOCATION: (8)..(8)
<223> OTHER INFORMATION: Xaa is Ile, Leu, Met, Ser, Thr, Val or Tyr
<220> FEATURE:
<221> NAME/KEY: misc_feature
<222> LOCATION: (9)..(9)
<223> OTHER INFORMATION: Xaa is Asp or Glu
<220> FEATURE:
<221> NAME/KEY: misc_feature
<222> LOCATION: (10)..(10)
<223> OTHER INFORMATION: Xaa is Val, Ala, Glu, Phe, Gly, His, Ile, Gln,
      Arg, Ser, Thr, Trp or Tyr

<400> SEQUENCE: 64

Xaa Xaa Gly Xaa Xaa Xaa Tyr Xaa Xaa Xaa
1               5                   10

<210> SEQ ID NO 65
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1
<220> FEATURE:
<221> NAME/KEY: misc_feature
<222> LOCATION: (10)..(10)
<223> OTHER INFORMATION: Xaa is Ser or His

<400> SEQUENCE: 65

Gly Phe Thr Phe Ser Ser Tyr Gly Met Xaa
1               5                   10

<210> SEQ ID NO 66
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2
<220> FEATURE:
<221> NAME/KEY: misc_feature
<222> LOCATION: (3)..(3)
<223> OTHER INFORMATION: Xaa is Val or Asn
<220> FEATURE:
<221> NAME/KEY: misc_feature
<222> LOCATION: (10)..(10)
<223> OTHER INFORMATION: Xaa is Glu or Thr
<220> FEATURE:
<221> NAME/KEY: misc_feature
<222> LOCATION: (11)..(11)
<223> OTHER INFORMATION: Xaa is Asn or Lys

<400> SEQUENCE: 66

Val Ala Xaa Ile Trp Gln Asp Gly Ser Xaa Xaa Tyr Val Asp Ser Val
1               5                   10                  15

Lys Gly

<210> SEQ ID NO 67
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3
<220> FEATURE:
<221> NAME/KEY: misc_feature
<222> LOCATION: (1)..(1)
<223> OTHER INFORMATION: Xaa is Ala or Gly
<220> FEATURE:
```

```
<221> NAME/KEY: misc_feature
<222> LOCATION: (6)..(6)
<223> OTHER INFORMATION: Xaa is Trp or Met
<220> FEATURE:
<221> NAME/KEY: misc_feature
<222> LOCATION: (10)..(10)
<223> OTHER INFORMATION: Xaa is Arg or Val

<400> SEQUENCE: 67

Xaa Tyr Gly Asn Tyr Xaa Tyr Ile Asp Xaa
1               5                   10

<210> SEQ ID NO 68
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      portion LCDR1
<220> FEATURE:
<221> NAME/KEY: misc_feature
<222> LOCATION: (4)..(4)
<223> OTHER INFORMATION: Xaa is Gln or Glu
<220> FEATURE:
<221> NAME/KEY: misc_feature
<222> LOCATION: (7)..(7)
<223> OTHER INFORMATION: Xaa is Ser, Gly or Thr
<220> FEATURE:
<221> NAME/KEY: misc_feature
<222> LOCATION: (10)..(10)
<223> OTHER INFORMATION: Xaa is Leu or Val

<400> SEQUENCE: 68

Lys Ser Ser Xaa Ser Val Xaa Asn Asp Xaa Ala
1               5                   10

<210> SEQ ID NO 69
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      portion LCDR2
<220> FEATURE:
<221> NAME/KEY: misc_feature
<222> LOCATION: (3)..(3)
<223> OTHER INFORMATION: Xaa is Phe, Ser or Tyr
<220> FEATURE:
<221> NAME/KEY: misc_feature
<222> LOCATION: (4)..(4)
<223> OTHER INFORMATION: Xaa is His, Pro or Thr
<220> FEATURE:
<221> NAME/KEY: misc_feature
<222> LOCATION: (7)..(7)
<223> OTHER INFORMATION: Xaa is Ser or Thr

<400> SEQUENCE: 69

Tyr Ala Xaa Xaa Arg Phe Xaa
1               5

<210> SEQ ID NO 70
<211> LENGTH: 9
<212> TYPE: PRT
<213> ORGANISM: Artificial Sequence
<220> FEATURE:
<223> OTHER INFORMATION: anti-PD1 antibody molecule or antigen-binding
      portion LCDR3
<220> FEATURE:
<221> NAME/KEY: misc_feature
<222> LOCATION: (1)..(1)
<223> OTHER INFORMATION: Xaa is Gln or His
<220> FEATURE:
<221> NAME/KEY: misc_feature
```

```
<222> LOCATION: (3)..(3)
<223> OTHER INFORMATION: Xaa is Ala or Ser
<220> FEATURE:
<221> NAME/KEY: misc_feature
<222> LOCATION: (6)..(6)
<223> OTHER INFORMATION: Xaa is Thr, Asn or Ser

<400> SEQUENCE: 70

Xaa Gln Xaa Tyr Ser Xaa Pro Tyr Thr
1               5

<210> SEQ ID NO 71
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      portion LCDR1
<220> FEATURE:
<221> NAME/KEY: misc_feature
<222> LOCATION: (7)..(7)
<223> OTHER INFORMATION: Xaa is Ser, Gly or Thr
<220> FEATURE:
<221> NAME/KEY: misc_feature
<222> LOCATION: (10)..(10)
<223> OTHER INFORMATION: Xaa is Leu or Val

<400> SEQUENCE: 71

Lys Ser Ser Gln Ser Val Xaa Asn Asp Xaa Ala
1               5                   10

<210> SEQ ID NO 72
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      portion LCDR2
<220> FEATURE:
<221> NAME/KEY: misc_feature
<222> LOCATION: (3)..(3)
<223> OTHER INFORMATION: Xaa is Ser or Tyr
<220> FEATURE:
<221> NAME/KEY: misc_feature
<222> LOCATION: (7)..(7)
<223> OTHER INFORMATION: Xaa is Ser or Thr

<400> SEQUENCE: 72

Tyr Ala Xaa His Arg Phe Xaa
1               5

<210> SEQ ID NO 73
<211> LENGTH: 9
<212> TYPE: PRT
<213> ORGANISM: Artificial Sequence
<220> FEATURE:
<223> OTHER INFORMATION: anti-PD1 antibody molecule or antigen-binding
      portion LCDR3
<220> FEATURE:
<221> NAME/KEY: misc_feature
<222> LOCATION: (1)..(1)
<223> OTHER INFORMATION: Xaa is Gln or His
<220> FEATURE:
<221> NAME/KEY: misc_feature
<222> LOCATION: (6)..(6)
<223> OTHER INFORMATION: Xaa is Thr or Ser

<400> SEQUENCE: 73

Xaa Gln Ala Tyr Ser Xaa Pro Tyr Thr
1               5
```

-continued

```
<210> SEQ ID NO 74
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      portion LCDR1

<400> SEQUENCE: 74

Lys Ser Ser Gln Ser Val Gly Asn Asp Val Ala
1               5                   10

<210> SEQ ID NO 75
<211> LENGTH: 9
<212> TYPE: PRT
<213> ORGANISM: Artificial Sequence
<220> FEATURE:
<223> OTHER INFORMATION: anti-PD1 antibody molecule or antigen-binding
      portion LCDR3

<400> SEQUENCE: 75

Gln Gln Ala Tyr Ser Ser Pro Tyr Thr
1               5

<210> SEQ ID NO 76
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      portion LCDR1

<400> SEQUENCE: 76

Lys Ser Ser Gln Ser Val Thr Asn Asp Leu Ala
1               5                   10

<210> SEQ ID NO 77
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      portion LCDR1

<400> SEQUENCE: 77

Lys Ser Ser Gln Ser Val Gly Asn Asp Leu Ala
1               5                   10

<210> SEQ ID NO 78
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      portion LCDR2

<400> SEQUENCE: 78

Tyr Ala Tyr His Arg Phe Ser
1               5

<210> SEQ ID NO 79
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      portion LCDR2

<400> SEQUENCE: 79
```

Tyr Ala Ser His Arg Phe Ser
1               5

<210> SEQ ID NO 80
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      portion partial HCDR2

<400> SEQUENCE: 80

Tyr Val Asp Ser Val Lys Gly
1               5

<210> SEQ ID NO 81
<211> LENGTH: 9
<212> TYPE: PRT
<213> ORGANISM: Homo sapiens

<400> SEQUENCE: 81

Val Lys Gly Arg Phe Thr Ile Ser Arg
1               5

<210> SEQ ID NO 82
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 82

Gly Phe Ser Leu Thr Ser Tyr Gly Val His
1               5                   10

<210> SEQ ID NO 83
<211> LENGTH: 9
<212> TYPE: PRT
<213> ORGANISM: Artificial Sequence
<220> FEATURE:
<223> OTHER INFORMATION: LAF sequence

<400> SEQUENCE: 83

Leu Thr Ser Tyr Gly Val His Trp Ile
1               5

<210> SEQ ID NO 84
<211> LENGTH: 9
<212> TYPE: PRT
<213> ORGANISM: Artificial Sequence
<220> FEATURE:
<223> OTHER INFORMATION: GE peptide
<220> FEATURE:
<221> NAME/KEY: misc_feature
<222> LOCATION: (4)..(4)
<223> OTHER INFORMATION: Xaa is His or Ser

<400> SEQUENCE: 84

Tyr Gly Met Xaa Trp Val Arg Gln Ala
1               5

<210> SEQ ID NO 85
<211> LENGTH: 9
<212> TYPE: PRT
<213> ORGANISM: Artificial Sequence
<220> FEATURE:

```
<223> OTHER INFORMATION: TCED+ and LAF peptide

<400> SEQUENCE: 85

Tyr Trp Tyr Ile Asp Val Trp Gly Gln
1               5

<210> SEQ ID NO 86
<211> LENGTH: 9
<212> TYPE: PRT
<213> ORGANISM: Artificial Sequence
<220> FEATURE:
<223> OTHER INFORMATION: HAF peptide

<400> SEQUENCE: 86

Leu Glu Trp Ile Gly Val Ile Tyr Ala
1               5

<210> SEQ ID NO 87
<211> LENGTH: 9
<212> TYPE: PRT
<213> ORGANISM: Artificial Sequence
<220> FEATURE:
<223> OTHER INFORMATION: LAF peptide

<400> SEQUENCE: 87

Ile Gly Val Ile Tyr Ala Asp Gly Ser
1               5

<210> SEQ ID NO 88
<211> LENGTH: 9
<212> TYPE: PRT
<213> ORGANISM: Artificial Sequence
<220> FEATURE:
<223> OTHER INFORMATION: HAF peptide

<400> SEQUENCE: 88

Leu Glu Trp Val Gly Val Ile Trp Gln
1               5

<210> SEQ ID NO 89
<211> LENGTH: 10
<212> TYPE: PRT
<213> ORGANISM: Mus musculus

<400> SEQUENCE: 89

Gly Phe Ser Leu Thr Ser Tyr Gly Val His
1               5                   10

<210> SEQ ID NO 90
<211> LENGTH: 5
<212> TYPE: PRT
<213> ORGANISM: Mus musculus

<400> SEQUENCE: 90

Ser Tyr Gly Val His
1               5

<210> SEQ ID NO 91
<211> LENGTH: 7
<212> TYPE: PRT
<213> ORGANISM: Mus musculus

<400> SEQUENCE: 91

Gly Phe Ser Leu Thr Ser Tyr
1               5
```

```
<210> SEQ ID NO 92
<211> LENGTH: 8
<212> TYPE: PRT
<213> ORGANISM: Mus musculus

<400> SEQUENCE: 92

Gly Phe Ser Leu Thr Ser Tyr Gly
1               5

<210> SEQ ID NO 93
<211> LENGTH: 6
<212> TYPE: PRT
<213> ORGANISM: Mus musculus

<400> SEQUENCE: 93

Thr Ser Tyr Gly Val His
1               5

<210> SEQ ID NO 94
<211> LENGTH: 18
<212> TYPE: PRT
<213> ORGANISM: Mus musculus

<400> SEQUENCE: 94

Leu Gly Val Ile Trp Ala Gly Gly Ser Thr Asn Tyr Asn Ser Ala Leu
1               5                   10                  15

Met Ser

<210> SEQ ID NO 95
<211> LENGTH: 16
<212> TYPE: PRT
<213> ORGANISM: Mus musculus

<400> SEQUENCE: 95

Val Ile Trp Ala Gly Gly Ser Thr Asn Tyr Asn Ser Ala Leu Met Ser
1               5                   10                  15

<210> SEQ ID NO 96
<211> LENGTH: 6
<212> TYPE: PRT
<213> ORGANISM: Mus musculus

<400> SEQUENCE: 96

Trp Ala Gly Gly Ser Thr
1               5

<210> SEQ ID NO 97
<211> LENGTH: 8
<212> TYPE: PRT
<213> ORGANISM: Mus musculus

<400> SEQUENCE: 97

Ile Trp Ala Gly Gly Ser Thr Asn
1               5

<210> SEQ ID NO 98
<211> LENGTH: 15
<212> TYPE: PRT
<213> ORGANISM: Mus musculus

<400> SEQUENCE: 98

Ile Trp Ala Gly Gly Ser Thr Asn Tyr Asn Ser Ala Leu Met Ser
1               5                   10                  15
```

<210> SEQ ID NO 99
<211> LENGTH: 10
<212> TYPE: PRT
<213> ORGANISM: Mus musculus

<400> SEQUENCE: 99

Val Ile Trp Ala Gly Gly Ser Thr Asn Tyr
1               5                   10

<210> SEQ ID NO 100
<211> LENGTH: 12
<212> TYPE: PRT
<213> ORGANISM: Mus musculus

<400> SEQUENCE: 100

Leu Gly Val Ile Trp Ala Gly Gly Ser Thr Asn Tyr
1               5                   10

<210> SEQ ID NO 101
<211> LENGTH: 10
<212> TYPE: PRT
<213> ORGANISM: Mus musculus

<400> SEQUENCE: 101

Ala Tyr Gly Asn Tyr Trp Tyr Ile Asp Val
1               5                   10

<210> SEQ ID NO 102
<211> LENGTH: 12
<212> TYPE: PRT
<213> ORGANISM: Mus musculus

<400> SEQUENCE: 102

Ala Arg Ala Tyr Gly Asn Tyr Trp Tyr Ile Asp Val
1               5                   10

<210> SEQ ID NO 103
<211> LENGTH: 9
<212> TYPE: PRT
<213> ORGANISM: Mus musculus

<400> SEQUENCE: 103

Ala Tyr Gly Asn Tyr Trp Tyr Ile Asp
1               5

<210> SEQ ID NO 104
<211> LENGTH: 11
<212> TYPE: PRT
<213> ORGANISM: Mus musculus

<400> SEQUENCE: 104

Ala Arg Ala Tyr Gly Asn Tyr Trp Tyr Ile Asp
1               5                   10

<210> SEQ ID NO 105
<211> LENGTH: 11
<212> TYPE: PRT
<213> ORGANISM: Mus musculus

<400> SEQUENCE: 105

Lys Ala Ser Gln Ser Val Ser Asn Asp Val Ala
1               5                   10

<210> SEQ ID NO 106

```
<211> LENGTH: 6
<212> TYPE: PRT
<213> ORGANISM: Mus musculus

<400> SEQUENCE: 106

Gln Ser Val Ser Asn Asp
1               5

<210> SEQ ID NO 107
<211> LENGTH: 8
<212> TYPE: PRT
<213> ORGANISM: Mus musculus

<400> SEQUENCE: 107

Ala Ser Gln Ser Val Ser Asn Asp
1               5

<210> SEQ ID NO 108
<211> LENGTH: 7
<212> TYPE: PRT
<213> ORGANISM: Mus musculus

<400> SEQUENCE: 108

Ser Asn Asp Val Ala Trp Tyr
1               5

<210> SEQ ID NO 109
<211> LENGTH: 7
<212> TYPE: PRT
<213> ORGANISM: Mus musculus

<400> SEQUENCE: 109

Tyr Ala Phe His Arg Phe Thr
1               5

<210> SEQ ID NO 110
<211> LENGTH: 10
<212> TYPE: PRT
<213> ORGANISM: Mus musculus

<400> SEQUENCE: 110

Leu Leu Ile Tyr Tyr Ala Phe His Arg Phe
1               5                   10

<210> SEQ ID NO 111
<211> LENGTH: 9
<212> TYPE: PRT
<213> ORGANISM: Mus musculus

<400> SEQUENCE: 111

His Gln Ala Tyr Ser Ser Pro Tyr Thr
1               5

<210> SEQ ID NO 112
<211> LENGTH: 6
<212> TYPE: PRT
<213> ORGANISM: Mus musculus

<400> SEQUENCE: 112

Ala Tyr Ser Ser Pro Tyr
1               5

<210> SEQ ID NO 113
<211> LENGTH: 8
<212> TYPE: PRT
```

<213> ORGANISM: Mus musculus

<400> SEQUENCE: 113

His Gln Ala Tyr Ser Ser Pro Tyr
1               5

<210> SEQ ID NO 114
<211> LENGTH: 118
<212> TYPE: PRT
<213> ORGANISM: Mus musculus

<400> SEQUENCE: 114

Gln Val Gln Leu Lys Glu Ser Gly Pro Gly Leu Val Ala Pro Ser Lys
1               5                   10                  15

Asn Leu Ser Ile Thr Cys Thr Val Ser Gly Phe Ser Leu Thr Ser Tyr
            20                  25                  30

Gly Val His Trp Ile Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Arg Ser Gln Val Phe Leu
65                  70                  75                  80

Arg Met Asn Ser Leu Gln Thr Asp Asp Thr Ala Met Tyr Tyr Cys Ala
                85                  90                  95

Arg Ala Tyr Gly Asn Tyr Trp Tyr Ile Asp Val Trp Gly Ala Gly Thr
            100                 105                 110

Thr Val Thr Val Ser Ser
        115

<210> SEQ ID NO 115
<211> LENGTH: 118
<212> TYPE: PRT
<213> ORGANISM: Artificial Sequence
<220> FEATURE:
<223> OTHER INFORMATION: Hu317 VH IGHV4-4

<400> SEQUENCE: 115

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Tyr Ala Asp Gly Ser Thr Asn Tyr Asn Pro Ser Leu Lys
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 116
<211> LENGTH: 118
<212> TYPE: PRT
<213> ORGANISM: Artificial Sequence
<220> FEATURE:

<223> OTHER INFORMATION: VH GRAFT IGHV3-7

<400> SEQUENCE: 116

Glu Val Gln Leu Val Glu Ser Gly Gly Gly Leu Val Gln Pro Gly
1               5                   10                  15

Ser Leu Arg Leu Ser Cys Ala Ala Ser Gly Phe Ser Leu Thr Ser Tyr
            20                  25                  30

Gly Val His Trp Val Arg Gln Ala Pro Gly Lys Gly Leu Glu Trp Leu
        35                  40                  45

Gly Val Ile Trp Ala Gly Gly Ser Thr Asn Tyr Asn Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 117
<211> LENGTH: 107
<212> TYPE: PRT
<213> ORGANISM: Mus musculus

<400> SEQUENCE: 117

Asp Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Asn Tyr Ala Phe His Arg Phe Thr Gly Val Pro Asp Arg Phe Thr Gly
    50                  55                  60

Ser Gly Tyr Gly Thr Asp Phe Ile Phe Thr Ile Ser Thr Val Gln Ala
65                  70                  75                  80

Glu Asp Leu Ala Val Tyr Phe Cys His Gln Ala Tyr Ser Ser Pro Tyr
                85                  90                  95

Thr Phe Gly Gly Gly Thr Lys Leu Glu Met Lys
            100                 105

<210> SEQ ID NO 118
<211> LENGTH: 107
<212> TYPE: PRT
<213> ORGANISM: Artificial Sequence
<220> FEATURE:
<223> OTHER INFORMATION: Hu317 VL IGKV4-1

<400> SEQUENCE: 118

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Ser Asn Asp
            20                  25                  30

Val Ala Trp Tyr Gln Gln Lys Pro Gly Gln Pro Pro Lys Leu Leu Ile
        35                  40                  45

Asn Tyr Ala Phe His Arg Phe Thr Gly Val Pro Asp Arg Phe Ser Gly
    50                  55                  60

```
Ser Gly Tyr Gly Thr Asp Phe Thr Leu Thr Ile Ser Ser Leu Gln Ala
 65                  70                  75                  80

Glu Asp Val Ala Val Tyr Tyr Cys His Gln Ala Tyr Ser Ser Pro Tyr
                 85                  90                  95

Thr Phe Gly Gln Gly Thr Lys Leu Glu Ile Lys
            100                 105

<210> SEQ ID NO 119
<211> LENGTH: 107
<212> TYPE: PRT
<213> ORGANISM: Artificial Sequence
<220> FEATURE:
<223> OTHER INFORMATION: VL GRAFT IGKV4-1

<400> SEQUENCE: 119

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Ser Asn Asp
                20                  25                  30

Val Ala Trp Tyr Gln Gln Lys Pro Gly Gln Pro Pro Lys Leu Leu Ile
            35                  40                  45

Asn Tyr Ala Phe His Arg Phe Thr Gly Val Pro Asp Arg Phe Ser Gly
 50                  55                  60

Ser Gly Tyr Gly Thr Asp Phe Thr Leu Thr Ile Ser Ser Leu Gln Ala
 65                  70                  75                  80

Glu Asp Val Ala Val Tyr Tyr Cys His Gln Ala Tyr Ser Ser Pro Tyr
                 85                  90                  95

Thr Phe Gly Gln Gly Thr Lys Leu Glu Ile Lys
            100                 105

<210> SEQ ID NO 120
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 120

Gly Phe Asn Phe Ser Ser Tyr Gly Met His
1               5                   10

<210> SEQ ID NO 121
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 121

Gly Phe Ser Phe Ser Ser Tyr Gly Met Ser
1               5                   10

<210> SEQ ID NO 122
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 122
```

```
Gly Phe Ser Phe Ser Ser Tyr Gly Val His
1               5                   10
```

<210> SEQ ID NO 123
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 123

```
Gly Phe Ser Phe Ser Ser Tyr Gly Val Ser
1               5                   10
```

<210> SEQ ID NO 124
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 124

```
Gly Phe Ser Phe Ser Ser Tyr Trp Met His
1               5                   10
```

<210> SEQ ID NO 125
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 125

```
Gly Phe Ser Phe Thr Ser Tyr Gly Val His
1               5                   10
```

<210> SEQ ID NO 126
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 126

```
Gly Phe Ser Phe Thr Ser Tyr Gly Val Ser
1               5                   10
```

<210> SEQ ID NO 127
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 127

```
Gly Phe Ser Phe Thr Ser Tyr Trp Met His
1               5                   10
```

<210> SEQ ID NO 128
<211> LENGTH: 10
<212> TYPE: PRT
<213> ORGANISM: Artificial Sequence
<220> FEATURE:

```
<223> OTHER INFORMATION: anti-PD1 antibody molecule or antigen-binding
      portion HCDR1

<400> SEQUENCE: 128

Gly Phe Ser Leu Ser Ser Tyr Gly Ile Ser
1               5                   10

<210> SEQ ID NO 129
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 129

Gly Phe Ser Leu Ser Ser Tyr Gly Met His
1               5                   10

<210> SEQ ID NO 130
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 130

Gly Phe Ser Leu Ser Ser Tyr Gly Val His
1               5                   10

<210> SEQ ID NO 131
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 131

Gly Phe Ser Leu Ser Ser Tyr Gly Val Ser
1               5                   10

<210> SEQ ID NO 132
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 132

Gly Phe Ser Leu Ser Ser Tyr Trp Met His
1               5                   10

<210> SEQ ID NO 133
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 133

Gly Phe Ser Leu Thr Ser Tyr Trp Met His
1               5                   10
```

```
<210> SEQ ID NO 134
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 134

Gly Phe Thr Phe Ser Ser Tyr Gly Val Ser
1               5                   10

<210> SEQ ID NO 135
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 135

Gly Phe Thr Phe Thr Ser Tyr Gly Met His
1               5                   10

<210> SEQ ID NO 136
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 136

Gly Phe Thr Phe Thr Ser Tyr Gly Met Ser
1               5                   10

<210> SEQ ID NO 137
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 137

Gly Phe Thr Phe Thr Ser Tyr Gly Val His
1               5                   10

<210> SEQ ID NO 138
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 138

Gly Phe Thr Phe Thr Ser Tyr Gly Val Ser
1               5                   10

<210> SEQ ID NO 139
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 139
```

Gly Phe Thr Leu Ser Ser Tyr Gly Met Ser
1               5                   10

<210> SEQ ID NO 140
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 140

Gly Phe Thr Leu Ser Ser Tyr Gly Val His
1               5                   10

<210> SEQ ID NO 141
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 141

Gly Phe Thr Leu Ser Ser Tyr Gly Val Ser
1               5                   10

<210> SEQ ID NO 142
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 142

Gly Phe Thr Leu Ser Ser Tyr Trp Met His
1               5                   10

<210> SEQ ID NO 143
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 143

Gly Phe Thr Leu Thr Ser Tyr Gly Met His
1               5                   10

<210> SEQ ID NO 144
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 144

Gly Phe Thr Leu Thr Ser Tyr Gly Met Ser
1               5                   10

<210> SEQ ID NO 145
<211> LENGTH: 10
<212> TYPE: PRT
<213> ORGANISM: Artificial Sequence

```
<220> FEATURE:
<223> OTHER INFORMATION: anti-PD1 antibody molecule or antigen-binding
      portion HCDR1

<400> SEQUENCE: 145

Gly Phe Thr Leu Thr Ser Tyr Gly Val His
1               5                   10

<210> SEQ ID NO 146
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR1

<400> SEQUENCE: 146

Gly Phe Thr Leu Thr Ser Tyr Gly Val Ser
1               5                   10

<210> SEQ ID NO 147
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 147

Leu Ala Asn Ile Lys Ala Asp Gly Ser Glu Lys Tyr Val Asp Ser Val
1               5                   10                  15

Lys Gly

<210> SEQ ID NO 148
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 148

Leu Ala Asn Ile Lys Ala Asp Gly Ser Glu Asn Tyr Asn Asp Ser Val
1               5                   10                  15

Lys Gly

<210> SEQ ID NO 149
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 149

Leu Ala Asn Ile Lys Ala Asp Gly Ser Thr Lys Tyr Val Asp Ser Val
1               5                   10                  15

Lys Gly

<210> SEQ ID NO 150
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2
```

<400> SEQUENCE: 150

Leu Ala Asn Ile Lys Ala Asp Gly Ser Thr Asn Tyr Val Asp Ser Val
1               5                   10                  15

Lys Gly

<210> SEQ ID NO 151
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 151

Leu Ala Asn Ile Lys Ala Gly Gly Ser Glu Lys Tyr Asn Asp Ser Val
1               5                   10                  15

Lys Gly

<210> SEQ ID NO 152
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 152

Leu Ala Asn Ile Lys Ala Gly Gly Ser Glu Lys Tyr Val Asp Ser Val
1               5                   10                  15

Lys Gly

<210> SEQ ID NO 153
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 153

Leu Ala Asn Ile Lys Ala Gly Gly Ser Glu Asn Tyr Asn Asp Ser Val
1               5                   10                  15

Lys Gly

<210> SEQ ID NO 154
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 154

Leu Ala Asn Ile Lys Gln Asp Gly Ser Glu Lys Tyr Val Asp Ser Val
1               5                   10                  15

Lys Gly

<210> SEQ ID NO 155
<211> LENGTH: 18
<212> TYPE: PRT
<213> ORGANISM: Artificial Sequence
<220> FEATURE:
<223> OTHER INFORMATION: anti-PD1 antibody molecule or antigen-binding

```
            portion HCDR2

<400> SEQUENCE: 155

Leu Ala Asn Ile Lys Gln Asp Gly Ser Glu Asn Tyr Val Asp Ser Val
1               5                   10                  15

Lys Gly

<210> SEQ ID NO 156
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 156

Leu Ala Asn Ile Lys Gln Asp Gly Ser Thr Lys Tyr Asn Asp Ser Val
1               5                   10                  15

Lys Gly

<210> SEQ ID NO 157
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 157

Leu Ala Asn Ile Lys Gln Asp Gly Ser Thr Lys Tyr Val Asp Ser Val
1               5                   10                  15

Lys Gly

<210> SEQ ID NO 158
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 158

Leu Ala Asn Ile Trp Ala Asp Gly Ser Glu Lys Tyr Asn Asp Ser Val
1               5                   10                  15

Lys Gly

<210> SEQ ID NO 159
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 159

Leu Ala Asn Ile Trp Ala Asp Gly Ser Glu Lys Tyr Val Asp Ser Val
1               5                   10                  15

Lys Gly

<210> SEQ ID NO 160
<211> LENGTH: 18
<212> TYPE: PRT
<213> ORGANISM: Artificial Sequence
<220> FEATURE:
```

<223> OTHER INFORMATION: anti-PD1 antibody molecule or antigen-binding
      portion HCDR2

<400> SEQUENCE: 160

Leu Ala Asn Ile Trp Ala Asp Gly Ser Glu Asn Tyr Asn Asp Ser Val
1               5                   10                  15

Lys Gly

<210> SEQ ID NO 161
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 161

Leu Ala Asn Ile Trp Ala Asp Gly Ser Glu Asn Tyr Val Asp Ser Val
1               5                   10                  15

Lys Gly

<210> SEQ ID NO 162
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 162

Leu Ala Asn Ile Trp Ala Asp Gly Ser Thr Lys Tyr Asn Asp Ser Val
1               5                   10                  15

Lys Gly

<210> SEQ ID NO 163
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 163

Leu Ala Asn Ile Trp Ala Asp Gly Ser Thr Lys Tyr Val Asp Ser Val
1               5                   10                  15

Lys Gly

<210> SEQ ID NO 164
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 164

Leu Ala Asn Ile Trp Ala Asp Gly Ser Thr Asn Tyr Asn Asp Ser Val
1               5                   10                  15

Lys Gly

<210> SEQ ID NO 165
<211> LENGTH: 18
<212> TYPE: PRT
<213> ORGANISM: Artificial Sequence

```
<220> FEATURE:
<223> OTHER INFORMATION: anti-PD1 antibody molecule or antigen-binding
      portion HCDR2

<400> SEQUENCE: 165

Leu Ala Asn Ile Trp Ala Asp Gly Ser Thr Asn Tyr Val Asp Ser Val
1               5                   10                  15

Lys Gly

<210> SEQ ID NO 166
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 166

Leu Ala Asn Ile Trp Ala Gly Gly Ser Thr Asn Tyr Asn Asp Ser Val
1               5                   10                  15

Lys Gly

<210> SEQ ID NO 167
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 167

Leu Ala Asn Ile Trp Gln Asp Gly Ser Glu Lys Tyr Asn Asp Ser Val
1               5                   10                  15

Lys Gly

<210> SEQ ID NO 168
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 168

Leu Ala Asn Ile Trp Gln Asp Gly Ser Glu Lys Tyr Val Asp Ser Val
1               5                   10                  15

Lys Gly

<210> SEQ ID NO 169
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 169

Leu Ala Asn Ile Trp Gln Asp Gly Ser Glu Asn Tyr Asn Asp Ser Val
1               5                   10                  15

Lys Gly

<210> SEQ ID NO 170
<211> LENGTH: 18
<212> TYPE: PRT
```

```
<213> ORGANISM: Artificial Sequence
<220> FEATURE:
<223> OTHER INFORMATION: anti-PD1 antibody molecule or antigen-binding
      portion HCDR2

<400> SEQUENCE: 170

Leu Ala Asn Ile Trp Gln Asp Gly Ser Thr Lys Tyr Asn Asp Ser Val
1               5                   10                  15

Lys Gly

<210> SEQ ID NO 171
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 171

Leu Ala Asn Ile Trp Gln Asp Gly Ser Thr Lys Tyr Val Asp Ser Val
1               5                   10                  15

Lys Gly

<210> SEQ ID NO 172
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 172

Leu Ala Asn Ile Trp Gln Asp Gly Ser Thr Asn Tyr Asn Asp Ser Val
1               5                   10                  15

Lys Gly

<210> SEQ ID NO 173
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 173

Leu Ala Asn Ile Trp Gln Gly Gly Ser Glu Asn Tyr Val Asp Ser Val
1               5                   10                  15

Lys Gly

<210> SEQ ID NO 174
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 174

Leu Ala Val Ile Lys Ala Asp Gly Ser Glu Lys Tyr Asn Asp Ser Val
1               5                   10                  15

Lys Gly

<210> SEQ ID NO 175
<211> LENGTH: 18
```

```
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 175

Leu Ala Val Ile Lys Ala Asp Gly Ser Glu Asn Tyr Asn Asp Ser Val
1               5                   10                  15

Lys Gly

<210> SEQ ID NO 176
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 176

Leu Ala Val Ile Lys Ala Asp Gly Ser Thr Lys Tyr Val Asp Ser Val
1               5                   10                  15

Lys Gly

<210> SEQ ID NO 177
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 177

Leu Ala Val Ile Lys Ala Asp Gly Ser Thr Asn Tyr Asn Asp Ser Val
1               5                   10                  15

Lys Gly

<210> SEQ ID NO 178
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 178

Leu Ala Val Ile Lys Ala Gly Gly Ser Thr Asn Tyr Val Asp Ser Val
1               5                   10                  15

Lys Gly

<210> SEQ ID NO 179
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 179

Leu Ala Val Ile Lys Gln Asp Gly Ser Glu Lys Tyr Asn Asp Ser Val
1               5                   10                  15

Lys Gly

<210> SEQ ID NO 180
```

```
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 180

Leu Ala Val Ile Lys Gln Asp Gly Ser Thr Asn Tyr Asn Asp Ser Val
1               5                   10                  15

Lys Gly

<210> SEQ ID NO 181
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 181

Leu Ala Val Ile Lys Gln Asp Gly Ser Thr Asn Tyr Val Asp Ser Val
1               5                   10                  15

Lys Gly

<210> SEQ ID NO 182
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 182

Leu Ala Val Ile Trp Ala Asp Gly Ser Glu Lys Tyr Asn Asp Ser Val
1               5                   10                  15

Lys Gly

<210> SEQ ID NO 183
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 183

Leu Ala Val Ile Trp Ala Asp Gly Ser Glu Asn Tyr Asn Asp Ser Val
1               5                   10                  15

Lys Gly

<210> SEQ ID NO 184
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 184

Leu Ala Val Ile Trp Ala Asp Gly Ser Glu Asn Tyr Val Asp Ser Val
1               5                   10                  15

Lys Gly
```

```
<210> SEQ ID NO 185
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 185

Leu Ala Val Ile Trp Ala Asp Gly Ser Thr Lys Tyr Asn Asp Ser Val
1               5                   10                  15

Lys Gly

<210> SEQ ID NO 186
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 186

Leu Ala Val Ile Trp Ala Asp Gly Ser Thr Lys Tyr Val Asp Ser Val
1               5                   10                  15

Lys Gly

<210> SEQ ID NO 187
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 187

Leu Ala Val Ile Trp Ala Asp Gly Ser Thr Asn Tyr Asn Asp Ser Val
1               5                   10                  15

Lys Gly

<210> SEQ ID NO 188
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 188

Leu Ala Val Ile Trp Ala Gly Gly Ser Glu Lys Tyr Asn Asp Ser Val
1               5                   10                  15

Lys Gly

<210> SEQ ID NO 189
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 189

Leu Ala Val Ile Trp Ala Gly Gly Ser Glu Asn Tyr Asn Asp Ser Val
1               5                   10                  15

Lys Gly
```

<210> SEQ ID NO 190
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 190

Leu Ala Val Ile Trp Ala Gly Gly Ser Thr Lys Tyr Asn Asp Ser Val
1               5                   10                  15

Lys Gly

<210> SEQ ID NO 191
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 191

Leu Ala Val Ile Trp Gln Asp Gly Ser Glu Lys Tyr Asn Asp Ser Val
1               5                   10                  15

Lys Gly

<210> SEQ ID NO 192
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 192

Leu Ala Val Ile Trp Gln Asp Gly Ser Glu Lys Tyr Val Asp Ser Val
1               5                   10                  15

Lys Gly

<210> SEQ ID NO 193
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 193

Leu Ala Val Ile Trp Gln Asp Gly Ser Glu Asn Tyr Asn Asp Ser Val
1               5                   10                  15

Lys Gly

<210> SEQ ID NO 194
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 194

Leu Ala Val Ile Trp Gln Asp Gly Ser Glu Asn Tyr Val Asp Ser Val
1               5                   10                  15

Lys Gly

<210> SEQ ID NO 195
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 195

Leu Ala Val Ile Trp Gln Asp Gly Ser Thr Lys Tyr Asn Asp Ser Val
1               5                   10                  15

Lys Gly

<210> SEQ ID NO 196
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 196

Leu Ala Val Ile Trp Gln Asp Gly Ser Thr Lys Tyr Val Asp Ser Val
1               5                   10                  15

Lys Gly

<210> SEQ ID NO 197
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 197

Leu Ala Val Ile Trp Gln Asp Gly Ser Thr Asn Tyr Asn Asp Ser Val
1               5                   10                  15

Lys Gly

<210> SEQ ID NO 198
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 198

Leu Ala Val Ile Trp Gln Asp Gly Ser Thr Asn Tyr Val Asp Ser Val
1               5                   10                  15

Lys Gly

<210> SEQ ID NO 199
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 199

Leu Ala Val Ile Trp Gln Gly Gly Ser Glu Lys Tyr Asn Asp Ser Val
1               5                   10                  15

-continued

Lys Gly

<210> SEQ ID NO 200
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 200

Leu Ala Val Ile Trp Gln Gly Gly Ser Glu Asn Tyr Asn Asp Ser Val
1               5                   10                  15

Lys Gly

<210> SEQ ID NO 201
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 201

Leu Gly Asn Ile Lys Ala Asp Gly Ser Glu Asn Tyr Asn Asp Ser Val
1               5                   10                  15

Lys Gly

<210> SEQ ID NO 202
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 202

Leu Gly Asn Ile Lys Ala Asp Gly Ser Thr Lys Tyr Asn Asp Ser Val
1               5                   10                  15

Lys Gly

<210> SEQ ID NO 203
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 203

Leu Gly Asn Ile Lys Ala Asp Gly Ser Thr Lys Tyr Val Asp Ser Val
1               5                   10                  15

Lys Gly

<210> SEQ ID NO 204
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 204

Leu Gly Asn Ile Lys Ala Asp Gly Ser Thr Asn Tyr Asn Asp Ser Val
1               5                   10                  15

Lys Gly

```
<210> SEQ ID NO 205
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 205

Leu Gly Asn Ile Lys Ala Gly Gly Ser Thr Asn Tyr Asn Asp Ser Val
1               5                   10                  15

Lys Gly

<210> SEQ ID NO 206
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 206

Leu Gly Asn Ile Lys Ala Gly Gly Ser Thr Asn Tyr Val Asp Ser Val
1               5                   10                  15

Lys Gly

<210> SEQ ID NO 207
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 207

Leu Gly Asn Ile Lys Gln Asp Gly Ser Glu Asn Tyr Asn Asp Ser Val
1               5                   10                  15

Lys Gly

<210> SEQ ID NO 208
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 208

Leu Gly Asn Ile Lys Gln Asp Gly Ser Thr Lys Tyr Asn Asp Ser Val
1               5                   10                  15

Lys Gly

<210> SEQ ID NO 209
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 209

Leu Gly Asn Ile Lys Gln Asp Gly Ser Thr Asn Tyr Asn Asp Ser Val
```

-continued

```
1               5                   10                  15

Lys Gly

<210> SEQ ID NO 210
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 210

Leu Gly Asn Ile Lys Gln Gly Gly Ser Glu Asn Tyr Asn Asp Ser Val
1               5                   10                  15

Lys Gly

<210> SEQ ID NO 211
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 211

Leu Gly Asn Ile Lys Gln Gly Gly Ser Thr Lys Tyr Val Asp Ser Val
1               5                   10                  15

Lys Gly

<210> SEQ ID NO 212
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 212

Leu Gly Asn Ile Lys Gln Gly Gly Ser Thr Asn Tyr Asn Asp Ser Val
1               5                   10                  15

Lys Gly

<210> SEQ ID NO 213
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 213

Leu Gly Asn Ile Trp Ala Asp Gly Ser Glu Lys Tyr Asn Asp Ser Val
1               5                   10                  15

Lys Gly

<210> SEQ ID NO 214
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 214
```

```
Leu Gly Asn Ile Trp Ala Asp Gly Ser Glu Lys Tyr Val Asp Ser Val
1               5                   10                  15

Lys Gly

<210> SEQ ID NO 215
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 215

Leu Gly Asn Ile Trp Ala Asp Gly Ser Glu Asn Tyr Asn Asp Ser Val
1               5                   10                  15

Lys Gly

<210> SEQ ID NO 216
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 216

Leu Gly Asn Ile Trp Ala Asp Gly Ser Glu Asn Tyr Val Asp Ser Val
1               5                   10                  15

Lys Gly

<210> SEQ ID NO 217
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 217

Leu Gly Asn Ile Trp Ala Asp Gly Ser Thr Lys Tyr Asn Asp Ser Val
1               5                   10                  15

Lys Gly

<210> SEQ ID NO 218
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 218

Leu Gly Asn Ile Trp Ala Asp Gly Ser Thr Lys Tyr Val Asp Ser Val
1               5                   10                  15

Lys Gly

<210> SEQ ID NO 219
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 219
```

```
Leu Gly Asn Ile Trp Ala Asp Gly Ser Thr Asn Tyr Asn Asp Ser Val
1               5                   10                  15

Lys Gly

<210> SEQ ID NO 220
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 220

Leu Gly Asn Ile Trp Ala Asp Gly Ser Thr Asn Tyr Val Asp Ser Val
1               5                   10                  15

Lys Gly

<210> SEQ ID NO 221
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 221

Leu Gly Asn Ile Trp Ala Gly Gly Ser Glu Asn Tyr Val Asp Ser Val
1               5                   10                  15

Lys Gly

<210> SEQ ID NO 222
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 222

Leu Gly Asn Ile Trp Gln Asp Gly Ser Glu Lys Tyr Asn Asp Ser Val
1               5                   10                  15

Lys Gly

<210> SEQ ID NO 223
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 223

Leu Gly Asn Ile Trp Gln Asp Gly Ser Glu Lys Tyr Val Asp Ser Val
1               5                   10                  15

Lys Gly

<210> SEQ ID NO 224
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2
```

```
<400> SEQUENCE: 224

Leu Gly Asn Ile Trp Gln Asp Gly Ser Glu Asn Tyr Asn Asp Ser Val
1               5                   10                  15

Lys Gly

<210> SEQ ID NO 225
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 225

Leu Gly Asn Ile Trp Gln Asp Gly Ser Glu Asn Tyr Val Asp Ser Val
1               5                   10                  15

Lys Gly

<210> SEQ ID NO 226
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 226

Leu Gly Asn Ile Trp Gln Asp Gly Ser Thr Lys Tyr Asn Asp Ser Val
1               5                   10                  15

Lys Gly

<210> SEQ ID NO 227
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 227

Leu Gly Asn Ile Trp Gln Asp Gly Ser Thr Lys Tyr Val Asp Ser Val
1               5                   10                  15

Lys Gly

<210> SEQ ID NO 228
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 228

Leu Gly Asn Ile Trp Gln Asp Gly Ser Thr Asn Tyr Asn Asp Ser Val
1               5                   10                  15

Lys Gly

<210> SEQ ID NO 229
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2
```

<400> SEQUENCE: 229

Leu Gly Asn Ile Trp Gln Asp Gly Ser Thr Asn Tyr Val Asp Ser Val
1               5                   10                  15

Lys Gly

<210> SEQ ID NO 230
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 230

Leu Gly Asn Ile Trp Gln Gly Gly Ser Thr Asn Tyr Asn Asp Ser Val
1               5                   10                  15

Lys Gly

<210> SEQ ID NO 231
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 231

Leu Gly Val Ile Lys Ala Asp Gly Ser Glu Asn Tyr Asn Asp Ser Val
1               5                   10                  15

Lys Gly

<210> SEQ ID NO 232
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 232

Leu Gly Val Ile Lys Ala Asp Gly Ser Thr Lys Tyr Asn Asp Ser Val
1               5                   10                  15

Lys Gly

<210> SEQ ID NO 233
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 233

Val Ala Asn Ile Trp Gln Asp Gly Ser Thr Asn Tyr Asn Asp Ser Val
1               5                   10                  15

Lys Gly

<210> SEQ ID NO 234
<211> LENGTH: 18
<212> TYPE: PRT
<213> ORGANISM: Artificial Sequence
<220> FEATURE:
<223> OTHER INFORMATION: anti-PD1 antibody molecule or antigen-binding portion HCDR2

<400> SEQUENCE: 234

Leu Gly Val Ile Lys Ala Asp Gly Ser Thr Asn Tyr Asn Asp Ser Val
1               5                   10                  15

Lys Gly

<210> SEQ ID NO 235
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 235

Leu Gly Val Ile Lys Gln Asp Gly Ser Glu Asn Tyr Asn Asp Ser Val
1               5                   10                  15

Lys Gly

<210> SEQ ID NO 236
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 236

Leu Gly Val Ile Lys Gln Asp Gly Ser Thr Lys Tyr Asn Asp Ser Val
1               5                   10                  15

Lys Gly

<210> SEQ ID NO 237
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 237

Leu Gly Val Ile Lys Gln Asp Gly Ser Thr Lys Tyr Val Asp Ser Val
1               5                   10                  15

Lys Gly

<210> SEQ ID NO 238
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 238

Leu Gly Val Ile Lys Gln Asp Gly Ser Thr Asn Tyr Asn Asp Ser Val
1               5                   10                  15

Lys Gly

<210> SEQ ID NO 239
<211> LENGTH: 18
<212> TYPE: PRT
<213> ORGANISM: Artificial Sequence
<220> FEATURE:

```
<223> OTHER INFORMATION: anti-PD1 antibody molecule or antigen-binding
      portion HCDR2

<400> SEQUENCE: 239

Leu Gly Val Ile Lys Gln Gly Gly Ser Glu Asn Tyr Asn Asp Ser Val
1               5                   10                  15

Lys Gly

<210> SEQ ID NO 240
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 240

Leu Gly Val Ile Trp Ala Asp Gly Ser Glu Lys Tyr Asn Asp Ser Val
1               5                   10                  15

Lys Gly

<210> SEQ ID NO 241
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 241

Leu Gly Val Ile Trp Ala Asp Gly Ser Glu Asn Tyr Asn Asp Ser Val
1               5                   10                  15

Lys Gly

<210> SEQ ID NO 242
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 242

Leu Gly Val Ile Trp Ala Asp Gly Ser Thr Lys Tyr Asn Asp Ser Val
1               5                   10                  15

Lys Gly

<210> SEQ ID NO 243
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 243

Leu Gly Val Ile Trp Ala Asp Gly Ser Thr Lys Tyr Val Asp Ser Val
1               5                   10                  15

Lys Gly

<210> SEQ ID NO 244
<211> LENGTH: 18
<212> TYPE: PRT
<213> ORGANISM: Artificial Sequence
```

```
<220> FEATURE:
<223> OTHER INFORMATION: anti-PD1 antibody molecule or antigen-binding
      portion HCDR2

<400> SEQUENCE: 244

Leu Gly Val Ile Trp Ala Asp Gly Ser Thr Asn Tyr Asn Asp Ser Val
1               5                   10                  15

Lys Gly

<210> SEQ ID NO 245
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 245

Leu Gly Val Ile Trp Ala Asp Gly Ser Thr Asn Tyr Val Asp Ser Val
1               5                   10                  15

Lys Gly

<210> SEQ ID NO 246
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 246

Leu Gly Val Ile Trp Ala Asp Gly Ser Thr Ser Tyr Asn Asp Ser Val
1               5                   10                  15

Lys Gly

<210> SEQ ID NO 247
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 247

Leu Gly Val Ile Trp Ala Gly Gly Ser Thr Asn Tyr Asn Asp Ser Val
1               5                   10                  15

Lys Gly

<210> SEQ ID NO 248
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 248

Leu Gly Val Ile Trp Pro Asp Gly Ser Thr Asn Tyr Asn Asp Ser Val
1               5                   10                  15

Lys Gly

<210> SEQ ID NO 249
<211> LENGTH: 18
<212> TYPE: PRT
```

<213> ORGANISM: Artificial Sequence
<220> FEATURE:
<223> OTHER INFORMATION: anti-PD1 antibody molecule or antigen-binding
      portion HCDR2

<400> SEQUENCE: 249

Leu Gly Val Ile Trp Gln Asp Gly Ser Glu Lys Tyr Asn Asp Ser Val
1               5                   10                  15

Lys Gly

<210> SEQ ID NO 250
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 250

Leu Gly Val Ile Trp Gln Asp Gly Ser Glu Lys Tyr Val Asp Ser Val
1               5                   10                  15

Lys Gly

<210> SEQ ID NO 251
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 251

Leu Gly Val Ile Trp Gln Asp Gly Ser Glu Asn Tyr Asn Asp Ser Val
1               5                   10                  15

Lys Gly

<210> SEQ ID NO 252
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 252

Leu Gly Val Ile Trp Gln Asp Gly Ser Glu Asn Tyr Val Asp Ser Val
1               5                   10                  15

Lys Gly

<210> SEQ ID NO 253
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 253

Leu Gly Val Ile Trp Gln Asp Gly Ser Thr Lys Tyr Asn Asp Ser Val
1               5                   10                  15

Lys Gly

<210> SEQ ID NO 254
<211> LENGTH: 18

```
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 254

Leu Gly Val Ile Trp Gln Asp Gly Ser Thr Lys Tyr Val Asp Ser Val
1               5                   10                  15

Lys Gly

<210> SEQ ID NO 255
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 255

Leu Gly Val Ile Trp Gln Asp Gly Ser Thr Asn Tyr Asn Asp Ser Val
1               5                   10                  15

Lys Gly

<210> SEQ ID NO 256
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 256

Leu Gly Val Ile Trp Gln Asp Gly Ser Thr Asn Tyr Val Asp Ser Val
1               5                   10                  15

Lys Gly

<210> SEQ ID NO 257
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 257

Leu Gly Val Ile Trp Gln Gly Gly Ser Thr Lys Tyr Asn Asp Ser Val
1               5                   10                  15

Lys Gly

<210> SEQ ID NO 258
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 258

Leu Gly Val Ile Trp Gln Gly Gly Ser Thr Asn Tyr Asn Asp Ser Val
1               5                   10                  15

Lys Gly

<210> SEQ ID NO 259
```

```
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 259

Val Ala Asn Ile Lys Ala Asp Gly Ser Glu Lys Tyr Val Asp Ser Val
1               5                   10                  15

Lys Gly

<210> SEQ ID NO 260
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 260

Val Ala Asn Ile Lys Ala Asp Gly Ser Glu Asn Tyr Val Asp Ser Val
1               5                   10                  15

Lys Gly

<210> SEQ ID NO 261
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 261

Val Ala Asn Ile Lys Ala Asp Gly Ser Thr Lys Tyr Val Asp Ser Val
1               5                   10                  15

Lys Gly

<210> SEQ ID NO 262
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 262

Val Ala Asn Ile Lys Gln Asp Gly Ser Glu Lys Tyr Asn Asp Ser Val
1               5                   10                  15

Lys Gly

<210> SEQ ID NO 263
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 263

Val Ala Asn Ile Lys Gln Asp Gly Ser Glu Lys Tyr Val Asp Ser Val
1               5                   10                  15

Lys Gly
```

```
<210> SEQ ID NO 264
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 264

Val Ala Asn Ile Lys Gln Asp Gly Ser Thr Lys Tyr Asn Asp Ser Val
1               5                   10                  15

Lys Gly

<210> SEQ ID NO 265
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 265

Val Ala Asn Ile Lys Gln Asp Gly Ser Thr Asn Tyr Asn Asp Ser Val
1               5                   10                  15

Lys Gly

<210> SEQ ID NO 266
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 266

Val Ala Asn Ile Trp Ala Asp Gly Ser Glu Lys Tyr Asn Asp Ser Val
1               5                   10                  15

Lys Gly

<210> SEQ ID NO 267
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 267

Val Ala Asn Ile Trp Ala Asp Gly Ser Thr Lys Tyr Asn Asp Ser Val
1               5                   10                  15

Lys Gly

<210> SEQ ID NO 268
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 268

Val Ala Asn Ile Trp Ala Asp Gly Ser Thr Asn Tyr Asn Asp Ser Val
1               5                   10                  15

Lys Gly
```

<210> SEQ ID NO 269
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 269

Val Ala Asn Ile Trp Ala Asp Gly Ser Thr Asn Tyr Val Asp Ser Val
1               5                   10                  15

Lys Gly

<210> SEQ ID NO 270
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 270

Val Ala Asn Ile Trp Ala Gly Gly Ser Glu Asn Tyr Asn Asp Ser Val
1               5                   10                  15

Lys Gly

<210> SEQ ID NO 271
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 271

Val Ala Asn Ile Trp Gln Asp Gly Ser Glu Lys Tyr Asn Asp Ser Val
1               5                   10                  15

Lys Gly

<210> SEQ ID NO 272
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 272

Val Ala Asn Ile Trp Gln Asp Gly Ser Glu Asn Tyr Asn Asp Ser Val
1               5                   10                  15

Lys Gly

<210> SEQ ID NO 273
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 273

Val Ala Asn Ile Trp Gln Asp Gly Ser Glu Asn Tyr Val Asp Ser Val
1               5                   10                  15

Lys Gly

<210> SEQ ID NO 274
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 274

Val Ala Asn Ile Trp Gln Asp Gly Ser Thr Lys Tyr Asn Asp Ser Val
1               5                   10                  15

Lys Gly

<210> SEQ ID NO 275
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 275

Val Ala Asn Ile Trp Gln Gly Gly Ser Glu Lys Tyr Asn Asp Ser Val
1               5                   10                  15

Lys Gly

<210> SEQ ID NO 276
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 276

Val Ala Asn Ile Trp Gln Gly Gly Ser Thr Lys Tyr Asn Asp Ser Val
1               5                   10                  15

Lys Gly

<210> SEQ ID NO 277
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 277

Val Ala Val Ile Lys Ala Asp Gly Ser Thr Asn Tyr Asn Asp Ser Val
1               5                   10                  15

Lys Gly

<210> SEQ ID NO 278
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 278

Val Ala Val Ile Lys Gln Asp Gly Ser Glu Asn Tyr Val Asp Ser Val
1               5                   10                  15

Lys Gly

<210> SEQ ID NO 279
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 279

Val Ala Val Ile Lys Gln Asp Gly Ser Thr Lys Tyr Asn Asp Ser Val
1               5                   10                  15

Lys Gly

<210> SEQ ID NO 280
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 280

Val Ala Val Ile Lys Gln Asp Gly Ser Thr Asn Tyr Asn Asp Ser Val
1               5                   10                  15

Lys Gly

<210> SEQ ID NO 281
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 281

Val Ala Val Ile Lys Gln Asp Gly Ser Thr Asn Tyr Val Asp Ser Val
1               5                   10                  15

Lys Gly

<210> SEQ ID NO 282
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 282

Val Ala Val Ile Trp Ala Asp Gly Ser Glu Lys Tyr Val Asp Ser Val
1               5                   10                  15

Lys Gly

<210> SEQ ID NO 283
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 283

Val Ala Val Ile Trp Ala Asp Gly Ser Glu Asn Tyr Asn Asp Ser Val
1               5                   10                  15

Lys Gly

<210> SEQ ID NO 284
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 284

Val Ala Val Ile Trp Ala Asp Gly Ser Thr Lys Tyr Asn Asp Ser Val
1               5                   10                  15

Lys Gly

<210> SEQ ID NO 285
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 285

Val Ala Val Ile Trp Ala Asp Gly Ser Thr Lys Tyr Val Asp Ser Val
1               5                   10                  15

Lys Gly

<210> SEQ ID NO 286
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 286

Val Ala Val Ile Trp Ala Asp Gly Ser Thr Asn Tyr Asn Asp Ser Val
1               5                   10                  15

Lys Gly

<210> SEQ ID NO 287
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 287

Val Ala Val Ile Trp Gln Asp Gly Ser Glu Lys Tyr Asn Asp Ser Val
1               5                   10                  15

Lys Gly

<210> SEQ ID NO 288
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 288

Val Ala Val Ile Trp Gln Asp Gly Ser Glu Asn Tyr Asn Asp Ser Val

```
1               5                   10                  15
Lys Gly

<210> SEQ ID NO 289
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 289

Val Ala Val Ile Trp Gln Asp Gly Ser Glu Asn Tyr Val Asp Ser Val
1               5                   10                  15

Lys Gly

<210> SEQ ID NO 290
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 290

Val Ala Val Ile Trp Gln Asp Gly Ser Thr Lys Tyr Asn Asp Ser Val
1               5                   10                  15

Lys Gly

<210> SEQ ID NO 291
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 291

Val Ala Val Ile Trp Gln Asp Gly Ser Thr Lys Tyr Val Asp Ser Val
1               5                   10                  15

Lys Gly

<210> SEQ ID NO 292
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 292

Val Ala Val Ile Trp Gln Asp Gly Ser Thr Asn Tyr Asn Asp Ser Val
1               5                   10                  15

Lys Gly

<210> SEQ ID NO 293
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 293
```

```
Val Ala Val Ile Trp Gln Gly Gly Ser Thr Lys Tyr Asn Asp Ser Val
1               5                   10                  15

Lys Gly

<210> SEQ ID NO 294
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 294

Val Gly Asn Ile Lys Ala Asp Gly Ser Glu Asn Tyr Asn Asp Ser Val
1               5                   10                  15

Lys Gly

<210> SEQ ID NO 295
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 295

Val Gly Asn Ile Lys Ala Asp Gly Ser Thr Lys Tyr Asn Asp Ser Val
1               5                   10                  15

Lys Gly

<210> SEQ ID NO 296
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 296

Val Gly Asn Ile Lys Ala Asp Gly Ser Thr Asn Tyr Asn Asp Ser Val
1               5                   10                  15

Lys Gly

<210> SEQ ID NO 297
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 297

Val Gly Asn Ile Lys Ala Gly Gly Ser Thr Asn Tyr Val Asp Ser Val
1               5                   10                  15

Lys Gly

<210> SEQ ID NO 298
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 298
```

Val Gly Asn Ile Lys Gln Asp Gly Ser Glu Asn Tyr Asn Asp Ser Val
1               5                   10                  15

Lys Gly

<210> SEQ ID NO 299
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 299

Val Gly Asn Ile Lys Gln Asp Gly Ser Glu Asn Tyr Val Asp Ser Val
1               5                   10                  15

Lys Gly

<210> SEQ ID NO 300
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 300

Val Gly Asn Ile Lys Gln Asp Gly Ser Thr Lys Tyr Asn Asp Ser Val
1               5                   10                  15

Lys Gly

<210> SEQ ID NO 301
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 301

Val Gly Asn Ile Lys Gln Asp Gly Ser Thr Asn Tyr Asn Asp Ser Val
1               5                   10                  15

Lys Gly

<210> SEQ ID NO 302
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 302

Val Gly Asn Ile Lys Gln Asp Gly Ser Thr Asn Tyr Val Asp Ser Val
1               5                   10                  15

Lys Gly

<210> SEQ ID NO 303
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

```
<400> SEQUENCE: 303

Val Gly Asn Ile Lys Gln Gly Gly Ser Thr Lys Tyr Asn Asp Ser Val
1               5                   10                  15

Lys Gly

<210> SEQ ID NO 304
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 304

Val Gly Asn Ile Trp Ala Asp Gly Ser Glu Asn Tyr Asn Asp Ser Val
1               5                   10                  15

Lys Gly

<210> SEQ ID NO 305
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 305

Val Gly Asn Ile Trp Ala Asp Gly Ser Thr Lys Tyr Val Asp Ser Val
1               5                   10                  15

Lys Gly

<210> SEQ ID NO 306
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 306

Val Gly Asn Ile Trp Ala Asp Gly Ser Thr Asn Tyr Asn Asp Ser Val
1               5                   10                  15

Lys Gly

<210> SEQ ID NO 307
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 307

Val Gly Asn Ile Trp Ala Asp Gly Ser Thr Asn Tyr Val Asp Ser Val
1               5                   10                  15

Lys Gly

<210> SEQ ID NO 308
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2
```

```
<400> SEQUENCE: 308

Val Gly Asn Ile Trp Gln Asp Gly Ser Glu Lys Tyr Asn Asp Ser Val
1               5                   10                  15

Lys Gly

<210> SEQ ID NO 309
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 309

Val Gly Asn Ile Trp Gln Asp Gly Ser Glu Lys Tyr Val Asp Ser Val
1               5                   10                  15

Lys Gly

<210> SEQ ID NO 310
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 310

Val Gly Asn Ile Trp Gln Asp Gly Ser Glu Asn Tyr Val Asp Ser Val
1               5                   10                  15

Lys Gly

<210> SEQ ID NO 311
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 311

Val Gly Asn Ile Trp Gln Asp Gly Ser Thr Lys Tyr Asn Asp Ser Val
1               5                   10                  15

Lys Gly

<210> SEQ ID NO 312
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 312

Val Gly Asn Ile Trp Gln Asp Gly Ser Thr Lys Tyr Val Asp Ser Val
1               5                   10                  15

Lys Gly

<210> SEQ ID NO 313
<211> LENGTH: 18
<212> TYPE: PRT
<213> ORGANISM: Artificial Sequence
<220> FEATURE:
<223> OTHER INFORMATION: anti-PD1 antibody molecule or antigen-binding
``` portion HCDR2

<400> SEQUENCE: 313

Val Gly Asn Ile Trp Gln Asp Gly Ser Thr Asn Tyr Asn Asp Ser Val
1               5                   10                  15

Lys Gly

<210> SEQ ID NO 314
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 314

Val Gly Asn Ile Trp Gln Asp Gly Ser Thr Asn Tyr Val Asp Ser Val
1               5                   10                  15

Lys Gly

<210> SEQ ID NO 315
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 315

Val Gly Asn Ile Trp Gln Gly Gly Ser Glu Lys Tyr Asn Asp Ser Val
1               5                   10                  15

Lys Gly

<210> SEQ ID NO 316
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 316

Val Gly Val Ile Lys Ala Asp Gly Ser Thr Lys Tyr Asn Asp Ser Val
1               5                   10                  15

Lys Gly

<210> SEQ ID NO 317
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 317

Val Gly Val Ile Lys Ala Asp Gly Ser Thr Asn Tyr Asn Asp Ser Val
1               5                   10                  15

Lys Gly

<210> SEQ ID NO 318
<211> LENGTH: 18
<212> TYPE: PRT
<213> ORGANISM: Artificial Sequence
<220> FEATURE:

<223> OTHER INFORMATION: anti-PD1 antibody molecule or antigen-binding
      portion HCDR2

<400> SEQUENCE: 318

Val Gly Val Ile Lys Ala Asp Gly Ser Thr Asn Tyr Val Asp Ser Val
1               5                   10                  15

Lys Gly

<210> SEQ ID NO 319
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 319

Val Gly Val Ile Lys Gln Asp Gly Ser Glu Asn Tyr Asn Asp Ser Val
1               5                   10                  15

Lys Gly

<210> SEQ ID NO 320
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 320

Val Gly Val Ile Lys Gln Asp Gly Ser Thr Lys Tyr Asn Asp Ser Val
1               5                   10                  15

Lys Gly

<210> SEQ ID NO 321
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 321

Val Gly Val Ile Lys Gln Asp Gly Ser Thr Asn Tyr Asn Asp Ser Val
1               5                   10                  15

Lys Gly

<210> SEQ ID NO 322
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 322

Val Gly Val Ile Trp Ala Asp Gly Ser Glu Lys Tyr Asn Asp Ser Val
1               5                   10                  15

Lys Gly

<210> SEQ ID NO 323
<211> LENGTH: 18
<212> TYPE: PRT
<213> ORGANISM: Artificial Sequence

```
<220> FEATURE:
<223> OTHER INFORMATION: anti-PD1 antibody molecule or antigen-binding
      portion HCDR2

<400> SEQUENCE: 323

Val Gly Val Ile Trp Ala Asp Gly Ser Glu Asn Tyr Asn Asp Ser Val
1               5                   10                  15

Lys Gly

<210> SEQ ID NO 324
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 324

Val Gly Val Ile Trp Ala Asp Gly Ser Glu Asn Tyr Val Asp Ser Val
1               5                   10                  15

Lys Gly

<210> SEQ ID NO 325
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 325

Val Gly Val Ile Trp Ala Asp Gly Ser Thr Lys Tyr Asn Asp Ser Val
1               5                   10                  15

Lys Gly

<210> SEQ ID NO 326
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 326

Val Gly Val Ile Trp Ala Asp Gly Ser Thr Lys Tyr Val Asp Ser Val
1               5                   10                  15

Lys Gly

<210> SEQ ID NO 327
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 327

Val Gly Val Ile Trp Ala Asp Gly Ser Thr Asn Tyr Asn Asp Ser Val
1               5                   10                  15

Lys Gly

<210> SEQ ID NO 328
<211> LENGTH: 18
<212> TYPE: PRT
```

<213> ORGANISM: Artificial Sequence
<220> FEATURE:
<223> OTHER INFORMATION: anti-PD1 antibody molecule or antigen-binding
      portion HCDR2

<400> SEQUENCE: 328

Val Gly Val Ile Trp Ala Asp Gly Ser Thr Asn Tyr Val Asp Ser Val
1               5                   10                  15

Lys Gly

<210> SEQ ID NO 329
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 329

Val Gly Val Ile Trp Gln Asp Gly Ser Glu Lys Tyr Asn Asp Ser Val
1               5                   10                  15

Lys Gly

<210> SEQ ID NO 330
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 330

Val Gly Val Ile Trp Gln Asp Gly Ser Glu Lys Tyr Val Asp Ser Val
1               5                   10                  15

Lys Gly

<210> SEQ ID NO 331
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 331

Val Gly Val Ile Trp Gln Asp Gly Ser Glu Asn Tyr Asn Asp Ser Val
1               5                   10                  15

Lys Gly

<210> SEQ ID NO 332
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 332

Val Gly Val Ile Trp Gln Asp Gly Ser Thr Lys Tyr Asn Asp Ser Val
1               5                   10                  15

Lys Gly

<210> SEQ ID NO 333
<211> LENGTH: 18

```
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 333

Val Gly Val Ile Trp Gln Asp Gly Ser Thr Lys Tyr Val Asp Ser Val
1               5                   10                  15

Lys Gly

<210> SEQ ID NO 334
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 334

Val Gly Val Ile Trp Gln Asp Gly Ser Thr Asn Tyr Asn Asp Ser Val
1               5                   10                  15

Lys Gly

<210> SEQ ID NO 335
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 335

Val Gly Val Ile Trp Gln Gly Gly Ser Glu Lys Tyr Val Asp Ser Val
1               5                   10                  15

Lys Gly

<210> SEQ ID NO 336
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion HCDR2

<400> SEQUENCE: 336

Val Gly Val Ile Trp Gln Gly Gly Ser Thr Asn Tyr Asn Asp Ser Val
1               5                   10                  15

Lys Gly

<210> SEQ ID NO 337
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 337

Ala Phe Gly Asn Tyr Trp Tyr Ile Asp Val
1               5                   10

<210> SEQ ID NO 338
<211> LENGTH: 10
<212> TYPE: PRT
```

<213> ORGANISM: Artificial Sequence
<220> FEATURE:
<223> OTHER INFORMATION: anti-PD1 antibody molecule or antigen-binding
      portion HCDR3

<400> SEQUENCE: 338

Ala Trp Gly Asn Tyr Trp Tyr Ile Asp Val
1               5                   10

<210> SEQ ID NO 339
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 339

Ala Tyr Gly Ala Tyr Trp Tyr Ile Asp Val
1               5                   10

<210> SEQ ID NO 340
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 340

Ala Tyr Gly Glu Tyr Trp Tyr Ile Asp Val
1               5                   10

<210> SEQ ID NO 341
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 341

Ala Tyr Gly Phe Tyr Trp Tyr Ile Asp Val
1               5                   10

<210> SEQ ID NO 342
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 342

Ala Tyr Gly Gly Tyr Trp Tyr Ile Asp Val
1               5                   10

<210> SEQ ID NO 343
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 343

Ala Tyr Gly His Tyr Trp Tyr Ile Asp Val
1               5                   10

<210> SEQ ID NO 344
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 344

Ala Tyr Gly Ile Tyr Trp Tyr Ile Asp Asn
1               5                   10

<210> SEQ ID NO 345
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 345

Ala Tyr Gly Asn Trp Trp Tyr Ile Asp Val
1               5                   10

<210> SEQ ID NO 346
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 346

Ala Tyr Gly Asn Tyr Phe Tyr Ile Asp Val
1               5                   10

<210> SEQ ID NO 347
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 347

Ala Tyr Gly Asn Tyr Phe Tyr Ile Asp Trp
1               5                   10

<210> SEQ ID NO 348
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 348

Ala Tyr Gly Asn Tyr His Tyr Ile Asp Val
1               5                   10

<210> SEQ ID NO 349
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 349

Ala Tyr Gly Asn Tyr Pro Tyr Ile Asp Val
1               5                   10

<210> SEQ ID NO 350
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 350

Ala Tyr Gly Asn Tyr Gln Tyr Ile Asp Val
1               5                   10

<210> SEQ ID NO 351
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 351

Ala Tyr Gly Asn Tyr Ser Tyr Ile Asp Val
1               5                   10

<210> SEQ ID NO 352
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 352

Ala Tyr Gly Asn Tyr Val Tyr Ile Asp Val
1               5                   10

<210> SEQ ID NO 353
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 353

Ala Tyr Gly Asn Tyr Trp Tyr Ala Asp Val
1               5                   10

<210> SEQ ID NO 354
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 354

Ala Tyr Gly Asn Tyr Trp Tyr Gly Asp Val
1               5                   10

<210> SEQ ID NO 355
<211> LENGTH: 10

```
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 355

Ala Tyr Gly Asn Tyr Trp Tyr Ile Asp Ala
1               5                   10

<210> SEQ ID NO 356
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 356

Ala Tyr Gly Asn Tyr Trp Tyr Ile Asp Glu
1               5                   10

<210> SEQ ID NO 357
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 357

Ala Tyr Gly Asn Tyr Trp Tyr Ile Asp Phe
1               5                   10

<210> SEQ ID NO 358
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 358

Ala Tyr Gly Asn Tyr Trp Tyr Ile Asp Gly
1               5                   10

<210> SEQ ID NO 359
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 359

Ala Tyr Gly Asn Tyr Trp Tyr Ile Asp His
1               5                   10

<210> SEQ ID NO 360
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 360

Ala Tyr Gly Asn Tyr Trp Tyr Ile Asp Ile
```

```
<210> SEQ ID NO 361
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 361

Ala Tyr Gly Asn Tyr Trp Tyr Ile Asp Lys
1               5                   10

<210> SEQ ID NO 362
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 362

Ala Tyr Gly Asn Tyr Trp Tyr Ile Asp Leu
1               5                   10

<210> SEQ ID NO 363
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 363

Ala Tyr Gly Asn Tyr Trp Tyr Ile Asp Met
1               5                   10

<210> SEQ ID NO 364
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 364

Ala Tyr Gly Asn Tyr Trp Tyr Ile Asp Ser
1               5                   10

<210> SEQ ID NO 365
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 365

Ala Tyr Gly Asn Tyr Trp Tyr Ile Asp Thr
1               5                   10

<210> SEQ ID NO 366
<211> LENGTH: 10
<212> TYPE: PRT
<213> ORGANISM: Artificial Sequence
<220> FEATURE:
<223> OTHER INFORMATION: anti-PD1 antibody molecule or antigen-binding
``` portion HCDR3

<400> SEQUENCE: 366

Ala Tyr Gly Asn Tyr Trp Tyr Ile Asp Trp
1               5                   10

<210> SEQ ID NO 367
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 367

Ala Tyr Gly Asn Tyr Trp Tyr Ile Asp Tyr
1               5                   10

<210> SEQ ID NO 368
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 368

Ala Tyr Gly Asn Tyr Trp Tyr Ile Glu Val
1               5                   10

<210> SEQ ID NO 369
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 369

Ala Tyr Gly Asn Tyr Trp Tyr Leu Asp Val
1               5                   10

<210> SEQ ID NO 370
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 370

Ala Tyr Gly Asn Tyr Trp Tyr Met Asp Val
1               5                   10

<210> SEQ ID NO 371
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 371

Ala Tyr Gly Asn Tyr Trp Tyr Ser Asp Val
1               5                   10

<210> SEQ ID NO 372

```
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 372

Ala Tyr Gly Asn Tyr Trp Tyr Thr Asp Val
1               5                   10

<210> SEQ ID NO 373
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 373

Ala Tyr Gly Asn Tyr Trp Tyr Val Asp Val
1               5                   10

<210> SEQ ID NO 374
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 374

Ala Tyr Gly Asn Tyr Trp Tyr Tyr Asp Val
1               5                   10

<210> SEQ ID NO 375
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 375

Ala Tyr Gly Gln Tyr Trp Tyr Ile Asp Val
1               5                   10

<210> SEQ ID NO 376
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 376

Ala Tyr Gly Arg Tyr Trp Tyr Ile Asp Val
1               5                   10

<210> SEQ ID NO 377
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 377
```

Ala Tyr Gly Ser Tyr Trp Tyr Ile Asp Val
1               5                   10

<210> SEQ ID NO 378
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 378

Ala Tyr Gly Thr Tyr Trp Tyr Ile Asp Val
1               5                   10

<210> SEQ ID NO 379
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 379

Ala Tyr Gly Val Tyr Trp Tyr Ile Asp Arg
1               5                   10

<210> SEQ ID NO 380
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 380

Ala Tyr Gly Val Tyr Trp Tyr Ile Asp Val
1               5                   10

<210> SEQ ID NO 381
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 381

Ala Tyr Gly Trp Tyr Trp Tyr Ile Asp Val
1               5                   10

<210> SEQ ID NO 382
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 382

Ala Tyr Gly Tyr Tyr Trp Tyr Ile Asp Val
1               5                   10

<210> SEQ ID NO 383
<211> LENGTH: 10
<212> TYPE: PRT
<213> ORGANISM: Artificial Sequence
<220> FEATURE:

<223> OTHER INFORMATION: anti-PD1 antibody molecule or antigen-binding
      portion HCDR3

<400> SEQUENCE: 383

Asp Tyr Gly Asn Tyr Trp Tyr Ile Asp Val
1               5                   10

<210> SEQ ID NO 384
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 384

Glu Tyr Gly Asn Tyr Trp Tyr Ile Asp Arg
1               5                   10

<210> SEQ ID NO 385
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 385

Glu Tyr Gly Asn Tyr Trp Tyr Ile Asp Val
1               5                   10

<210> SEQ ID NO 386
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 386

His Tyr Gly Asn Tyr Trp Tyr Ile Asp Val
1               5                   10

<210> SEQ ID NO 387
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 387

Ile Tyr Gly Asn Tyr Trp Tyr Ile Asp Arg
1               5                   10

<210> SEQ ID NO 388
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 388

Ile Tyr Gly Asn Tyr Trp Tyr Ile Asp Val
1               5                   10

```
<210> SEQ ID NO 389
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 389

Leu Tyr Gly Asn Tyr Trp Tyr Ile Asp Val
1               5                   10

<210> SEQ ID NO 390
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 390

Met Tyr Gly Asn Tyr Trp Tyr Ile Asp Val
1               5                   10

<210> SEQ ID NO 391
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 391

Gln Tyr Gly Asn Tyr Trp Tyr Ile Asp Arg
1               5                   10

<210> SEQ ID NO 392
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 392

Gln Tyr Gly Asn Tyr Trp Tyr Ile Asp Val
1               5                   10

<210> SEQ ID NO 393
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 393

Ser Tyr Gly Asn Tyr Trp Tyr Ile Asp Val
1               5                   10

<210> SEQ ID NO 394
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 394
```

```
Val Tyr Gly Asn Tyr Trp Tyr Ile Asp Val
1               5                   10

<210> SEQ ID NO 395
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 395

Trp Tyr Gly Asn Tyr Trp Tyr Ile Asp Val
1               5                   10

<210> SEQ ID NO 396
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion HCDR3

<400> SEQUENCE: 396

Ala Tyr Gly Asn Val Trp Tyr Ile Asp Val
1               5                   10

<210> SEQ ID NO 397
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      portion LCDR1

<400> SEQUENCE: 397

Lys Ser Ser Glu Ser Val Gly Asn Asp Leu Ala
1               5                   10

<210> SEQ ID NO 398
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      portion LCDR1

<400> SEQUENCE: 398

Lys Ser Ser Glu Ser Val Gly Asn Asp Val Ala
1               5                   10

<210> SEQ ID NO 399
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      portion LCDR1

<400> SEQUENCE: 399

Lys Ser Ser Glu Ser Val Ser Asn Asp Leu Ala
1               5                   10

<210> SEQ ID NO 400
<211> LENGTH: 7
<212> TYPE: PRT
<213> ORGANISM: Artificial Sequence
```

```
<220> FEATURE:
<223> OTHER INFORMATION: anti-PD1 antibody molecule or antigen-binding
      portion LCDR2

<400> SEQUENCE: 400

Tyr Ala Phe His Arg Glu Ser
1               5

<210> SEQ ID NO 401
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      portion LCDR2

<400> SEQUENCE: 401

Tyr Ala Phe His Arg Glu Thr
1               5

<210> SEQ ID NO 402
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      portion LCDR2

<400> SEQUENCE: 402

Tyr Ala Phe His Arg Phe Ala
1               5

<210> SEQ ID NO 403
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      portion LCDR2

<400> SEQUENCE: 403

Tyr Ala Phe His Arg Phe Ser
1               5

<210> SEQ ID NO 404
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      portion LCDR2

<400> SEQUENCE: 404

Tyr Ala Phe Pro Arg Phe Thr
1               5

<210> SEQ ID NO 405
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      portion LCDR2

<400> SEQUENCE: 405

Tyr Ala Phe Thr Arg Phe Ser
1               5
```

<210> SEQ ID NO 406
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      portion LCDR2

<400> SEQUENCE: 406

Tyr Ala Phe Thr Arg Phe Thr
1               5

<210> SEQ ID NO 407
<211> LENGTH: 9
<212> TYPE: PRT
<213> ORGANISM: Artificial Sequence
<220> FEATURE:
<223> OTHER INFORMATION: anti-PD1 antibody molecule or antigen-binding
      portion LCDR3

<400> SEQUENCE: 407

His Gln Ala Tyr Ser Asn Pro Tyr Thr
1               5

<210> SEQ ID NO 408
<211> LENGTH: 9
<212> TYPE: PRT
<213> ORGANISM: Artificial Sequence
<220> FEATURE:
<223> OTHER INFORMATION: anti-PD1 antibody molecule or antigen-binding
      portion LCDR3

<400> SEQUENCE: 408

Gln Gln Ser Tyr Ser Thr Pro Tyr Thr
1               5

<210> SEQ ID NO 409
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      portion consensus LCDR1

<400> SEQUENCE: 409

Lys Ser Ser Gln Ser Val Ser Asn Asp Val Ala
1               5                   10

<210> SEQ ID NO 410
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      portion consensus LCDR2

<400> SEQUENCE: 410

Tyr Ala Phe His Arg Phe Thr
1               5

<210> SEQ ID NO 411
<211> LENGTH: 9
<212> TYPE: PRT
<213> ORGANISM: Artificial Sequence
<220> FEATURE:
<223> OTHER INFORMATION: anti-PD1 antibody molecule or antigen-binding
      portion consensus LCDR3

```
<400> SEQUENCE: 411

His Gln Ala Tyr Ser Ser Pro Tyr Thr
1               5

<210> SEQ ID NO 412
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion consensus HCDR1

<400> SEQUENCE: 412

Gly Phe Ser Leu Thr Ser Tyr Gly Val His
1               5                   10

<210> SEQ ID NO 413
<211> LENGTH: 18
<212> TYPE: PRT
<213> ORGANISM: Artificial Sequence
<220> FEATURE:
<223> OTHER INFORMATION: anti-PD1 antibody molecule or antigen-binding
      portion consensus HCDR2

<400> SEQUENCE: 413

Leu Gly Val Ile Trp Ala Gly Gly Ser Thr Asn Tyr Asn Asp Ser Val
1               5                   10                  15

Lys Gly

<210> SEQ ID NO 414
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      portion consensus HCDR3

<400> SEQUENCE: 414

Ala Tyr Gly Asn Tyr Trp Tyr Ile Asp Val
1               5                   10

<210> SEQ ID NO 415
<211> LENGTH: 338
<212> TYPE: PRT
<213> ORGANISM: Homo sapiens

<400> SEQUENCE: 415

Met Val Arg Arg Val Gln Pro Asp Arg Lys Gln Leu Pro Leu Val Leu
1               5                   10                  15

Leu Arg Leu Leu Cys Leu Leu Pro Thr Gly Leu Pro Val Arg Ser Val
            20                  25                  30

Asp Phe Asn Arg Gly Thr Asp Asn Ile Thr Val Arg Gln Gly Asp Thr
        35                  40                  45

Ala Ile Leu Arg Cys Val Val Glu Asp Lys Asn Ser Lys Val Ala Trp
    50                  55                  60

Leu Asn Arg Ser Gly Ile Ile Phe Ala Gly His Asp Lys Trp Ser Leu
65                  70                  75                  80

Asp Pro Arg Val Glu Leu Glu Lys Arg His Ser Leu Glu Tyr Ser Leu
                85                  90                  95

Arg Ile Gln Lys Val Asp Val Tyr Asp Glu Gly Ser Tyr Thr Cys Ser
            100                 105                 110

Val Gln Thr Gln His Glu Pro Lys Thr Ser Gln Val Tyr Leu Ile Val
```

```
              115                 120                 125
Gln Val Pro Lys Ile Ser Asn Ile Ser Ser Asp Val Thr Val Asn
    130                 135                 140
Glu Gly Ser Asn Val Thr Leu Val Cys Met Ala Asn Gly Arg Pro Glu
145                 150                 155                 160
Pro Val Ile Thr Trp Arg His Leu Thr Pro Thr Gly Arg Glu Phe Glu
                165                 170                 175
Gly Glu Glu Glu Tyr Leu Glu Ile Leu Gly Ile Thr Arg Glu Gln Ser
                180                 185                 190
Gly Lys Tyr Glu Cys Lys Ala Ala Asn Glu Val Ser Ser Ala Asp Val
            195                 200                 205
Lys Gln Val Lys Val Thr Val Asn Tyr Pro Pro Thr Ile Thr Glu Ser
    210                 215                 220
Lys Ser Asn Glu Ala Thr Thr Gly Arg Gln Ala Ser Leu Lys Cys Glu
225                 230                 235                 240
Ala Ser Ala Val Pro Ala Pro Asp Phe Glu Trp Tyr Arg Asp Asp Thr
                245                 250                 255
Arg Ile Asn Ser Ala Asn Gly Leu Glu Ile Lys Ser Thr Glu Gly Gln
                260                 265                 270
Ser Ser Leu Thr Val Thr Asn Val Thr Glu Glu His Tyr Gly Asn Tyr
            275                 280                 285
Thr Cys Val Ala Ala Asn Lys Leu Gly Val Thr Asn Ala Ser Leu Val
            290                 295                 300
Leu Phe Arg Pro Gly Ser Val Arg Gly Ile Asn Gly Ser Ile Ser Leu
305                 310                 315                 320
Ala Val Pro Leu Trp Leu Leu Ala Ala Ser Leu Leu Cys Leu Leu Ser
                325                 330                 335
Lys Cys

<210> SEQ ID NO 416
<211> LENGTH: 527
<212> TYPE: PRT
<213> ORGANISM: Homo sapiens

<400> SEQUENCE: 416

Met Glu Ser Ala Ala Ala Leu His Phe Ser Arg Pro Ala Ser Leu Leu
1               5                   10                  15
Leu Leu Leu Leu Ser Leu Cys Ala Leu Val Ser Ala Gln Phe Ile Val
                20                  25                  30
Val Gly Pro Thr Asp Pro Ile Leu Ala Thr Val Gly Glu Asn Thr Thr
            35                  40                  45
Leu Arg Cys His Leu Ser Pro Glu Lys Asn Ala Glu Asp Met Glu Val
    50                  55                  60
Arg Trp Phe Arg Ser Gln Phe Ser Pro Ala Val Phe Val Tyr Lys Gly
65                  70                  75                  80
Gly Arg Glu Arg Thr Glu Glu Gln Met Glu Glu Tyr Arg Gly Arg Thr
                85                  90                  95
Thr Phe Val Ser Lys Asp Ile Ser Arg Gly Ser Val Ala Leu Val Ile
                100                 105                 110
His Asn Ile Thr Ala Gln Glu Asn Gly Thr Tyr Arg Cys Tyr Phe Gln
            115                 120                 125
Glu Gly Arg Ser Tyr Asp Glu Ala Ile Leu His Leu Val Val Ala Gly
    130                 135                 140
Leu Gly Ser Lys Pro Leu Ile Ser Met Arg Gly His Glu Asp Gly Gly
```

```
145                150                155                160
Ile Arg Leu Glu Cys Ile Ser Arg Gly Trp Tyr Pro Lys Pro Leu Thr
                165                170                175
Val Trp Arg Asp Pro Tyr Gly Val Ala Pro Ala Leu Lys Glu Val
                180                185                190
Ser Met Pro Asp Ala Asp Gly Leu Phe Met Val Thr Thr Ala Val Ile
                195                200                205
Ile Arg Asp Lys Ser Val Arg Asn Met Ser Cys Ser Ile Asn Asn Thr
    210                215                220
Leu Leu Gly Gln Lys Lys Glu Ser Val Ile Phe Ile Pro Glu Ser Phe
225                230                235                240
Met Pro Ser Val Ser Pro Cys Ala Val Ala Leu Pro Ile Ile Val Val
                245                250                255
Ile Leu Met Ile Pro Ile Ala Val Cys Ile Tyr Trp Ile Asn Lys Leu
                260                265                270
Gln Lys Glu Lys Lys Ile Leu Ser Gly Glu Lys Glu Phe Glu Arg Glu
                275                280                285
Thr Arg Glu Ile Ala Leu Lys Glu Leu Glu Lys Glu Arg Val Gln Lys
                290                295                300
Glu Glu Glu Leu Gln Val Lys Glu Lys Leu Gln Glu Leu Arg Trp
305                310                315                320
Arg Arg Thr Phe Leu His Ala Val Asp Val Val Leu Asp Pro Asp Thr
                325                330                335
Ala His Pro Asp Leu Phe Leu Ser Glu Asp Arg Arg Ser Val Arg Arg
                340                345                350
Cys Pro Phe Arg His Leu Gly Glu Ser Val Pro Asp Asn Pro Glu Arg
                355                360                365
Phe Asp Ser Gln Pro Cys Val Leu Gly Arg Glu Ser Phe Ala Ser Gly
                370                375                380
Lys His Tyr Trp Glu Val Glu Val Glu Asn Val Ile Glu Trp Thr Val
385                390                395                400
Gly Val Cys Arg Asp Ser Val Glu Arg Lys Gly Glu Val Leu Leu Ile
                405                410                415
Pro Gln Asn Gly Phe Trp Thr Leu Glu Met His Lys Gly Gln Tyr Arg
                420                425                430
Ala Val Ser Ser Pro Asp Arg Ile Leu Pro Leu Lys Glu Ser Leu Cys
                435                440                445
Arg Val Gly Val Phe Leu Asp Tyr Glu Ala Gly Asp Val Ser Phe Tyr
    450                455                460
Asn Met Arg Asp Arg Ser His Ile Tyr Thr Cys Pro Arg Ser Ala Phe
465                470                475                480
Ser Val Pro Val Arg Pro Phe Phe Arg Leu Gly Cys Glu Asp Ser Pro
                485                490                495
Ile Phe Ile Cys Pro Ala Leu Thr Gly Ala Asn Gly Val Thr Val Pro
                500                505                510
Glu Glu Gly Leu Thr Leu His Arg Val Gly Thr His Gln Ser Leu
                515                520                525
```

PD1 BINDING AGENTS

CROSS-REFERENCE TO RELATED APPLICATIONS

This application is a continuation of International Patent Application No. PCT/EP2019/055927, filed on Mar. 8, 2019, which claims the benefit of GB Patent Application No. 1813405.6, filed on Aug. 16, 2018, and GB Patent Application No. 1803746.5, filed on Mar. 8, 2018, the disclosure of each of which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ULNL_001_02US_SeqList_ST25.txt, date recorded: Jun. 25, 2020, file size ~161,113 bytes).

FIELD OF THE INVENTION

The invention relates to antibody molecules binding specifically to PD1 (also known as Programmed cell death 1, PDCD1, CD279, PD-1, SLEB2, PD-I, SLE1) and medical uses thereof.

BACKGROUND OF THE INVENTION

PD1 is a cell surface receptor that is a member of the immunoglobulin superfamily and is principally expressed on T cells, but has also been observed on pro-B cells. PD1 binds two known ligands, PD-L1 and PD-L2. The interaction of these ligands with PD1 on T cells down-regulates T cell inflammatory activity, which promotes immune self-tolerance. PD1 is, therefore, described as being an immune 'checkpoint'. This checkpoint activity has been demonstrated to minimise autoimmunity risk by promoting apoptosis (programmed cell death) in lymph node-resident T cells that are reactive to self-antigens. Importantly, PD1 ligation also promotes the survival of regulatory (anti-inflammatory) T cells.

While the role of PD1/PD-L1(2) binding in non-disease states is important for self-tolerance, it is also a key mechanism by which tumour cells escape identification as 'foreign' during immune surveillance. Indeed, PD-L1 has been shown to be highly expressed in several cancers. Monoclonal antibodies that target PD1 and antagonise its function can therefore be of significant potential value in treating cancer, by boosting the immune response against malignant cells with high PD-L1 expression and/or which exhibit high levels of mutation. A significant body of preclinical and clinical evidence suggests that blocking PD1/PD-L1 binding can enhance the anti-tumour activity of T cells and inhibit the growth of both haematological and solid malignancies. As PD1/PD-L1 activity can also be induced in chronic diseases such as HIV, anti-PD1 antagonistic antibodies may also have therapeutic value in infectious disease settings. Hence, antagonistic anti-PD1 mAbs have the potential to act as immunotherapeutic agents in cancer, immune and infectious disease settings, and to amplify the effectiveness of currently established therapies.

The majority of currently approved antibody therapeutics are derived from immunized rodents. Many of those antibodies have undergone a process known as "humanization", via the "grafting" of murine CDRs into human v-gene framework sequences (see Nelson et al., 2010, Nat Rev Drug Discov 9: 767-774). This process is often inaccurate and leads to a reduction in target binding affinity of the resulting antibody. To return the binding affinity of the original antibody, murine residues are usually introduced at key positions in the variable domain frameworks of the grafted v-domains (also known as "back-mutations").

While antibodies humanized via CDR grafting and back mutations have been shown to induce lower immune response rates in the clinic in comparison to those with fully murine v-domains, antibodies humanized using this basic grafting method still carry significant clinical development risks due to the potential physical instability and immunogenicity motifs still housed in the grafted CDR loops. Antibodies such as PD1 inhibitors that target receptors on immune cells, and whose pharmacological function is to stimulate immune responses, are at heightened risk of provoking anti-drug antibody responses. These anti-drug antibody responses in the patient can reduce drug half-life, potency and safety during clinical use. As animal testing of protein immunogenicity is often non-predictive of immune responses in man, antibody engineering for therapeutic use focuses on minimizing predicted human T-cell epitope content, non-human germline amino acid content and aggregation potential in the purified protein.

The ideal humanized, agonistic anti-PD1 antibody would therefore have as many identical residues as possible in the v-domains to those found in both the frameworks and CDRs of well-characterized human germline sequences. Townsend et al. (2015; PNAS 112: 15354-15359) describe a method for generating antibodies in which CDRs derived from rat, rabbit and mouse antibodies were grafted into preferred human frameworks and then subjected to a human germ-lining approach termed "Augmented Binary Substitution". Although the approach demonstrated a fundamental plasticity in the original antibody paratopes, even when an investigator is in possession of highly accurate antibody-antigen co-crystal structural data, it is still not possible to reliably predict which individual residues in the CDR loops of any given antibody can be converted to human germline, and in what combination. Additionally, the Townsend et al. study did not address the addition of mutagenesis beyond the residues found in the human germline at positions where the removal of development risk motifs might be beneficial. This is a technological limitation which renders the process inherently inefficient, requiring an extra stage of modification of the starting antibody sequence. In addition, it cannot currently be accurately predicted what modifications in distal positions of the protein sequence of an individual v-domain, or even on the partner v-domain, might facilitate the removal of risk motifs while maintaining antigen binding affinity and specificity.

CDR germ-lining and development quality optimisation is thus a complex, multifactorial problem, as multiple functional properties of the molecule should preferably be maintained or improved, including in this instance: target binding specificity, PD1/PD-L1 signalling antagonism, affinity to PD1 from both human and animal test species (e.g. cynomolgus monkey, also known as the crab-eating macaque, i.e. *Macaca fascicularis*) should be as similar as possible to facilitate highly accurate preclinical safety testing, v-domain biophysical stability and/or IgG expression yield should be optimal for manufacturing purposes. Antibody engineering studies have shown that mutation of even single residue positions in key CDRs can have dramatic negative effects on all of these desired molecular properties.

WO2015/035606 A1 describes an antagonistic murine anti-PD1 IgG molecule termed "Mu317", and also the preparation of humanized forms of Mu317 (designated hu317). Those humanized forms of Mu317 were produced using classical humanization techniques, i.e. by grafting of Kabat-defined murine CDRs into human heavy and light chain framework sequences, with some of the human framework residues being potentially back-mutated to the correspondingly positioned Mu317 murine residues. For reasons noted above, such humanized forms of Mu317 described in WO2015/035606 A1 are not ideal.

SUMMARY OF THE INVENTION

The present invention provides a number of anti-PD1 antibodies and medical uses thereof.

According to one aspect of the invention, there is provided an antibody molecule which specifically binds to human PD1, and optionally also to cynomolgus monkey PD1, or an antigen-binding portion thereof, wherein the antibody molecule or antigen-binding portion comprises a heavy chain variable region with:

an HCDR1 having amino acids in sequence in the following order: G-F-T or a conservative substitution of T (for example S)-F or a conservative substitution of F (for example L)-S or a conservative substitution of S (for example T)-S-Y-G or any amino acid (for example W)-M or a conservative substitution of M (for example V)-S or any amino acid (for example H) (SEQ ID NO:20);

an HCDR2 having amino acids in sequence in the following order: V or a conservative substitution of V (for example L)-A or a conservative substitution of A (for example G)-V/N-I-W/K-Q/A-D/G-G-S-T/E-N/K/S-Y-N/V-D-S-V-K-G (SEQ ID NO:21); and an HCDR3 having amino acids in sequence in the following order: A or any amino acid (for example D/E/G/H/I/K/L/H/Q/S/V/W)-Y or a conservative substitution of Y (for example F/W)-G-N or any amino acid (for example A/E/F/G/H/I/Q/R/S/T/V/W/Y)-Y or a conservative substitution of Y (for example V/W)-W or any amino acid (for example F/H/M/P/Q/S/V)-Y-I or any amino acid (for example L/M/S/T/V/Y)-D or a conservative substitution of D (for example E)-V or any amino acid (for example A/E/F/G/H/I/K/L/M/R/S/T/W/Y) (SEQ ID NO:22).

In aspects of the invention, the HCDR1 of the antibody molecule or antigen-binding portion may exclude the sequences GFSLTSYGVH (SEQ ID NO:23; Mu317 murine/humanized antibody HCDR1 disclosed in WO2015/035606 A1; US2015/079109A1), VIWAGGSTNYNSALMS (SEQ ID NO:24; Mu317 murine/humanized antibody HCDR2 disclosed in WO2015/035606 A1; US2015/079109A1), and/or the HCDR3 of the antibody molecule or antigen-binding portion may exclude the sequence AYGNYWYIDV (SEQ ID NO:25; Mu317 murine/humanized antibody HCDR3 disclosed in WO2015/035606 A1; US2015/079109A1).

The antibody molecule or antigen-binding portion may further comprise a light chain variable region with:

an LCDR1 having amino acids in sequence in the following order: K-S-S-Q/E-S-V-S or a conservative substitution of S (such as G/T)-N-D-L or a conservative substitution of L (such as V)-A (SEQ ID NO:26);

an LCDR2 having amino acids in sequence in the following order: Y-A-F or any amino acid (for example S)-H or any amino acid (for example P/T)-R-F-S or a conservative substitution of S (such as NT) (SEQ ID NO:27); and an LCDR3 having amino acids in sequence in the following order: Q or any amino acid (for example H)-Q-A or any amino acid (for example S)-Y-S-T or any amino acid (for example, N/S)-P-Y or any amino acid (for example W)-T (SEQ ID NO:28).

In aspects of the invention, the LCDR1 of the antibody molecule or antigen-binding portion may exclude the sequence KASQSVSNDVA/KSSQEVSNDVA (SEQ ID NO:29/SEQ ID NO:30; Mu317 murine/humanized antibody LCDR1 disclosed in WO2015/035606 A1; US2015/079109A1), and/or the LCDR2 of the antibody molecule or antigen-binding portion may exclude the sequence YAFHRFT (SEQ ID NO:31; Mu317 murine/humanized antibody LCDR2 disclosed in WO2015/035606 A1; US2015/079109A1) and/or the LCDR3 of the antibody molecule or antigen-binding portion may exclude the sequence HQAYSSPYT (SEQ ID NO:32; Mu317 murine/humanized antibody LCDR3 disclosed in WO2015/035606 A1; US2015/079109A1).

In some aspects, disclosed herein is an anti-PD1 antibody or an antigen-binding portion thereof, wherein the antibody comprises a heavy chain variable (VH) region comprising HCDR1, HCDR2, and HCDR3 and a light chain variable (VL) region comprising LCDR1, LCDR2, and LCDR3, wherein (a) the HCDR1 comprises the amino acid sequence G-F-$X_1$-$X_2$-$X_3$-S-Y-$X_4$-$X_5$-$X_6$, wherein $X_1$ is T or a conservative substitution of T, $X_2$ is F or a conservative substitution of F, $X_3$ is S or a conservative substitution of S, $X_4$ is G or any other amino acid, $X_5$ is M or a conservative substitution of M, and $X_6$ is S or any other amino acid (SEQ ID NO:20);

(b) the HCDR2 comprises the amino acid sequence $X_1$-$X_2$-$X_3$-I-$X_4$-$X_5$-$X_6$-G-S-$X_7$-$X_8$-Y-$X_9$-D-S-V-K-G, wherein $X_1$ is V or a conservative substitution of V, $X_2$ is A or a conservative substitution of A, $X_3$ is V or N, $X_4$ is W or K, $X_5$ is Q or A, $X_6$ is D or G, $X_7$ is T or E, $X_8$ is N, K, or S, and $X_9$ is N or V (SEQ ID NO:21);

(c) the HCDR3 comprises the amino acid sequence $X_1$-$X_2$-G-$X_3$-$X_4$-$X_5$-Y-$X_6$-$X_7$-$X_8$, wherein $X_1$ is A or any other amino acid, $X_2$ is Y or a conservative substitution of Y, $X_3$ is N or any other amino acid, $X_4$ is Y or a conservative substitution of Y, $X_5$ is W or any other amino acid, $X_6$ is I or any other amino acid, $X_7$ is D or a conservative substitution of D, and $X_8$ is V or any other amino acid (SEQ ID NO:22);

(d) the LCDR1 comprises the amino acid sequence K-S-S-$X_1$-S-V-$X_2$-N-D-$X_3$-A, wherein $X_1$ is Q or E, $X_2$ is S or a conservative substitution of S, and $X_3$ is L or a conservative substitution of L (SEQ ID NO:26);

(e) the LCDR2 comprises the amino acid sequence Y-A-$X_1$-$X_2$-R-F-$X_3$, wherein $X_1$ is F or any other amino acid, $X_2$ is H or any other amino acid, and $X_3$ is S or a conservative substitution of S (SEQ ID NO:27); and (f) the LCDR3 comprises the amino acid sequence $X_1$-Q-$X_2$-Y-S-$X_3$-P-$X_4$-T, wherein $X_1$ is Q or any other amino acid, $X_2$ is A or any other amino acid, $X_3$ is T or any other amino acid, and $X_4$ is Y or any other amino acid (SEQ ID NO:28).

In some aspects, the invention provides an anti-PD1 antibody or an antigen-binding portion thereof, wherein the antibody comprises a heavy chain variable (VH) region and a light chain variable (VL) region, wherein (a) the VH region amino acid sequence comprises HCDR1 of GFTFSSYGMS (SEQ ID NO:33), HCDR2 of VANIWQDGSTKYVDSVKG (SEQ ID NO:34), and HCDR3 of AYGNYWYIDR (SEQ ID NO:35); and the VL region amino acid sequence comprises LCDR1 of KSSQS- VTNDVA (SEQ ID NO:36), LCDR2 of YAYHRFT (SEQ ID NO:37), and LCDR3 of HQAYSSPYT (SEQ ID NO:38);

(b) the VH region amino acid sequence comprises HCDR1 of GFSLSSYGMS (SEQ ID NO:39), HCDR2 of VAVIWQDGSTNYVDSVKG (SEQ ID NO:40), and HCDR3 of AYGNYWYIDR (SEQ ID NO:35); and the VL region amino acid sequence comprises LCDR1 of KSSQS-VTNDVA (SEQ ID NO:36), LCDR2 of YAYHRFT (SEQ ID NO:37), and LCDR3 of HQAYSSPYT (SEQ ID NO:38);

(c) the VH region amino acid sequence comprises HCDR1 of GFTFSSYGMS (SEQ ID NO:33), HCDR2 of VANIWQDGSEKYVDSVKG (SEQ ID NO:41), and HCDR3 of AYGNYWYIDR (SEQ ID NO:35); and the VL region amino acid sequence comprises LCDR1 of KSSQS-VTNDVA (SEQ ID NO:36), LCDR2 of YAYHRFT (SEQ ID NO:37), and LCDR3 of HQAYSSPYT (SEQ ID NO:38);

(d) the VH region amino acid sequence comprises HCDR1 of GFSFSSYGMH (SEQ ID NO:42), HCDR2 of VANIWQDGSTNYVDSVKG (SEQ ID NO:43), and HCDR3 of AYGNYWYIDR (SEQ ID NO:35); and the VL region amino acid sequence comprises LCDR1 of KSSQS-VSNDVA (SEQ ID NO:44), LCDR2 of YASHRFT (SEQ ID NO:45), and LCDR3 of HQAYSTPYT (SEQ ID NO:46);

(e) the VH region amino acid sequence comprises HCDR1 of GFSFTSYGMS (SEQ ID NO:47), HCDR2 of LANIWQDGSTNYVDSVKG (SEQ ID NO:48), and HCDR3 of AYGNYWYIDR (SEQ ID NO:35); and the VL region amino acid sequence comprises LCDR1 of KSSQS-VSNDVA (SEQ ID NO:44), LCDR2 of YASHRFT (SEQ ID NO:45), and LCDR3 of HQAYSTPYT (SEQ ID NO:46);

(f) the VH region amino acid sequence comprises HCDR1 of GFTFSSYGVH (SEQ ID NO:49), HCDR2 of VGVIWQDGSENYVDSVKG (SEQ ID NO:50), and HCDR3 of AYGNYWYIDR (SEQ ID NO:35); and the VL region amino acid sequence comprises LCDR1 of KSSQS-VSNDLA (SEQ ID NO:51), LCDR2 of YASHRFT (SEQ ID NO:45), and LCDR3 of QQAYSTPYT (SEQ ID NO:52);

(g) the VH region amino acid sequence comprises HCDR1 of GFSFSSYGMH (SEQ ID NO:42), HCDR2 of VANIWQDGSTNYVDSVKG (SEQ ID NO:43), and HCDR3 of AYGNYWYIDR (SEQ ID NO:35); and the VL region amino acid sequence comprises LCDR1 of KSSQS-VSNDVA (SEQ ID NO:44), LCDR2 of YASHRFT (SEQ ID NO:45), and LCDR3 of HQAYSTPYT (SEQ ID NO:46);

(h) the VH region amino acid sequence comprises HCDR1 of GFSFSSYGMH (SEQ ID NO:42), HCDR2 of LANIWQDGSENYVDSVKG (SEQ ID NO:53), and HCDR3 of AYGNYWYIDR (SEQ ID NO:35); and the VL region amino acid sequence comprises LCDR1 of KSSQS-VSNDVA (SEQ ID NO:44), LCDR2 of YASHRFT (SEQ ID NO:45), and LCDR3 of QQAYSTPYT (SEQ ID NO:52);

(i) the VH region amino acid sequence comprises HCDR1 of GFTLSSYGMH (SEQ ID NO: 54), HCDR2 of LAVIWADGSTNYVDSVKG (SEQ ID NO:55), and HCDR3 of AYGNYMYIDV (SEQ ID NO:56); and the VL region amino acid sequence comprises LCDR1 of KSSQS-VSNDVA (SEQ ID NO:44), LCDR2 of YASHRFT (SEQ ID NO:45), and LCDR3 of HQAYSTPYT (SEQ ID NO:46);

(j) the VH region amino acid sequence comprises HCDR1 of GFTFSSYGMH (SEQ ID NO:57), HCDR2 of VGVIKQDGSENYVDSVKG (SEQ ID NO:58), and HCDR3 of AYGNYWYIDR (SEQ ID NO:35); and the VL region amino acid sequence comprises LCDR1 of KSSQS-VSNDVA (SEQ ID NO:44), LCDR2 of YASHRFT (SEQ ID NO:45), and LCDR3 of HQAYSTPYT (SEQ ID NO:46); or (k) the VH region amino acid sequence comprises HCDR1 of GFSFTSYGMH (SEQ ID NO:59), HCDR2 of VGVIWQDGSTNYVDSVKG (SEQ ID NO:60), and HCDR3 of GYGNYWYIDV (SEQ ID NO:61); and the VL region amino acid sequence comprises LCDR1 of KSSQS-VSNDLA (SEQ ID NO:51), LCDR2 of YASHRFT (SEQ ID NO:45), and LCDR3 of QQAYSTPYT (SEQ ID NO:52).

In some aspects, disclosed herein is an anti-PD1 antibody or an antigen-binding portion thereof, wherein the antibody comprises a heavy chain variable (VH) region and a light chain variable (VL) region, wherein
the VH region amino acid sequence comprises:
(a) HCDR1 of SEQ ID NO: 33, SEQ ID NO: 39, SEQ ID NO: 42, SEQ ID NO: 47, SEQ ID NO: 49, SEQ ID NO: 54, SEQ ID NO: 57 or SEQ ID NO: 59;
(b) HCDR2 of SEQ ID NO: 34, SEQ ID NO: 40, SEQ ID NO: 41, SEQ ID NO: 43, SEQ ID NO: 48, SEQ ID NO: 50, SEQ ID NO: 53, SEQ ID NO: 55, SEQ ID NO: 58 or SEQ ID NO: 60; and
(c) HCDR3 of SEQ ID NO: 35, SEQ ID NO: 56 or SEQ ID NO: 61; and
the VL region amino acid sequence comprises:
(a') LCDR1 of SEQ ID NO: 36, SEQ ID NO: 44 or SEQ ID NO: 51;
(b') LCDR2 of SEQ ID NO: 37 or SEQ ID NO: 45; and
(c') LCDR3 of SEQ ID NO: 38, SEQ ID NO: 46 or SEQ ID NO: 52.

In some aspects, the invention provides an anti-PD1 antibody or an antigen-binding portion thereof, wherein the antibody comprises a heavy chain variable (VH) region and a light chain variable (VL) region, wherein
(a) the VH region amino acid sequence comprises SEQ ID NO:1 and the VL region amino acid sequence comprises SEQ ID NO:2;
(b) the VH region amino acid sequence comprises SEQ ID NO:3 and the VL region amino acid sequence comprises SEQ ID NO:4;
(c) the VH region amino acid sequence comprises SEQ ID NO:5 and the VL region amino acid sequence comprises SEQ ID NO:6; or
(d) the VH region amino acid sequence comprises SEQ ID NO:7 and the VL region amino acid sequence comprises SEQ ID NO:8.

Also provided according to the invention is an immunoconjugate comprising the antibody molecule or antigen-binding portion thereof as defined herein linked, fused or conjugated to a therapeutic agent.

In another aspect the invention provides a nucleic acid molecule encoding the antibody molecule or antigen-binding portion thereof as defined herein.

Further provided is a vector comprising the nucleic acid molecule of the invention.

Also provided is a host cell comprising the nucleic acid molecule or the vector of the invention as defined herein.

In a further aspect there is provided a method of producing an anti-PD1 antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the nucleic acid molecule of the invention as defined herein, or the vector of the invention as defined herein.

Further provided is a method for enhancing an immune response in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

In a further aspect there is provided a method for treating or preventing cancer in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

Further provided herein is an antibody molecule or antigen-binding portion thereof as defined herein, or the immunoconjugate as defined herein, or the nucleic acid molecule as defined herein, or the vector as defined herein, or the pharmaceutical composition as defined herein, for use as a medicament. The invention also provides an antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein, for use in the treatment of cancer.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination combined with a second therapeutic agent, for example an anti-cancer agent.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The invention also provides a method for treating or preventing an infectious disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

The infectious disease may be selected in all aspects from the group consisting of: viral, bacterial, fungal or parasitic. In one embodiment, the infectious disease is human immunodeficiency virus (HIV) infection.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of an infectious disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an infectious disease.

The invention also provides a method for treating or preventing an infectious disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

The invention also provides a method of producing an antibody molecule which specifically binds to human PD1 and optionally also to cynomolgus monkey PD1, or an antigen-binding portion thereof, comprising the steps of:

(1) grafting anti-PD1 CDRs from a non-human source into a human v-domain framework to produce a humanized anti-PD1 antibody molecule or antigen-binding portion thereof;

(2) generating a library of clones of the humanized anti-PD1 antibody molecule or antigen-binding portion thereof comprising one or more mutations in the CDRs;

(3) screening the library for binding to human PD1 and optionally also to cynomolgus monkey PD1;

(4) selecting clones from the screening step (3) having binding specificity to human PD1 and optionally also to cynomolgus monkey PD1; and (5) producing an antibody molecule which specifically binds to human PD1 and optionally also to cynomolgus monkey PD1, or an antigen-binding portion thereof from clones selected from step (4).

The method may comprise a further step of producing additional clones based on the clones selected in step (4), for example based on further exploratory mutagenesis at specific positions in the CDRs of the clones selected in step (4), to enhance humanization and/or minimise human T cell epitope content and/or improve manufacturing properties in the antibody molecule or antigen-binding portion thereof produced in step (5).

DETAILED DESCRIPTION OF THE INVENTION

Figure 1A:
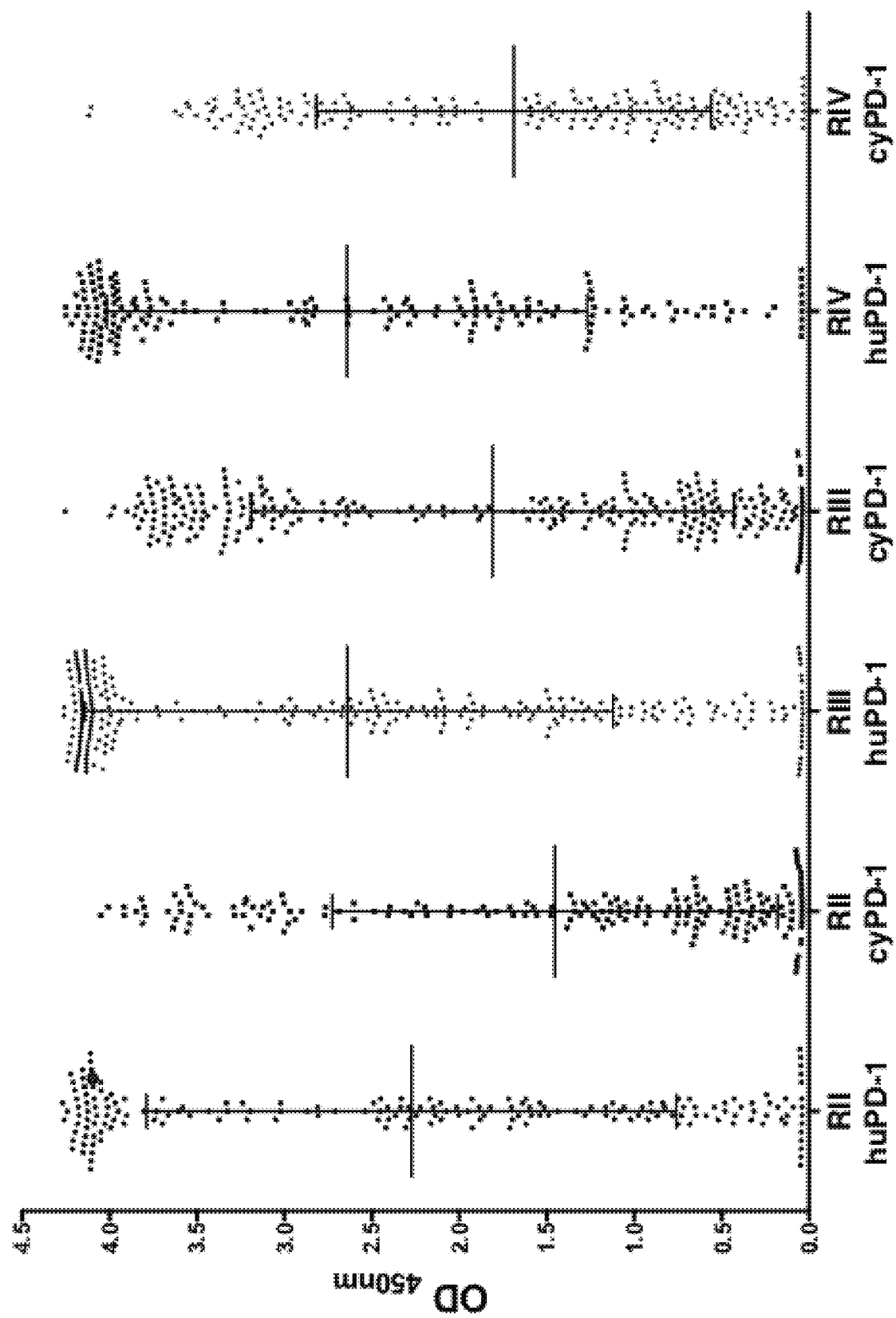
FIG. 1A-FIG. 1B. Direct binding ELISA of library-derived anti-PD1 Fabs against human and cyno PD1-Fc proteins and HTRF competition assay. Clones were derived from multiple phage selection branches where phage populations were selected on biotinylated human, or cynomolgus monkey PD1 proteins in each round. Standard selections are numbered RI-RIV. After each round of selection, library-derived clones were screened as periplasmically-expressed Fab proteins in ELISA (FIG. 1A) against both human (huPD1) and cyno (cyPD1). Fab samples were also tested in parallel for their ability to compete for the binding epitope of mu317 on human PD1 by HTRF (FIG. 1B). Mean±SD values in each round are represented in grey bars.

According to a first aspect of the invention, there is provided an antibody molecule which specifically binds to human PD1 and also to cynomolgus monkey PD1, or an antigen-binding portion thereof, wherein the antibody molecule or antigen-binding portion comprises a heavy chain variable region with:

an HCDR1 having amino acids in sequence in the following order: G-F-T or a conservative substitution of T (for example S)-F or a conservative substitution of F (for example L)-S or a conservative substitution of S (for example T)-S-Y-G or any amino acid (for example W)-M or a conservative substitution of M (for example V)-S or any amino acid (for example H) (SEQ ID NO:20);

an HCDR2 having amino acids in sequence in the following order: V or a conservative substitution of V (for example L)-A or a conservative substitution of A (for example G)-V/N-I-W/K-Q/A-D/G-G-S-T/E-N/K/S-Y-N/V-D-S-V-K-G (SEQ ID NO:21); and an HCDR3 having amino acids in sequence in the following order: A or any amino acid (for example D/E/G/H/I/K/L/H/Q/S/V/W)-Y or a conservative substitution of Y (for example F/W)-G-N or any amino acid (for example A/E/F/G/H/I/Q/R/S/T/V/W/Y)-Y or a conservative substitution of Y (for example V/W)-W or any amino acid (for example F/H/M/P/Q/S/V)-Y-I or any amino acid (for example L/M/S/T/V/Y)-D or a conservative substitution of D (for example E)-V or any amino acid (for example A/E/F/G/H/I/K/L/M/R/S/T/W/Y) (SEQ ID NO:22).

In some aspects an anti-PD1 antibody or antigen-binding portion provided herein specifically binds to a PD1 protein comprising or consisting of SEQ ID NO:16 or SEQ ID NO:17. In some aspects an anti-PD1 antibody or antigen-binding portion provided herein specifically binds to a PD1 protein having an amino acid sequence that is at least about 90%, at least about 91%, at least about 92%, at least about 93%, at least about 94%, at least about 95%, at least about 96%, at least about 97%, at least about 98% or at least about 99% identical to SEQ ID NO:16 or SEQ ID NO:17.

In aspects of the invention, the HCDR1 of the antibody molecule or antigen-binding portion may exclude the sequences GFSLTSYGVH (SEQ ID NO:23; Mu317 murine/humanized antibody HCDR1 disclosed in WO2015/035606 A1; US2015/079109A1), VIWAGGSTNYNSALMS (SEQ ID NO:24; Mu317 murine/humanized antibody HCDR2 disclosed in WO2015/035606 A1; US2015/079109A1), and/or the HCDR3 of the antibody molecule or antigen-binding portion may exclude the sequence AYGNYWYIDV (SEQ ID NO:25; Mu317 murine/humanized antibody HCDR3 disclosed in WO2015/035606 A1; US2015/079109A1).

The antibody molecule or antigen-binding portion thereof according to the invention may further comprise a light chain variable region with:

an LCDR1 having amino acids in sequence in the following order: K-S-S-Q/E-S-V-S or a conservative substitution of S (such as G/T)-N-D-L or a conservative substitution of L (such as V)-A (SEQ ID NO:26);

an LCDR2 having amino acids in sequence in the following order: Y-A-F or any amino acid (for example S/Y)-H or any amino acid (for example P/T)-R-F-S or a conservative substitution of S (such as NT) (SEQ ID NO:27); and an LCDR3 having amino acids in sequence in the following order: Q or any amino acid (for example H)-Q-A or any amino acid (for example S)-Y-S-T or any amino acid (for example, N/S)-P-Y or any amino acid (for example W)-T (SEQ ID NO:28).

In aspects of the invention, the LCDR1 of the antibody molecule or antigen-binding portion may exclude the sequence KASQSVSNDVA/KSSQEVSNDVA (SEQ ID NO:29/SEQ ID NO:30; Mu317 murine/humanized antibody LCDR1 disclosed in WO2015/035606 A1; US2015/

079109A1), and/or the LCDR2 of the antibody molecule or antigen-binding portion may exclude the sequence YAF-HRFT (SEQ ID NO:31; Mu317 murine/humanized antibody LCDR2 disclosed in WO2015/035606 A1; US2015/079109A1) and/or the LCDR3 of the antibody molecule or antigen-binding portion may exclude the sequence HQAY-SSPYT (SEQ ID NO:32; Mu317 murine/humanized antibody LCDR3 disclosed in WO2015/035606 A1; US2015/079109A1).

In some aspects, disclosed herein is an anti-PD1 antibody or an antigen-binding portion thereof, wherein the antibody comprises a heavy chain variable (VH) region comprising HCDR1, HCDR2, and HCDR3 and a light chain variable (VL) region comprising LCDR1, LCDR2, and LCDR3, wherein (a) the HCDR1 comprises the amino acid sequence G-F-$X_1$-$X_2$-$X_3$-S-Y-$X_4$-$X_5$-$X_6$, wherein $X_1$ is T or a conservative substitution of T (for example, S), $X_2$ is F or a conservative substitution of F (for example, L), $X_3$ is S or a conservative substitution of S (for example, T), $X_4$ is G or any other amino acid (for example, W), $X_5$ is M or a conservative substitution of M (for example, V), and $X_6$ is S or any other amino acid (for example, H) (SEQ ID NO:20);

(b) the HCDR2 comprises the amino acid sequence $X_1$-$X_2$-$X_3$-I-$X_4$-$X_5$-$X_6$-G-S-$X_7$-$X_8$-Y-$X_9$-D-S-V-K-G, wherein $X_1$ is V or a conservative substitution of V (for example, L), $X_2$ is A or a conservative substitution of A (for example, G), $X_3$ is V or N, $X_4$ is W or K, $X_5$ is Q or A, $X_6$ is D or G, $X_7$ is T or E, $X_8$ is N, K, or S, and $X_9$ is N or V (SEQ ID NO:21);

(c) the HCDR3 comprises the amino acid sequence $X_1$-$X_2$-G-$X_3$-$X_4$-$X_5$-Y-$X_6$-$X_7$-$X_8$, wherein $X_1$ is A or any other amino acid (for example, D, E, G, H, I, K, L, H, Q, S, V, or W), $X_2$ is Y or a conservative substitution of Y (for example, F or W), $X_3$ is N or any other amino acid (for example, A, E, F, G, H, I, Q, R, S, T, V, W, or Y), $X_4$ is Y or a conservative substitution of Y (for example, V or W), $X_5$ is W or any other amino acid (for example, F, H, M, P, Q, S, or V), $X_6$ is I or any other amino acid (for example, L, M, S, T, V, or Y), $X_7$ is D or a conservative substitution of D (for example, E), and $X_8$ is V or any other amino acid (for example, A, E, F, G, H, I, K, L, M, R, S, T, W, or Y) (SEQ ID NO:22);

(d) the LCDR1 comprises the amino acid sequence K-S-S-$X_1$-S-V-$X_2$-N-D-$X_3$-A, wherein $X_1$ is Q or E, $X_2$ is S or a conservative substitution of S (for example, G or T), and $X_3$ is L or a conservative substitution of L (for example, V) (SEQ ID NO:26);

(e) the LCDR2 comprises the amino acid sequence Y-A-$X_1$-$X_2$-R-F-$X_3$, wherein $X_1$ is F or any other amino acid (for example, S), $X_2$ is H or any other amino acid (for example, P or T), and $X_3$ is S or a conservative substitution of S (for example, A or T) (SEQ ID NO:27); and (f) the LCDR3 comprises the amino acid sequence $X_1$-Q-$X_2$-Y-S-$X_3$-P-$X_4$-T, wherein $X_1$ is Q or any other amino acid (for example, H), $X_2$ is A or any other amino acid (for example, S), $X_3$ is T or any other amino acid (for example, N or S), and $X_4$ is Y or any other amino acid (for example, W) (SEQ ID NO:28).

In some aspects, disclosed herein is an anti-PD1 antibody or an antigen-binding portion thereof, wherein the antibody comprises a heavy chain variable (VH) region comprising, in amino-terminal to carboxyl-terminal order, FR1-HCDR1-FR2-HCDR2-FR3-HCDR3-FR4 and a light chain variable (VL) region comprising, in amino-terminal to carboxyl-terminal order, FR1-LCDR1-FR2-LCDR2-FR3-LCDR3-FR4, wherein the HCDR1 is SEQ ID NO:20, the HCDR2 is SEQ ID NO:32, the HCDR3 is SEQ ID NO:33, the LCDR1 is SEQ ID NO:26, the LCDR2 is SEQ ID NO:27 and the LCDR3 is SEQ ID NO:28, wherein the heavy chain FR1, FR2, FR3 and FR4 amino acid sequences are the heavy chain FR1, FR2, FR3 and FR4 amino acid sequences in SEQ ID NO: 116 (see Table 2) and wherein the light chain FR1, FR2, FR3 and FR4 amino acid sequences are the light chain FR1, FR2, FR3 and FR4 amino acid sequences in SEQ ID NO: 119 (see Table 2).

As elaborated herein, the present inventors have succeeded for the first time in generating a number of optimized anti-PD1 antibody molecules using CDR sequences derived from the murine anti-PD1 antibody Mu317 disclosed in WO2015/035606 A1; US2015/079109A1. Refining of the optimized antibody molecules as described herein has provided improved variable domain stability, high expression yields, and/or reduced immunogenicity potential without compromising binding specificity to both human PD1 as well as cynomolgus monkey PD1 (to facilitate maximally accurate primate toxicology and pk studies) and pharmacological potency in PD1 antagonism assays.

In some aspects, optimized anti-PD1 antibody molecules of the present invention do not necessarily have the maximum number of human germline substitutions at corresponding murine CDR or other (such as framework) amino acid positions. As elaborated in the experimental section below, we have found that "maximally humanized" antibody molecules are not necessary "maximally optimized" in terms of anti-PD1 binding characteristics and/or other desirable features.

The present invention encompasses modifications to the amino acid sequence of the antibody molecule or antigen-binding portion thereof as defined herein. For example, the invention includes antibody molecules and corresponding antigen-binding portions thereof comprising functionally equivalent variable regions and CDRs which do not significantly affect their properties as well as variants which have enhanced or decreased activity and/or affinity. For example, the amino acid sequence may be mutated to obtain an antibody with the desired binding affinity to PD1. Insertions which include amino- and/or carboxyl-terminal fusions ranging in length from one residue to polypeptides containing a hundred or more residues, as well as intrasequence insertions of single or multiple amino acid residues, are envisaged. Examples of terminal insertions include an antibody molecule with an N-terminal methionyl residue or the antibody molecule fused to an epitope tag. Other insertional variants of the antibody molecule include the fusion to the N- or C-terminus of the antibody of an enzyme or a polypeptide which increases the half-life of the antibody in the blood circulation.

The antibody molecule or antigen-binding portion of the invention may include glycosylated and nonglycosylated polypeptides, as well as polypeptides with other post-translational modifications, such as, for example, glycosylation with different sugars, acetylation, and phosphorylation. The antibody molecule or antigen-binding portion of the invention may be mutated to alter such post-translational modifications, for example by adding, removing or replacing one or more amino acid residues to form or remove a glycosylation site.

The antibody molecule or antigen-binding portion of the invention may be modified for example by amino acid substitution to remove potential proteolytic sites in the antibody.

In the antibody molecule or antigen-binding portion thereof, the HCDR1 may have the amino acid sequence: G-F-T-F-S-S-Y-G-MN-S/H (SEQ ID NO:62); the HCDR2 may have the amino acid sequence: V-A-V/N-I-W/K-Q-D-G-S-E/T-N/K-Y-V/N-D-S-V-K-G (SEQ ID NO:63); and the HCDR3 may have the amino acid sequence: A/D/E/G/H/I/K/L/H/Q/S/V/W-Y/F/W-G-N/NE/F/G/H/I/Q/R/S/T/V/W/Y-Y/V/W-W/F/H/M/P/Q/S/V-Y-I/L/M/S/T/V/Y-D/E-V/A/E/F/G/H/I/Q/R/S/T/W/Y (SEQ ID NO:64).

For example, the HCDR1 may have the amino acid sequence: G-F-T-F-S-S-Y-G-M-S/H (SEQ ID NO:65); the HCDR2 may have the amino acid sequence: V-A-V/N-I-W-Q-D-G-S-E/T-N/K-Y-V-D-S-V-K-G (SEQ ID NO:66); and the HCDR3 may have the amino acid sequence: A/G-Y-G-N-Y-W/M-Y-I-D-R/V (SEQ ID NO:67).

In the antibody molecule or antigen-binding portion thereof, the LCDR1 may have the amino acid sequence: K-S-S-Q/E-S-V-S/G/T-N-D-L/V-A (SEQ ID NO:68); the LCDR2 may have the amino acid sequence Y-A-F/S/Y-H/P/T-R-F-S/T (SEQ ID NO:69); and the LCDR3 may have the amino acid sequence: Q/H-Q-A/S-Y-S-T/N/S-P-Y-T (SEQ ID NO:70).

For example, the LCDR1 may have the amino acid sequence: K-S-S-Q-S-V-S/G/T-N-D-L/V-A (SEQ ID NO:71); the LCDR2 may have the amino acid sequence Y-A-S/Y-H-R-F-S/T (SEQ ID NO:72); and the LCDR3 may have the amino acid sequence: Q/H-Q-A-Y-S-T/S-P-Y-T (SEQ ID NO:73).

In specific embodiments of the invention, the antibody molecule or antigen-binding portion may comprise:

(a) the amino acid sequences
GFSFTSYGMS (SEQ ID NO:47; HCDR1), LANIWQDGSTNYVDSVKG (SEQ ID NO:48; HCDR2), AYGNYWYIDR (SEQ ID NO:35; HCDR3), KSSQSVSNDVA (SEQ ID NO:44; LCDR1), YASHRFT (SEQ ID NO:45; LCDR2) and HQAYSTPYT (SEQ ID NO:46; LCDR3) [Clone 20007]; or (b) the amino acid sequences
GFTFSSYGVH (SEQ ID NO:49; HCDR1), VGVIWQDGSENYVDSVKG (SEQ ID NO:50; HCDR2), AYGNYWYIDR (SEQ ID NO:35; HCDR3), KSSQSVSNDLA (SEQ ID NO:51; LCDR1), YASHRFT (SEQ ID NO:45; LCDR2) and QQAYSTPYT (SEQ ID NO:52; LCDR3) [Clone 11C08];

(c) the amino acid sequences
GFSFSSYGMH (SEQ ID NO:42; HCDR1), VANIWQDGSTNYVDSVKG (SEQ ID NO:43; HCDR2), AYGNYWYIDR (SEQ ID NO:35; HCDR3), KSSQSVSNDVA (SEQ ID NO:44; LCDR1), YASHRFT (SEQ ID NO:45; LCDR2) and HQAYSTPYT (SEQ ID NO:46; LCDR3) [Clone 09C06];

(d) the amino acid sequences
GFSFSSYGMH (SEQ ID NO:42; HCDR1), LANIWQDGSENYVDSVKG (SEQ ID NO:53; HCDR2), AYGNYWYIDR (SEQ ID NO:35; HCDR3), KSSQSVSNDVA (SEQ ID NO:44; LCDR1), YASHRFT (SEQ ID NO:45; LCDR2) and QQAYSTPYT (SEQ ID NO:52; LCDR3) [Clone 17A12];

(e) the amino acid sequences
GFTLSSYGMH (SEQ ID NO:54; HCDR1), LAVIWADGSTNYVDSVKG (SEQ ID NO:55; HCDR2), AYGNYMYIDV (SEQ ID NO:56; HCDR3), KSSQSVSNDVA (SEQ ID NO:44; LCDR1), YASHRFT (SEQ ID NO:45; LCDR2) and HQAYSTPYT (SEQ ID NO:46; LCDR3) [Clone 17D08];

(f) the amino acid sequences
GFTFSSYGMH (SEQ ID NO:57; HCDR1), VGVIKQDGSENYVDSVKG (SEQ ID NO:58; HCDR2), AYGNYWYIDR (SEQ ID NO:35; HCDR3), KSSQSVSNDVA (SEQ ID NO:44; LCDR1), YASHRFT (SEQ ID NO:45; LCDR2) and HQAYSTPYT (SEQ ID NO:46; LCDR3) [Clone 17G08];

(g) the amino acid sequences
GFSFTSYGMH (SEQ ID NO:59; HCDR1), VGVIWQDGSTNYVDSVKG (SEQ ID NO:60; HCDR2), GYGNYWYIDV (SEQ ID NO:61; HCDR3), KSSQSVSNDLA (SEQ ID NO:51; LCDR1), YASHRFT (SEQ ID NO:45; LCDR2) and QQAYSTPYT (SEQ ID NO:52; LCDR3) [Clone 15D07];

(h) the amino acid sequences
GFSLSSYGMS (SEQ ID NO:39; HCDR1), VAVIWQDGSTNYVDSVKG (SEQ ID NO:40; HCDR2), AYGNYWYIDR (SEQ ID NO:35; HCDR3), KSSQSVGNDVA (SEQ ID NO:74; LCDR1), YASHRFT (SEQ ID NO:45; LCDR2) and QQAYSSPYT (SEQ ID NO:75; LCDR3) [Clone MH1];

(i) the amino acid sequences
GFSLSSYGMS (SEQ ID NO:39; HCDR1), VAVIWQDGSTNYVDSVKG (SEQ ID NO:40; HCDR2), AYGNYWYIDR (SEQ ID NO:35; HCDR3), KSSQSVTNDLA (SEQ ID NO:76; LCDR1), YASHRFT (SEQ ID NO:45; LCDR2) and QQAYSSPYT (SEQ ID NO:75; LCDR3) [Clone MH2];

(j) the amino acid sequences
GFSLSSYGMS (SEQ ID NO:39; HCDR1), VAVIWQDGSTNYVDSVKG (SEQ ID NO:40; HCDR2), AYGNYWYIDR (SEQ ID NO:35; HCDR3), KSSQSVGNDLA (SEQ ID NO:77; LCDR1), YAYHRFS (SEQ ID NO:78; LCDR2) and QQAYSSPYT (SEQ ID NO:75; LCDR3) [Clone MH3];

(k) the amino acid sequences
GFSLSSYGMS (SEQ ID NO:39; HCDR1), VAVIWQDGSTNYVDSVKG (SEQ ID NO:40; HCDR2), AYGNYWYIDR (SEQ ID NO:35; HCDR3), KSSQSVTNDVA (SEQ ID NO:36; LCDR1), YAYHRFT (SEQ ID NO:37; LCDR2) and HQAYSSPYT (SEQ ID NO:38; LCDR3) [Clone MH4];

(l) the amino acid sequences
GFTFSSYGMS (SEQ ID NO:33; HCDR1), VANIWQDGSTKYVDSVKG (SEQ ID NO:34; HCDR2), AYGNYWYIDR (SEQ ID NO:35; HCDR3), KSSQSVGNDVA (SEQ ID NO:74; LCDR1), YASHRFT (SEQ ID NO:45; LCDR2) and QQAYSSPYT (SEQ ID NO:75; LCDR3) [Clone MH5];

(m) the amino acid sequences
GFTFSSYGMS (SEQ ID NO:33; HCDR1), VANIWQDGSTKYVDSVKG (SEQ ID NO:34; HCDR2), AYGNYWYIDR (SEQ ID NO:35; HCDR3), KSSQSVTNDLA (SEQ ID NO:76; LCDR1), YASHRFT (SEQ ID NO:45; LCDR2) and QQAYSSPYT (SEQ ID NO:75; LCDR3) [Clone MH6];

(n) the amino acid sequences
GFTFSSYGMS (SEQ ID NO:33; HCDR1), VANIWQDGSTKYVDSVKG (SEQ ID NO:34; HCDR2), AYGNYWYIDR (SEQ ID NO:35; HCDR3), KSSQSVGNDLA (SEQ ID NO:77; LCDR1), YAYHRFS (SEQ ID NO:78; LCDR2) and QQAYSSPYT (SEQ ID NO:75; LCDR3) [Clone MH7];

(o) the amino acid sequences
GFTFSSYGMS (SEQ ID NO:33; HCDR1), VANIWQDGSTKYVDSVKG (SEQ ID NO:34; HCDR2), AYGNYWYIDR (SEQ ID NO:35; HCDR3), KSSQSVTNDVA (SEQ ID NO:36; LCDR1), YAYHRFT (SEQ ID NO:37; LCDR2) and HQAYSSPYT (SEQ ID NO:38; LCDR3) [Clone MH8];

(p) the amino acid sequences
GFTFSSYGMS (SEQ ID NO:33; HCDR1), VANIWQDGSEKYVDSVKG (SEQ ID NO:41; HCDR2), AYGNYWYIDR (SEQ ID NO:35; HCDR3), KSSQSVGNDVA (SEQ ID NO:74; LCDR1), YASHRFT (SEQ ID NO:45; LCDR2) and QQAYSSPYT (SEQ ID NO:75; LCDR3) [Clone MH9];

(q) the amino acid sequences
GFTFSSYGMS (SEQ ID NO:33; HCDR1), VANIWQDGSEKYVDSVKG (SEQ ID NO:41; HCDR2), AYGNYWYIDR (SEQ ID NO:35; HCDR3), KSSQSVTNDLA (SEQ ID NO:76; LCDR1), YASHRFT (SEQ ID NO:45; LCDR2) and QQAYSSPYT (SEQ ID NO:75; LCDR3) [Clone MH10];

(r) the amino acid sequences
GFTFSSYGMS (SEQ ID NO:33; HCDR1), VANIWQDGSEKYVDSVKG (SEQ ID NO:41; HCDR2), AYGNYWYIDR (SEQ ID NO:35; HCDR3), KSSQSVGNDLA (SEQ ID NO:77; LCDR1), YAYHRFS (SEQ ID NO:78; LCDR2) and QQAYSSPYT (SEQ ID NO:75; LCDR3) [Clone MH11];

(s) the amino acid sequences
GFTFSSYGMS (SEQ ID NO:33; HCDR1), VANIWQDGSEKYVDSVKG (SEQ ID NO:41; HCDR2), AYGNYWYIDR (SEQ ID NO:35; HCDR3), KSSQSVTNDVA (SEQ ID NO:36; LCDR1), YAYHRFT (SEQ ID NO:37; LCDR2) and HQAYSSPYT (SEQ ID NO:38; LCDR3) [Clone MH12];

(t) the amino acid sequences
GFTFSSYGMS (SEQ ID NO:33; HCDR1), VANIWQDGSTKYVDSVKG (SEQ ID NO:34; HCDR2), AYGNYWYIDR (SEQ ID NO:35; HCDR3), KSSQSVTNDLA (SEQ ID NO:76; LCDR1), YAYHRFT (SEQ ID NO:37; LCDR2) and HQAYSSPYT (SEQ ID NO:38; LCDR3) [Clone MH13];

(u) the amino acid sequences
GFTFSSYGMS (SEQ ID NO:33; HCDR1), VANIWQDGSTKYVDSVKG (SEQ ID NO:34; HCDR2), AYGNYWYIDR (SEQ ID NO:35; HCDR3), KSSQSVTNDLA (SEQ ID NO:76; LCDR1), YAYHRFS (SEQ ID NO:78; LCDR2) and HQAYSSPYT (SEQ ID NO:38; LCDR3) [Clone MH14];

(v) the amino acid sequences
GFTFSSYGMS (SEQ ID NO:33; HCDR1), VANIWQDGSTKYVDSVKG (SEQ ID NO:34; HCDR2), AYGNYWYIDR (SEQ ID NO:35; HCDR3), KSSQSVTNDLA (SEQ ID NO:76; LCDR1), YASHRFS (SEQ ID NO:79; LCDR2) and HQAYSSPYT (SEQ ID NO:38; LCDR3) [Clone MH15];

(w) the amino acid sequences
GFTFSSYGMS (SEQ ID NO:33; HCDR1), VANIWQDGSEKYVDSVKG (SEQ ID NO:41; HCDR2), AYGNYWYIDR (SEQ ID NO:35; HCDR3), KSSQSVTNDLA (SEQ ID NO:76; LCDR1), YAYHRFT (SEQ ID NO:37; LCDR2) and HQAYSSPYT (SEQ ID NO:38; LCDR3) [Clone MH16];

(x) the amino acid sequences
GFTFSSYGMS (SEQ ID NO:33; HCDR1), VANIWQDGSEKYVDSVKG (SEQ ID NO:41; HCDR2), AYGNYWYIDR (SEQ ID NO:35; HCDR3), KSSQSVTNDLA (SEQ ID NO:76; LCDR1), YAYHRFS (SEQ ID NO:78; LCDR2) and HQAYSSPYT (SEQ ID NO:38; LCDR3) [Clone MH17];

(y) the amino acid sequences
GFTFSSYGMS (SEQ ID NO:33; HCDR1), VANIWQDGSEKYVDSVKG (SEQ ID NO:41; HCDR2), AYGNYWYIDR (SEQ ID NO:35; HCDR3), KSSQSVTNDLA (SEQ ID NO:76; LCDR1), YASHRFS (SEQ ID NO:79; LCDR2) and HQAYSSPYT (SEQ ID NO:38; LCDR3) [Clone MH18];

In some aspects, the invention provides an anti-PD1 antibody or an antigen-binding portion thereof, wherein the antibody comprises a heavy chain variable (VH) region and a light chain variable (VL) region, wherein (a) the VH region amino acid sequence comprises HCDR1 of GFTFSSYGMS (SEQ ID NO:33), HCDR2 of VANIWQDGSTKYVDSVKG (SEQ ID NO:34), and HCDR3 of AYGNYWYIDR (SEQ ID NO:35); and the VL region amino acid sequence comprises LCDR1 of KSSQSVTNDVA (SEQ ID NO:36), LCDR2 of YAYHRFT (SEQ ID NO:37), and LCDR3 of HQAYSSPYT (SEQ ID NO:38);

(b) the VH region amino acid sequence comprises HCDR1 of GFSLSSYGMS (SEQ ID NO:39), HCDR2 of VAVIWQDGSTNYVDSVKG (SEQ ID NO:40), and HCDR3 of AYGNYWYIDR (SEQ ID NO:35); and the VL region amino acid sequence comprises LCDR1 of KSSQSVTNDVA (SEQ ID NO:36), LCDR2 of YAYHRFT (SEQ ID NO:37), and LCDR3 of HQAYSSPYT (SEQ ID NO:38);

(c) the VH region amino acid sequence comprises HCDR1 of GFTFSSYGMS (SEQ ID NO:33), HCDR2 of VANIWQDGSEKYVDSVKG (SEQ ID NO:41), and HCDR3 of AYGNYWYIDR (SEQ ID NO:35); and the VL region amino acid sequence comprises LCDR1 of KSSQSVTNDVA (SEQ ID NO:36), LCDR2 of YAYHRFT (SEQ ID NO:37), and LCDR3 of HQAYSSPYT (SEQ ID NO:38);

(d) the VH region amino acid sequence comprises HCDR1 of GFSFSSYGMH (SEQ ID NO:42), HCDR2 of VANIWQDGSTNYVDSVKG (SEQ ID NO:43), and HCDR3 of AYGNYWYIDR (SEQ ID NO:35); and the VL region amino acid sequence comprises LCDR1 of KSSQSVSNDVA (SEQ ID NO:44), LCDR2 of YASHRFT (SEQ ID NO:45), and LCDR3 of HQAYSTPYT (SEQ ID NO:46);

(e) the VH region amino acid sequence comprises HCDR1 of GFSFTSYGMS (SEQ ID NO:47), HCDR2 of LANIWQDGSTNYVDSVKG (SEQ ID NO:48), and HCDR3 of AYGNYWYIDR (SEQ ID NO:35); and the VL region amino acid sequence comprises LCDR1 of KSSQSVSNDVA (SEQ ID NO:44), LCDR2 of YASHRFT (SEQ ID NO:45), and LCDR3 of HQAYSTPYT (SEQ ID NO:46);

(f) the VH region amino acid sequence comprises HCDR1 of GFTFSSYGVH (SEQ ID NO:49), HCDR2 of VGVIWQDGSENYVDSVKG (SEQ ID NO:50), and HCDR3 of AYGNYWYIDR (SEQ ID NO:35); and the VL region amino acid sequence comprises LCDR1 of KSSQSVSNDLA (SEQ ID NO:51), LCDR2 of YASHRFT (SEQ ID NO:45), and LCDR3 of QQAYSTPYT (SEQ ID NO:52);

(g) the VH region amino acid sequence comprises HCDR1 of GFSFSSYGMH (SEQ ID NO:42), HCDR2 of VANIWQDGSTNYVDSVKG (SEQ ID NO:43), and HCDR3 of AYGNYWYIDR (SEQ ID NO:35); and the VL region amino acid sequence comprises LCDR1 of KSSQSVSNDVA (SEQ ID NO:44), LCDR2 of YASHRFT (SEQ ID NO:45), and LCDR3 of HQAYSTPYT (SEQ ID NO:46);

(h) the VH region amino acid sequence comprises HCDR1 of GFSFSSYGMH (SEQ ID NO:42), HCDR2 of LANIWQDGSENYVDSVKG (SEQ ID NO:53), and HCDR3 of AYGNYWYIDR (SEQ ID NO:35); and the VL region amino acid sequence comprises LCDR1 of KSSQS-VSNDVA (SEQ ID NO:44), LCDR2 of YASHRFT (SEQ ID NO:45), and LCDR3 of QQAYSTPYT (SEQ ID NO:52);

(i) the VH region amino acid sequence comprises HCDR1 of GFTLSSYGMH (SEQ ID NO:54), HCDR2 of LAVIWADGSTNYVDSVKG (SEQ ID NO:55), and HCDR3 of AYGNYMYIDV (SEQ ID NO:56); and the VL region amino acid sequence comprises LCDR1 of KSSQS-VSNDVA (SEQ ID NO:44), LCDR2 of YASHRFT (SEQ ID NO:45), and LCDR3 of HQAYSTPYT (SEQ ID NO:46);

(j) the VH region amino acid sequence comprises HCDR1 of GFTFSSYGMH (SEQ ID NO:57), HCDR2 of VGVIKQDGSENYVDSVKG (SEQ ID NO:58), and HCDR3 of AYGNYWYIDR (SEQ ID NO:35); and the VL region amino acid sequence comprises LCDR1 of KSSQS-VSNDVA (SEQ ID NO:44), LCDR2 of YASHRFT (SEQ ID NO:45), and LCDR3 of HQAYSTPYT (SEQ ID NO:46); or (k) the VH region amino acid sequence comprises HCDR1 of GFSFTSYGMH (SEQ ID NO:59), HCDR2 of VGVIWQDGSTNYVDSVKG (SEQ ID NO:60), and HCDR3 of GYGNYWYIDV (SEQ ID NO:61); and the VL region amino acid sequence comprises LCDR1 of KSSQS-VSNDLA (SEQ ID NO:51), LCDR2 of YASHRFT (SEQ ID NO:45), and LCDR3 of QQAYSTPYT (SEQ ID NO:52).

In some aspects, disclosed herein is anti-PD1 antibody or an antigen-binding portion thereof, wherein the antibody comprises a heavy chain variable (VH) region and a light chain variable (VL) region, wherein the VH region comprises any one of the VH region amino acid sequences in Table 9 and the VL region comprises any one of the VL region amino acid sequences in Table 9.

In some aspects, the invention provides an anti-PD1 antibody or an antigen-binding portion thereof, wherein the antibody comprises a heavy chain variable (VH) region and a light chain variable (VL) region, wherein (a) the VH region amino acid sequence comprises SEQ ID NO:1 and the VL region amino acid sequence comprises SEQ ID NO:2;

(b) the VH region amino acid sequence comprises SEQ ID NO:3 and the VL region amino acid sequence comprises SEQ ID NO:4;

(c) the VH region amino acid sequence comprises SEQ ID NO:5 and the VL region amino acid sequence comprises SEQ ID NO:6; or (d) the VH region amino acid sequence comprises SEQ ID NO:7 and the VL region amino acid sequence comprises SEQ ID NO:8.

In some aspects, disclosed herein is an anti-PD1 antibody or an antigen-binding portion thereof, wherein the antibody comprises a heavy chain variable (VH) region and a light chain variable (VL) region, wherein (a) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:1 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:2;

(b) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:3 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:4;

(c) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:5 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:6; or (d) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:7 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:8. In some aspects, the CDR amino acid sequences of an anti-PD1 antibody are 100% identical to the CDR amino acid sequences in the recited sequences while the FR amino acid sequences are less than 100% identical to the FR amino acid sequences in the recited sequences.

In some aspects, the antibody or antigen-binding portion as defined herein may be isolated.

The antibody molecule or antigen-binding portion as defined herein may cross-compete for binding to PD1 with an antibody or antigen-binding portion thereof comprising the sets of CDRs disclosed herein. In some embodiments, the invention provides an anti-PD1 antibody or an antigen-binding portion thereof, wherein the antibody or antigen-binding portion cross-competes for binding to PD1 with the antibody or antigen-binding portion comprising the sets of CDRs disclosed herein; and (a) comprises fully germline human framework amino acid sequences; and/or (b) binds specifically to human PD1 and cynomolgus PD1; and/or (c) does not comprise an oxidation site in the LCDR2; and/or (d) comprises a human germline peptide sequence with high MHC class II binding affinity (e.g., VKGRFTISR (SEQ ID NO:81)) in the HCDR2/framework 3 region of the VH domain; and/or (e) does not comprise a human T cell epitope sequence in the HCDR1/framework 2 region of the VH domain; and/or (f) does not comprise a human T cell epitope sequence in the HCDR3/framework 4 region of the VH domain; and/or (g) exhibits reduced charge species heterogeneity compared to antibody Hu317, when in IgG1 effector null antibody format. In some embodiments, a KD value of an antibody or antigen-binding portion may be determined by Biacore analysis. In some embodiments, an EC50 value of an antibody or antigen-binding portion may be determined by flow cytometric staining of PD-1 expressing cells (e.g., CHO cells).

The terms "cross-compete", "cross-competition", "cross-block", "cross-blocked" and "cross-blocking" are used interchangeably herein to mean the ability of an antibody or portion thereof to interfere with the binding directly or indirectly through allosteric modulation of the anti-PD1 antibodies of the invention to the target PD1 (e.g., human PD1). The extent to which an antibody or portion thereof is able to interfere with the binding of another to the target, and therefore whether it can be said to cross-block or cross-compete according to the invention, can be determined using competition binding assays. One example of a binding competition assay is Homogeneous Time Resolved Fluorescence (HTRF). One particularly suitable quantitative cross-competition assay uses a FACS- or an AlphaScreen-based approach to measure competition between the labelled (e.g. His tagged, biotinylated or radioactive labelled) antibody or portion thereof and the other antibody or portion thereof in terms of their binding to the target. In general, a cross-competing antibody or portion thereof is, for example, one which will bind to the target in the cross-competition assay such that, during the assay and in the presence of a second antibody or portion thereof, the recorded displacement of the immunoglobulin single variable domain or polypeptide according to the invention is up to 100% (e.g. in a FACS based competition assay) of the maximum theoretical displacement (e.g. displacement by cold (e.g. unlabeled) antibody or fragment thereof that needs to be cross-blocked) by the potentially cross-blocking antibody or fragment thereof that is present in a given amount. Preferably, cross-competing antibodies or portions thereof have a recorded displacement that is between 10% and 100%, or between 50% and 100%.

The antibody molecule or antigen-binding portion as defined herein may comprise one or more substitutions, deletions and/or insertions which remove a post-translational modification (PTM) site, for example a glycosylation site (N-linked or O-linked), a deamination site, a phosphorylation site or an isomerisation/fragmentation site.

More than 350 types of PTM are known. Key forms of PTM include phosphorylation, glycosylation (N- and O-linked), sumoylation, palmitoylation, acetylation, sulfation, myristoylation, prenylation and methylation (of K and R residues). Statistical methods to identify putative amino acid sites responsible for specific PTMs are well known in the art (see Zhou et al., 2016, Nature Protocols 1: 1318-1321). Removal of such a site for example by substitution, deletion and/or insertion and then optionally testing (experimentally and/or theoretically) for (a) binding activity and/or (b) loss of the PTM is contemplated.

For example, the Mu317 murine LCDR2 (as defined herein, i.e. the amino acid sequence YAFHRFT (SEQ ID NO:31)) has been identified to have a putative oxidation site at residue 3 (F). Removal of this site at equivalent positions in an LCDR2 of the invention, for example by conservative or non-conservative substitution (such as to S or Y), is envisaged (as for example in clones 09C06 and other clones in Tables 3 and 4).

The antibody molecule or antigen-binding portion thereof may be human, humanized or chimeric.

The antibody molecule or antigen-binding portion thereof may comprise one or more human variable domain framework scaffolds into which the CDRs have been inserted. For example, the VH region, the VL region, or both the VH and the VL region may comprise one or more human framework region amino acid sequences.

The antibody molecule or antigen-binding portion thereof may comprise an IGHV3-7 human germline scaffold into which the corresponding HCDR sequences have been inserted. The antibody molecule or antigen-binding portion thereof may comprise a VH region that comprises an IGHV3-7 human germline scaffold amino acid sequence into which a set of corresponding HCDR1, HCDR2 and HCDR3 amino acid sequences have been inserted.

The antibody molecule or antigen-binding portion thereof may comprise an IGKV4-1 human germline scaffold into which the corresponding LCDR sequences have been inserted. The antibody molecule or antigen-binding portion thereof may comprise a VL region that comprises an IGKV4-1 human germline scaffold amino acid sequence into which a set of corresponding LCDR1, LCDR2 and LCDR3 amino acid sequences have been inserted.

The antibody molecule or antigen-binding portion thereof may comprise an IGHV3-7 human germline scaffold into which the corresponding HCDR sequences have been inserted and an IGKV4-1 human germline scaffold into which the corresponding LCDR sequences have been inserted. The antibody molecule or antigen-binding portion thereof may comprise a VH region that comprises an IGHV3-7 human germline scaffold amino acid sequence into which a set of corresponding HCDR1, HCDR2 and HCDR3 amino acid sequences have been inserted and a VL region that comprises an IGKV4-1 human germline scaffold amino acid sequence into which a set of corresponding LCDR1, LCDR2 and LCDR3 amino acid sequences have been inserted. The HCDR1, HCDR2, HCDR3, LCDR1, LCDR2 and LCDR3 amino acid sequences may be the HCDR1, HCDR2, HCDR3, LCDR1, LCDR2 and LCDR3 amino acid sequences of any one of the clones in Table 4 (with all six CDR sequences being from the same clone).

In some aspects, the antibody molecule or antigen-binding portion thereof may comprise an immunoglobulin constant region. In some embodiments, the immunoglobulin constant region is IgG1, IgG2, IgG3, IgG4, IgA1 or IgA2. In additional embodiments, the immunoglobulin constant region is IgG1, IgG2, IgG3, IgG4, IgA1 or IgA2. The antibody molecule or antigen-binding portion thereof may comprise an immunologically inert constant region. In some aspects, an anti-PD1 antibody or antigen-binding portion thereof may comprise an immunoglobulin constant region comprising a wild-type human IgG1 constant region, a human IgG1 constant region comprising the amino acid substitutions L234A, L235A and G237A or a human IgG1 constant region comprising the amino acid substitutions L234A, L235A, G237A and P331S. In some aspects, an anti-PD1 antibody or antigen-binding portion thereof may comprise an immunoglobulin constant region comprising a wild-type human IgG2 constant region or a wild-type human IgG4 constant region. In some aspects, an anti-PD1 antibody may comprise an immunoglobulin constant region comprising any one of the amino acid sequences in Table 10. The Fc region sequences in Table 10 begin at the CH1 domain. In some aspects, an anti-PD1 antibody may comprise an immunoglobulin constant region comprising an amino acid sequence of an Fc region of human IgG4, human IgG4 (S228P), human IgG2, human IgG1, human IgG1-3M or human IgG1-4M. For example, the human IgG4(S228P) Fc region comprises the following substitution compared to the wild-type human IgG4 Fc region: S228P. For example, the human IgG1-3M Fc region comprises the following substitutions compared to the wild-type human IgG1 Fc region: L234A, L235A and G237A, while the human IgG1-4M Fc region comprises the following substitutions compared to the wild-type human IgG1 Fc region: L234A, L235A, G237A and P331S. In some aspects, a position of an amino acid residue in a constant region of an immunoglobulin molecule is numbered according to EU nomenclature (Ward et al., 1995 Therap. Immunol. 2:77-94). In some aspects, an immunoglobulin constant region may comprise an RDELT (SEQ ID NO:18) motif or an REEM (SEQ ID NO:19) motif (underlined in Table 18). The REEM (SEQ ID NO:19) allotype is found in a smaller human population than the RDELT (SEQ ID NO:18) allotype. In some aspects, an anti-PD1 antibody may comprise an immunoglobulin constant region comprising any one of SEQ ID NOS:9-15. In some aspects, an anti-PD1 antibody may comprise the six CDR amino acid sequences of any one of the clones in Table 4 and any one of the Fc region amino acid sequences in Table 10. In some aspects, an anti-PD1 antibody may comprise an immunoglobulin heavy chain constant region comprising any one of the Fc region amino acid sequences in Table 10 and an immunoglobulin light chain constant region that is a kappa light chain constant region or a lambda light chain constant region.

In some aspects, disclosed herein is an anti-PD1 antibody or an antigen-binding portion thereof, wherein the antibody comprises a heavy chain variable (VH) region, a light chain variable (VL) region and a heavy chain constant region, wherein (a) the VH region amino acid sequence comprises HCDR1 of GFTFSSYGMS (SEQ ID NO:33), HCDR2 of VANIWQDGSTKYVDSVKG (SEQ ID NO:34), and HCDR3 of AYGNYWYIDR (SEQ ID NO:35); the VL region amino acid sequence comprises LCDR1 of KSSQS-VTNDVA (SEQ ID NO:36), LCDR2 of YAYHRFT (SEQ ID NO:37), and LCDR3 of HQAYSSPYT (SEQ ID NO:38); and the heavy chain constant region comprises any one of SEQ ID NOS: 9-15;

(b) the VH region amino acid sequence comprises HCDR1 of GFSLSSYGMS (SEQ ID NO:39), HCDR2 of VAVIWQDGSTNYVDSVKG (SEQ ID NO:40), and HCDR3 of AYGNYWYIDR (SEQ ID NO:35); the VL region amino acid sequence comprises LCDR1 of KSSQS-VTNDVA (SEQ ID NO:36), LCDR2 of YAYHRFT (SEQ ID NO:37), and LCDR3 of HQAYSSPYT (SEQ ID NO:38); and the heavy chain constant region comprises any one of SEQ ID NOS: 9-15;

(c) the VH region amino acid sequence comprises HCDR1 of GFTFSSYGMS (SEQ ID NO:33), HCDR2 of VANIWQDGSEKYVDSVKG (SEQ ID NO:41), and HCDR3 of AYGNYWYIDR (SEQ ID NO:35); the VL region amino acid sequence comprises LCDR1 of KSSQS-VTNDVA (SEQ ID NO:36), LCDR2 of YAYHRFT (SEQ ID NO:37), and LCDR3 of HQAYSSPYT (SEQ ID NO:38); and the heavy chain constant region comprises any one of SEQ ID NOS: 9-15;

(d) the VH region amino acid sequence comprises HCDR1 of GFSFSSYGMH (SEQ ID NO:42), HCDR2 of VANIWQDGSTNYVDSVKG (SEQ ID NO:43), and HCDR3 of AYGNYWYIDR (SEQ ID NO:35); the VL region amino acid sequence comprises LCDR1 of KSSQS-VSNDVA (SEQ ID NO:44), LCDR2 of YASHRFT (SEQ ID NO:45), and LCDR3 of HQAYSTPYT (SEQ ID NO:46); and the heavy chain constant region comprises any one of SEQ ID NOS: 9-15;

(e) the VH region amino acid sequence comprises HCDR1 of GFSFTSYGMS (SEQ ID NO:47), HCDR2 of LANIWQDGSTNYVDSVKG (SEQ ID NO:48), and HCDR3 of AYGNYWYIDR (SEQ ID NO:35); the VL region amino acid sequence comprises LCDR1 of KSSQS-VSNDVA (SEQ ID NO:44), LCDR2 of YASHRFT (SEQ ID NO:45), and LCDR3 of HQAYSTPYT (SEQ ID NO:46); and the heavy chain constant region comprises any one of SEQ ID NOS: 9-15;

(f) the VH region amino acid sequence comprises HCDR1 of GFTFSSYGVH (SEQ ID NO:49), HCDR2 of VGVIWQDGSENYVDSVKG (SEQ ID NO:50), and HCDR3 of AYGNYWYIDR (SEQ ID NO:35); the VL region amino acid sequence comprises LCDR1 of KSSQSVSNDLA (SEQ ID NO:51), LCDR2 of YASHRFT (SEQ ID NO:45), and LCDR3 of QQAYSTPYT (SEQ ID NO:52); and the heavy chain constant region comprises any one of SEQ ID NOS: 9-15;

(g) the VH region amino acid sequence comprises HCDR1 of GFSFSSYGMH (SEQ ID NO:42), HCDR2 of VANIWQDGSTNYVDSVKG (SEQ ID NO:43), and HCDR3 of AYGNYWYIDR (SEQ ID NO:35); the VL region amino acid sequence comprises LCDR1 of KSSQS-VSNDVA (SEQ ID NO:44), LCDR2 of YASHRFT (SEQ ID NO:45), and LCDR3 of HQAYSTPYT (SEQ ID NO:46); and the heavy chain constant region comprises any one of SEQ ID NOS: 9-15;

(h) the VH region amino acid sequence comprises HCDR1 of GFSFSSYGMH (SEQ ID NO:42), HCDR2 of LANIWQDGSENYVDSVKG (SEQ ID NO:53), and HCDR3 of AYGNYWYIDR (SEQ ID NO:35); the VL region amino acid sequence comprises LCDR1 of KSSQS-VSNDVA (SEQ ID NO:44), LCDR2 of YASHRFT (SEQ ID NO:45), and LCDR3 of QQAYSTPYT (SEQ ID NO:52); and the heavy chain constant region comprises any one of SEQ ID NOS: 9-15;

(i) the VH region amino acid sequence comprises HCDR1 of GFTLSSYGMH (SEQ ID NO:54), HCDR2 of LAVIWADGSTNYVDSVKG (SEQ ID NO:55), and HCDR3 of AYGNYMYIDV (SEQ ID NO:56); the VL region amino acid sequence comprises LCDR1 of KSSQSVSNDVA (SEQ ID NO:44), LCDR2 of YASHRFT (SEQ ID NO:45), and LCDR3 of HQAYSTPYT (SEQ ID NO:46); and the heavy chain constant region comprises any one of SEQ ID NOS: 9-15;

(j) the VH region amino acid sequence comprises HCDR1 of GFTFSSYGMH (SEQ ID NO:57), HCDR2 of VGVIKQDGSENYVDSVKG (SEQ ID NO:58), and HCDR3 of AYGNYWYIDR (SEQ ID NO:35); the VL region amino acid sequence comprises LCDR1 of KSSQS-VSNDVA (SEQ ID NO:44), LCDR2 of YASHRFT (SEQ ID NO:45), and LCDR3 of HQAYSTPYT (SEQ ID NO:46); and the heavy chain constant region comprises any one of SEQ ID NOS: 9-15; or (k) the VH region amino acid sequence comprises HCDR1 of GFSFTSYGMH (SEQ ID NO:59), HCDR2 of VGVIWQDGSTNYVDSVKG (SEQ ID NO:60), and HCDR3 of GYGNYWYIDV (SEQ ID NO:61); the VL region amino acid sequence comprises LCDR1 of KSSQS-VSNDLA (SEQ ID NO:51), LCDR2 of YASHRFT (SEQ ID NO:45), and LCDR3 of QQAYSTPYT (SEQ ID NO:52); and the heavy chain constant region comprises any one of SEQ ID NOS: 9-15.

In some aspects, disclosed herein is an anti-PD1 antibody or an antigen-binding portion thereof, wherein the antibody comprises a heavy chain variable (VH) region, a light chain variable (VL) region and a heavy chain constant region, wherein (a) the VH region amino acid sequence comprises or consists of SEQ ID NO:1; the VL region amino acid sequence comprises or consists of SEQ ID NO:2; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;

(b) the VH region amino acid sequence comprises or consists of SEQ ID NO:3; the VL region amino acid sequence comprises or consists of SEQ ID NO:4; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;

(c) the VH region amino acid sequence comprises or consists of SEQ ID NO:5; the VL region amino acid sequence comprises or consists of SEQ ID NO:6; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A; or (d) the VH region amino acid sequence comprises or consists of SEQ ID NO:7; the VL region amino acid sequence comprises or consists of SEQ ID NO:8; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A.

In some aspects, disclosed herein is an anti-PD1 antibody or an antigen-binding portion thereof, wherein the antibody comprises a heavy chain variable (VH) region, a light chain variable (VL) region and a heavy chain constant region, wherein (a) the VH region amino acid sequence comprises or consists of SEQ ID NO:1; the VL region amino acid sequence comprises or consists of SEQ ID NO:2; and the heavy chain constant region comprises any one of SEQ ID NOS: 9-15;

(b) the VH region amino acid sequence comprises or consists of SEQ ID NO:3; the VL region amino acid sequence comprises or consists of SEQ ID NO:4; and the heavy chain constant region comprises any one of SEQ ID NOS: 9-15;

(c) the VH region amino acid sequence comprises or consists of SEQ ID NO:5; the VL region amino acid sequence comprises or consists of SEQ ID NO:6; and the heavy chain constant region comprises any one of SEQ ID NOS: 9-15; or (d) the VH region amino acid sequence comprises or consists of SEQ ID NO:7; the VL region amino acid sequence comprises or consists of SEQ ID NO:8; and the heavy chain constant region comprises any one of SEQ ID NOS: 9-15.

In some aspects, an anti-PD1 antibody may be immune effector null. In some aspects, an anti-PD1 antibody or an antigen-binding portion thereof does not induce immune effector function and, optionally, suppresses immune effector function. In some aspects, an anti-PD1 antibody may lack measurable binding to human FcγRI, FcγRIIa, FcγRIIIa and FcγRIIIb receptors but maintain binding to human FcγRIIb receptor and optionally maintain binding to human FcRn receptor. FcγRI, FcγRIIa, FcγRIIIa and FcγRIIIb are examples of activating receptors. FcγRIIb is an example of an inhibitory receptor. FcRn is an example of a recycling receptor. In some aspects, binding affinity of an anti-PD1 antibody or an antigen-binding portion thereof for human Fc receptors may be measured by BIACORE® analysis. In some aspects, Homogeneous Time Resolved Fluorescence (HTRF) can be used to study binding of an anti-PD1 antibody to human Fc receptors. In one example of HTRF, human IgG1 (wild type) is labelled, as is the full suite of Fc gamma receptors and then antibodies with engineered Fc fragments are used in titration competition. In some aspects, PD1-positive cells may be mixed with human white blood cells and anti-PD1 antibodies, and cell killing by CDC, ADCC and/or ADCP may be measured. In some aspects, an anti-PD1 antibody comprising an amino acid sequence of an Fc region of human IgG1-3M (see Table 10) is effector null. In some aspects, an anti-PD1 antibody comprising an amino acid sequence of an Fc region of human IgG1-3M (see Table 10) is not effector null.

The antibody molecule or antigen-binding portion thereof may be a Fab fragment, a F(ab)$_2$ fragment, an Fv fragment, a tetrameric antibody, a tetravalent antibody, a multispecific antibody (for example, a bivalent antibody), a domain-specific antibody, a single domain antibody, a monoclonal antibody or a fusion protein. In one embodiment, an antibody may be a bispecific antibody that binds specifically to a first antigen and a second antigen, wherein the first antigen is PD1 and the second antigen is not PD1. Antibody molecules and methods for their construction and use are described, in for example Holliger & Hudson (2005, Nature Biotechnol. 23(9): 1126-1136).

In another aspect of the invention, there is provided an immunoconjugate comprising the antibody molecule or antigen-binding portion thereof of the invention as defined herein linked a therapeutic agent.

Examples of suitable therapeutic agents include cytotoxins, radioisotopes, chemotherapeutic agents, immunomodulatory agents, anti-angiogenic agents, antiproliferative agents, pro-apoptotic agents, and cytostatic and cytolytic enzymes (for example RNAses). Further therapeutic agents include a therapeutic nucleic acid, such as a gene encoding an immunomodulatory agent, an anti-angiogenic agent, an anti-proliferative agent, or a pro-apoptotic agent. These drug descriptors are not mutually exclusive, and thus a therapeutic agent may be described using one or more of the above terms.

Examples of suitable therapeutic agents for use in immunoconjugates include the taxanes, maytansines, CC-1065 and the duocarmycins, the calicheamicins and other enediynes, and the auristatins. Other examples include the antifolates, vinca alkaloids, and the anthracyclines. Plant toxins, other bioactive proteins, enzymes (i.e., ADEPT), radioisotopes, photosensitizers may also be used in immunoconjugates. In addition, conjugates can be made using secondary carriers as the cytotoxic agent, such as liposomes or polymers, Suitable cytotoxins include an agent that inhibits or prevents the function of cells and/or results in destruction of cells. Representative cytotoxins include antibiotics, inhibitors of tubulin polymerization, alkylating agents that bind to and disrupt DNA, and agents that disrupt protein synthesis or the function of essential cellular proteins such as protein kinases, phosphatases, topoisomerases, enzymes, and cyclins.

Representative cytotoxins include, but are not limited to, doxorubicin, daunorubicin, idarubicin, aclarubicin, zorubicin, mitoxantrone, epirubicin, carubicin, nogalamycin, menogaril, pitarubicin, valrubicin, cytarabine, gemcitabine, trifluridine, ancitabine, enocitabine, azacitidine, doxifluhdine, pentostatin, broxuhdine, capecitabine, cladhbine, decitabine, floxuhdine, fludarabine, gougerotin, puromycin, tegafur, tiazofuhn, adhamycin, cisplatin, carboplatin, cyclophosphamide, dacarbazine, vinblastine, vincristine, mitoxantrone, bleomycin, mechlorethamine, prednisone, procarbazine, methotrexate, flurouracils, etoposide, taxol, taxol analogs, platins such as cis-platin and carbo-platin, mitomycin, thiotepa, taxanes, vincristine, daunorubicin, epirubicin, actinomycin, authramycin, azaserines, bleomycins, tamoxifen, idarubicin, dolastatins/auristatins, hemiasterlins, esperamicins and maytansinoids.

Suitable immunomodulatory agents include anti-hormones that block hormone action on tumors and immunosuppressive agents that suppress cytokine production, downregulate self-antigen expression, or mask MHC antigens.

Also provided is a nucleic acid molecule encoding the antibody molecule or antigen-binding portion thereof of the invention as defined herein. A nucleic acid molecule may encode (a) the VH region amino acid sequence; (b) the VL region amino acid sequence; or (c) both the VH and the VL region amino acid sequences of an anti-PD1 antibody or an antigen-binding portion thereof described herein. In some aspects, the nucleic acid molecule as defined herein may be isolated.

Further provided is a vector comprising the nucleic acid molecule of the invention as defined herein. The vector may be an expression vector.

Also provided is a host cell comprising the nucleic acid molecule or the vector of the invention as defined herein. The host cell may be a recombinant host cell.

In a further aspect there is provided a method of producing an anti-PD1 antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the nucleic acid molecule of the invention as defined herein, or the vector of the invention as defined herein.

Further provided is a method for enhancing an immune response in a subject, comprising administering to the subject an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

In a further aspect there is provided a method for treating or preventing cancer in a subject, comprising administering to the subject an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

For example, the cancer may be pancreatic cancer, melanoma, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, or cancer of hematological tissues.

The invention also provides an antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein, for use in the treatment of cancer.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination combined with a second therapeutic agent, for example an anti-cancer agent.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The invention also provides a method for treating or preventing an infectious or immune disease in a subject, comprising administering to the subject an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

In one embodiment, the invention provides an anti-PD1 antibody or an antigen-binding portion thereof comprising the amino acid sequences disclosed herein for use in therapy.

The pharmaceutical composition of the invention may comprise a pharmaceutically acceptable excipient, carrier, or diluent. A pharmaceutically acceptable excipient may be a compound or a combination of compounds entering into a pharmaceutical composition which does not provoke secondary reactions and which allows, for example, facilitation of the administration of the anti-PD1 antibody molecule, an increase in its lifespan and/or in its efficacy in the body or an increase in its solubility in solution. These pharmaceutically acceptable vehicles are well known and will be adapted by the person skilled in the art as a function of the mode of administration of the anti-PD1 antibody molecule.

In some embodiments, the anti-PD1 antibody molecule may be provided in a lyophilised form for reconstitution prior to administration. For example, lyophilised antibody molecules may be re-constituted in sterile water and mixed with saline prior to administration to an individual.

The anti-PD1 antibody molecules will usually be administered in the form of a pharmaceutical composition, which may comprise at least one component in addition to the antibody molecule. Thus pharmaceutical compositions may comprise, in addition to the anti-PD1 antibody molecule, a pharmaceutically acceptable excipient, carrier, buffer, stabilizer or other materials well known to those skilled in the art. Such materials should be non-toxic and should not interfere with the efficacy of the anti-PD1 antibody molecule. The precise nature of the carrier or other material will depend on the route of administration, which may be by bolus, infusion, injection or any other suitable route, as discussed below.

For parenteral, for example sub-cutaneous or intra-venous administration, e.g. by injection, the pharmaceutical composition comprising the anti-PD1 antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringe's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

A pharmaceutical composition comprising an anti-PD1 antibody molecule may be administered alone or in combination with other treatments, either simultaneously or sequentially dependent upon the condition to be treated.

An anti-PD1 antibody molecule as described herein may be used in a method of treatment of the human or animal body, including prophylactic or preventative treatment (e.g. treatment before the onset of a condition in an individual to reduce the risk of the condition occurring in the individual; delay its onset; or reduce its severity after onset). The method of treatment may comprise administering the anti-PD1 antibody molecule to an individual in need thereof.

Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the method of administration, the scheduling of administration and other factors known to medical practitioners. Prescription of treatment, e.g. decisions on dosage etc., is within the responsibility of general practitioners and other medical doctors and may depend on the severity of the symptoms and/or progression of a disease being treated. Appropriate doses of antibody molecules are well known in the art (Ledermann J. A. et al., 1991, Int. J. Cancer 47: 659-664; Bagshawe K. D. et al., 1991, Antibody, Immunoconjugates and Radiopharmaceuticals 4: 915-922). Specific dosages may be indicated herein or in the Physician's Desk Reference (2003) as appropriate for the type of medicament being administered may be used. A therapeutically effective amount or suitable dose of an antibody molecule may be determined by comparing its in vitro activity and in vivo activity in an animal model. Methods for extrapolation of effective dosages in mice and other test animals to humans are known. The precise dose will depend upon a number of factors, including whether the antibody is for prevention or for treatment, the size and location of the area to be treated, the precise nature of the antibody (e.g. whole antibody, fragment) and the nature of any detectable label or other molecule attached to the antibody.

A typical antibody dose will be in the range 100 µg to 1 g for systemic applications, and 1 µg to 1 mg for topical applications. An initial higher loading dose, followed by one or more lower doses, may be administered. Typically, the antibody will be a whole antibody, e.g. the IgG1 or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. The treatment schedule for an individual may be dependent on the pharmocokinetic and pharmacodynamic properties of the antibody composition, the route of administration and the nature of the condition being treated.

Treatment may be periodic, and the period between administrations may be about two weeks or more, e.g. about three weeks or more, about four weeks or more, about once a month or more, about five weeks or more, or about six weeks or more. For example, treatment may be every two to four weeks or every four to eight weeks. Treatment may be given before, and/or after surgery, and/or may be administered or applied directly at the anatomical site of surgical treatment or invasive procedure. Suitable formulations and routes of administration are described above.

In some embodiments, anti-PD1 antibody molecules as described herein may be administered as sub-cutaneous injections. Sub-cutaneous injections may be administered using an auto-injector, for example for long term prophylaxis/treatment.

In some embodiments, the therapeutic effect of the anti-PD1 antibody molecule may persist for several half-lives, depending on the dose. For example, the therapeutic effect of a single dose of the anti-PD1 antibody molecule may persist in an individual for 1 month or more, 2 months or more, 3 months or more, 4 months or more, 5 months or more, or 6 months or more.

The invention also provides a method of producing an antibody molecule which specifically binds to human PD1 and optionally also to cynomolgus monkey PD1, or an antigen-binding portion thereof, comprising the steps of:

(1) grafting anti-PD1 CDRs from a non-human source into a human v-domain framework to produce a humanized anti-PD1 antibody molecule or antigen-binding portion thereof;

(2) generating a library of clones of the humanized anti-PD1 antibody molecule or antigen-binding portion thereof comprising one or more mutations in the CDRs;

(3) screening the library for binding to human PD1 and optionally also to cynomolgus monkey PD1;

(4) selecting clones from the screening step (3) having binding specificity to human PD1 and optionally also to cynomolgus monkey PD1; and (5) producing an antibody molecule which specifically binds to human PD1 and optionally also to cynomolgus monkey PD1, or an antigen-binding portion thereof from clones selected from step (4).

The method may comprise a further step of producing additional clones based on the clones selected in step (4), for example based on further exploratory mutagenesis at specific positions in the CDRs of the clones selected in step (4), to enhance humanization and/or minimise human T cell epitope content and/or improve manufacturing properties in the antibody molecule or antigen-binding portion thereof produced in step (5).

Refinements applicable to the above method are as described in Example 1 below.

As used herein, the term "PD1" refers to Programmed Cell Death Protein 1 and variants thereof that retain at least part of the biological activity of PD1. As used herein, PD1 includes all species of native sequence PD1, including human, rat, mouse and chicken. The term "PD1" is used to include variants, isoforms and species homologs of human PD1. Antibodies of the invention may cross-react with PD1 from species other than human, in particular PD1 from cynomolgus monkey (*Macaca fascicularis*). Examples of human and cynomolgus PD1 amino acid sequences are provided in Table 11. In certain embodiments, the antibodies may be completely specific for human PD1 and may not exhibit non-human cross-reactivity.

As used herein, an "antagonist" as used in the context of the antibody of the invention or an "anti-PD1 antagonist antibody" (interchangeably termed "anti-PD1 antibody") refers to an antibody which is able to bind to PD1 and inhibit PD1 biological activity and/or downstream pathway(s) mediated by PD1 signalling. An anti-PD1 antagonist antibody encompasses antibodies that can block, antagonize, suppress or reduce (including significantly) PD1 biological activity, including downstream pathways mediated by PD1 signalling, such as receptor binding and/or elicitation of a cellular response to PD1. For the purposes of the present invention, it will be explicitly understood that the term "anti-PD1 antagonist antibody" encompass all the terms, titles, and functional states and characteristics whereby PD1 itself, and PD1 biological activity (including but not limited to its ability to suppress the activation of anti-tumour cell activity of T cells), or the consequences of the activity or biological activity, are substantially nullified, decreased, or neutralized in any meaningful degree.

PD1 "specifically binds" "specifically interacts", "preferentially binds", "binds" or "interacts" with PD1 if it binds with greater affinity, avidity, more readily and/or with greater duration than it binds to other receptors.

An "antibody molecule" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody molecule" encompasses not only intact polyclonal or monoclonal antibodies, but also any antigen binding fragment (for example, an "antigen-binding portion") or single chain thereof, fusion proteins comprising an antibody, and any other modified configuration of the immunoglobulin molecule that comprises an antigen recognition site including, for example without limitation, scFv, single domain antibodies (for example, shark and camelid antibodies), maxibodies, minibodies, intrabodies, diabodies, triabodies, tetrabodies, v-NAR and bis-scFv.

An "antibody molecule" encompasses an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), for example IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding portion" of an antibody molecule, as used herein, refers to one or more fragments of an intact antibody that retain the ability to specifically bind to PD1. Antigen binding functions of an antibody molecule can be performed by fragments of an intact antibody. Examples of binding fragments encompassed within the term "antigen binding portion" of an antibody molecule include Fab; Fab'; F(ab')2; an Fd fragment consisting of the VH and CH1 domains; an Fv fragment consisting of the VL and VH domains of a single arm of an antibody; a single domain antibody (dAb) fragment, and an isolated complementarity determining region (CDR).

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. The Fc region of an immunoglobulin generally comprises two constant domains, CH2 and CH3. As is known in the art, an Fc region can be present in dimer or monomeric form.

A "variable region" of an antibody refers to the variable region of the antibody light chain or the variable region of the antibody heavy chain, either alone or in combination. As known in the art, the variable regions of the heavy and light chain each consist of four framework regions (FRs) connected by three complementarity determining regions (CDRs) also known as hypervariable regions, contribute to the formation of the antigen binding site of antibodies. When choosing FR to flank CDRs, for example when humanizing or optimizing an antibody, FRs from antibodies which contain CDR sequences in the same canonical class are preferred.

The CDR definitions used in the present application combine the domains used in the many disparate, often conflicting schemes that have been created in the field, which are based on the combination of immunoglobulin repertoire analyses and structural analyses of antibodies in isolation and in their co-crystals with antigens (see review by Swindells et al., 2016, abYsis: Integrated Antibody Sequence and Structure-Management, Analysis, and Prediction. J Mol Biol. [PMID: 27561707; Epub 22 Aug. 2016]). The CDR definition used herein (a "Unified" definition) incorporates the lessons of all such prior insights and includes all appropriate loop positions required to sample the full residue landscape that potentially mediates target-binding complementarity.

Table 1 shows the amino acid sequences of the Mu317 murine anti-PD1 antibody CDRs as defined herein (a "Unified" scheme), in comparison to well-known alternative systems for defining the same CDRs.

As used herein the term "conservative substitution" refers to replacement of an amino acid with another amino acid which does not significantly deleteriously change the functional activity. A preferred example of a "conservative substitution" is the replacement of one amino acid with another amino acid which has a value ≥0 in the following BLOSUM 62 substitution matrix (see Henikoff & Henikoff, 1992, PNAS 89: 10915-10919):

|   | A  | R  | N  | D  | C  | Q  | E  | G  | H  | I  | L  | K  | M  | F  | P  | S  | T  | W  | Y  | V  |
|---|----|----|----|----|----|----|----|----|----|----|----|----|----|----|----|----|----|----|----|----|
| A | 4  | -1 | -2 | 0  | 0  | -1 | -1 | 0  | -2 | -1 | -1 | -1 | -1 | -2 | -1 | 1  | 0  | -3 | -2 | 0  |
| R | -1 | 5  | 0  | -2 | -3 | 1  | 0  | -2 | 0  | -3 | -2 | 2  | -1 | -3 | -2 | -1 | -1 | -3 | -2 | -3 |
| N | -2 | 0  | 6  | 1  | -3 | 0  | 0  | 0  | 1  | -3 | -3 | 0  | -2 | -3 | -2 | 1  | 0  | -4 | -2 | -3 |
| D | -2 | -2 | 1  | 6  | -3 | 0  | 2  | -1 | -1 | -3 | -4 | -1 | -3 | -3 | -1 | 0  | -1 | -4 | -3 | -3 |
| C | 0  | -3 | -3 | -3 | 9  | -3 | -4 | -3 | -3 | -1 | -1 | -3 | -1 | -2 | -3 | -1 | -1 | -2 | -2 | -1 |
| Q | -1 | 1  | 0  | 0  | -3 | 5  | 2  | -2 | 0  | -3 | -2 | 1  | 0  | -3 | -1 | 0  | -1 | -2 | -1 | -2 |
| E | -1 | 0  | 0  | 2  | -4 | 2  | 5  | -2 | 0  | -3 | -3 | 1  | -2 | -3 | -1 | 0  | -1 | -3 | -2 | -2 |
| G | 0  | -2 | 0  | -1 | -3 | -2 | -2 | 6  | -2 | -4 | -4 | -2 | -3 | -3 | -2 | 0  | -2 | -2 | -3 | -3 |
| H | -2 | 0  | 1  | -1 | -3 | 0  | 0  | -2 | 8  | -3 | -3 | -1 | -2 | -1 | -2 | -1 | -2 | -2 | 2  | -3 |
| I | -1 | -3 | -3 | -3 | -1 | -3 | -3 | -4 | -3 | 4  | 2  | -3 | 1  | 0  | -3 | -2 | -1 | -3 | -1 | 3  |
| L | -1 | -2 | -3 | -4 | -1 | -2 | -3 | -4 | -3 | 2  | 4  | -2 | 2  | 0  | -3 | -2 | -1 | -2 | -1 | 1  |
| K | -1 | 2  | 0  | -1 | -3 | 1  | 1  | -2 | -1 | -3 | -2 | 5  | -1 | -3 | -1 | 0  | -1 | -3 | -2 | -2 |
| M | -1 | -1 | -2 | -3 | -1 | 0  | -2 | -3 | -2 | 1  | 2  | -1 | 5  | 0  | -2 | -1 | -1 | -1 | -1 | 1  |
| F | -2 | -3 | -3 | -3 | -2 | -3 | -3 | -3 | -1 | 0  | 0  | -3 | 0  | 6  | -4 | -2 | -2 | 1  | 3  | -1 |
| P | -1 | -2 | -2 | -1 | -3 | -1 | -1 | -2 | -2 | -3 | -3 | -1 | -2 | -4 | 7  | -1 | -1 | -4 | -3 | -2 |
| S | 1  | -1 | 1  | 0  | -1 | 0  | 0  | 0  | -1 | -2 | -2 | 0  | -1 | -2 | -1 | 4  | 1  | -3 | -2 | -2 |
| T | 0  | -1 | 0  | -1 | -1 | -1 | -1 | -2 | -2 | -1 | -1 | -1 | -1 | -2 | -1 | 1  | 5  | -2 | -2 | 0  |
| W | -3 | -3 | -4 | -4 | -2 | -2 | -3 | -2 | -2 | -3 | -2 | -3 | -1 | 1  | -4 | -3 | -2 | 11 | 2  | -3 |
| Y | -2 | -2 | -2 | -3 | -2 | -1 | -2 | -3 | 2  | -1 | -1 | -2 | -1 | 3  | -3 | -2 | -2 | 2  | 7  | -1 |
| V | 0  | -3 | -3 | -3 | -1 | -2 | -2 | -3 | -3 | 3  | 1  | -2 | 1  | -1 | -2 | -2 | 0  | -3 | -1 | 4. |

The term "monoclonal antibody" (Mab) refers to an antibody, or antigen-binding portion thereof, that is derived from a single copy or clone, including for example any eukaryotic, prokaryotic, or phage clone, and not the method by which it is produced. Preferably, a monoclonal antibody of the invention exists in a homogeneous or substantially homogeneous population.

A "humanized" antibody molecule refers to a form of non-human (for example, murine) antibody molecules, or antigen-binding portion thereof, that are chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. Humanized antibodies may be human immunoglobulins (recipient antibody) in which residues from a CDR of the recipient are replaced by residues from a CDR of a non-human species (donor antibody) such as mouse, rat, or rabbit having the desired specificity, affinity, and capacity.

"Human antibody or fully human antibody" refers to an antibody molecule, or antigen-binding portion thereof, derived from transgenic mice carrying human antibody genes or from human cells.

The term "chimeric antibody" is intended to refer to an antibody molecule, or antigen-binding portion thereof, in which the variable region sequences are derived from one species and the constant region sequences are derived from another species, such as an antibody molecule in which the variable region sequences are derived from a mouse antibody and the constant region sequences are derived from a human antibody.

"Antibody-drug conjugate" and "immunoconjugate" refer to an antibody molecule, or antigen-binding portion thereof, including antibody derivatives that binds to PD1 and is conjugated to cytotoxic, cytostatic and/or therapeutic agents.

Antibody molecules of the invention, or antigen-binding portion thereof, can be produced using techniques well known in the art, for example recombinant technologies, phage display technologies, synthetic technologies or combinations of such technologies or other technologies readily known in the art.

The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The term "epitope" refers to that portion of a molecule capable of being recognized by and bound by an antibody molecule, or antigen-binding portion thereof, at one or more of the antibody molecule's antigen-binding regions. Epitopes can consist of defined regions of primary secondary or tertiary protein structure and includes combinations of secondary structural units or structural domains of the target recognised by the antigen binding regions of the antibody, or antigen-binding portion thereof. Epitopes can likewise consist of a defined chemically active surface grouping of molecules such as amino acids or sugar side chains and have specific three-dimensional structural characteristics as well as specific charge characteristics. The term "antigenic epitope" as used herein, is defined as a portion of a polypeptide to which an antibody molecule can specifically bind as determined by any method well known in the art, for example, by conventional immunoassays, antibody competitive binding assays or by x-ray crystallography or related structural determination methods (for example NMR).

The term "binding affinity" or "KD" refers to the dissociation rate of a particular antigen-antibody interaction. The KD is the ratio of the rate of dissociation, also called the "off-rate ($k_{off}$)", to the association rate, or "on-rate ($k_{on}$)". Thus, $K_D$ equals $k_{off}/k_{on}$ and is expressed as a molar concentration (M). It follows that the smaller the $K_D$, the stronger the affinity of binding. Therefore, a $K_D$ of 1 μM indicates weak binding affinity compared to a $K_D$ of 1 nM. KD values for antibodies can be determined using methods well established in the art. One method for determining the KD of an antibody is by using surface plasmon resonance (SPR), typically using a biosensor system such as a Biacore® system.

The term "potency" is a measurement of biological activity and may be designated as $IC_{50}$, or effective concentration of an antibody or antibody drug conjugate to the antigen PD1 to inhibit 50% of activity measured in a PD1 activity assay as described herein.

The phrase "effective amount" or "therapeutically effective amount" as used herein refers to an amount necessary (at dosages and for periods of time and for the means of administration) to achieve the desired therapeutic result. An effective amount is at least the minimal amount, but less than a toxic amount, of an active agent which is necessary to impart therapeutic benefit to a subject.

The term "inhibit" or "neutralize" as used herein with respect to bioactivity of an antibody molecule of the invention means the ability of the antibody to substantially antagonize, prohibit, prevent, restrain, slow, disrupt, eliminate, stop, reduce or reverse for example progression or severity of that which is being inhibited including, but not limited to, a biological activity or binding interaction of the antibody molecule to PD1.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as defined above. The term "treating" also includes adjuvant and neoadjuvant treatment of a subject. For the avoidance of doubt, reference herein to "treatment" includes reference to curative, palliative and prophylactic treatment. For the avoidance of doubt, references herein to "treatment" also include references to curative, palliative and prophylactic treatment.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

The practice of the present invention will employ, unless otherwise indicated, conventional techniques of molecular biology (including recombinant techniques), microbiology, cell biology, biochemistry and immunology, which are within the skill of the art.

Particular non-limiting embodiments of the present invention will now be described with reference to accompanying drawings.

Example 1. Generation of Optimized Anti-PD1 Therapeutic Antibodies

Introduction

In this example, we successfully generate a panel of agonistic, optimized anti-PD1 antibodies. These anti-PD1 antibodies are well expressed, biophysically stable, highly soluble and of maximized identity to preferred human germlines.

Materials and Methods

PD1 Library Generation and Selection

The PD1 Fab library was assembled by mass oligo synthesis and PCR. The amplified Fab repertoire was then cloned via restriction-ligation into a phagemid vector, transformed into *E. coli* TG-1 cells, and the phage repertoire rescued essentially as previously described in detail (Finlay et al., 2011, Methods Mol Biol 681: 383-401).

Phage selections were performed by coating streptavidin magnetic microbeads with biotinylated PD1 target protein (either human or cyno), washing the beads thrice with PBS and resuspending in PBS pH7.4 plus 5% skim milk protein. These beads were coated at 100 nM target protein in round 1 of selection, followed by reduced antigen concentrations in three successive rounds. In each round, phage were eluted using trypsin before re-infection into TG1 cells.

Periplasmic Extracts Production (Small-Scale)

Production of soluble Fabs in individual *E. coli* clones was performed. *E. coli* TG1 cells in logarhythmic growth phase were induced with isopropyl 1-thio-β-D-galactopyranoside. Periplasmic extracts containing soluble Fab were generated by a freeze/thaw cycle: BacteriaL cell pellets were frozen at −20° C. for overnight and then thawed at room temperature and resuspended in PBS pH 7.4. The supernatants containing the soluble Fab were collected after shaking at room temperature and centrifugation.

IgG Expression and Purification

Mammalian codon-optimized synthetic genes encoding the heavy and light chain variable domains of the lead panel anti-PD1 antibodies plus the Mu317 and hu317 were cloned into mammalian expression vectors comprising effector function null human IgG1 ('IgG1null'; human IgG1 containing L234A, L235A, G237A mutations in the lower hinge that abrogate normal immunoglobulin FcγR interactions) and human Cκ domains, respectively. Co-transfection of heavy and light chain containing vector in mammalian expression system was performed, followed by protein A-based purification of the IgG, quantification and QC on denaturing and non-denaturing SDS-PAGE.

Direct Binding ELISA for Fab and IgG

Binding and cross-reactivity of the lead panel to the recombinant proteins was initially assessed by binding ELISA. The human PD1 human Fc tagged recombinant protein and the cynomolgus monkey PD1 human Fc tagged recombinant protein were coated to the surface of Max-iSorp™ flat-bottom 96 well plate at 1 µg/ml. The Fab samples were applied at 1:5 dilution in 1% Skimmed Milk/1×PBS; 1 h at RT; 100 µl/well. IgGs were titrated in two fold serial dilutions starting from 500 nM to 0.98 nM and allowed to bind to the coated antigens. The Fabs were detected using mouse anti-c-myc antibody followed by donkey anti-mouse IgG conjugated to horseradish peroxidase. The IgGs were detected using the mouse anti-human IgG conjugated to horseradish peroxidase. Binding signals were visualized with 3,3',5,5'-Tetramethylbenzidine Substrate Solution (TMB) and the absorbance measured at 450 nm.

Alphascreen Epitope Competition Assay for IgG1 Null Antibodies

The AlphaScreen assay (Perkin Elmer) was performed in a 25 µl final volume in 384-well white microtiter plates (Greiner). The reaction buffer contained 1×PBS pH 7.3 (Oxoid, Cat. nr. BR0014G) and 0.05% (v/v) Tween® 20 (Sigma, Cat. nr. P9416). Purified IgG samples were titrated in three fold serial dilutions starting at 500 nM final concentration and incubated with biotinylated human PD1-His/AviTag at 0.6 nM final concentration for 20 minutes at room temperature. The parental IgG at 0.3 nM and the anti-human IgG1 Acceptor beads at 20 µg/ml (final concentrations) were added and the mix was incubated for 1 hour at room temperature. Followed by addition of the Streptavidin Donor beads at 20 µg/ml (final concentration) and incubation for 30 minutes at room temperature. The emission of light was measured in the EnVision multilabel plate reader (Perkin Elmer) and analysed using the EnVision manager software. Values were reported as Counts Per Second (CPS) and corrected for crosstalk.

Flow Cytometry of IgGs

Purified IgGs were tested in FACs for binding to CHO-K1 stable cell lines expressing human (Genscript, Cat. nr. M00529), and cyno (Genscript, Cat. nr. M00572) PD1, and CHO-K1 wild-type cells. The IgG samples were titrated in three-fold serial dilutions starting from 500 nM to 0.98 nM. Binding of IgGs was detected with a mouse anti-human IgG conjugated to FITC. Results were analyzed by examining the Mean Fluorescence Intensity (MFI) of 10000 cells per sample in the BL-1 channel detector of a flow cytometer (Attune™ NxT Acoustic Focusing Cytometer, Invitrogen/ThermoFisher Scientific). The EC50 values were calculated using the MFI values in GraphPad Prism software (GraphPad Software, La Jolla, Calif.) and 4 parameters.

PD1/PD-L1 Cell-Based Antagonism Assay

The PD1/PD-L1 blockade cell-based bioassay (Promega), was used to measure the potency of antibodies in blocking the PD1/PD-L1 interaction. On the day before the assay, PD-L1 aAPC/CHO-K1 cells were thawed and transferred into cell recovery medium (90% Ham's F12/10% FBS). The cell suspension was dispensed to each of the inner 60 wells of two 96-well, white, flat-bottom assay plates, at 100 µl per well. Cell recovery medium was added to each of the outside wells and the assay plates and incubated overnight at 37° C./5% CO2. On the day of the assay the sample IgGs were diluted 4-fold in assay buffer (99% RPMI 1640/1% FBS) from 300 nM to 0.04 nM and 40 µl per dilution added to the assay plates containing the PD-L1 aAPC/CHO-K1 cells. Positive inhibition controls included the human PD1 Antibody AF1086 (R&D systems), mu317 in IgG1null form and a pembrolizumab mab analogue in IgG1null form. As a negative inhibition control, an irrelevant IgG was included. PD1 Effector Cells were then thawed in assay buffer (99% RPMI 1640/1% FBS) and the cell suspension added to the wells of the assay plates containing the PD-L1 aAPC/CHO-K1 cells and the IgG titration samples. The assay plates were incubated for six hours in a 37° C./5% CO2 incubator, allowed to equilibrate to ambient temperature for 5-10 minutes, then 80 µl of Bio-Glo™ Reagent (Promega) was added. Assay plates were incubated at ambient temperature for a further 5-30 minutes and luminescence signals subsequently measured at 10, 20 and 30 minutes.

Allogeneic Mixed Leucocyte Reaction (MLR) Assay

Human PBMCs from healthy donors were prepared from buffy coats. Immature monocyte-derived dendritic cells (Mo-DCs) were prepared by isolating CD14+ cells using magnetic-activated cell sorting (MACs, Stemcell) and cultured with differentiation medium (Miltenyi) for 7 days. At the end of this 7-day period the Mo-DCs were classed as 'immature' and are ready to use in an immature MLR. Responder T cells (using cryopreserved PBMCs) were prepared on the day required, from a different donor to that used for the Mo-DCs, using a T cell isolation kit (Stemcell). Under each experimental condition (immature and MoDCs) 6 separate MLRs were performed to provide biological variation, all conditions were prepared in technical triplicate. Cells were co-cultured: $1 \times 10^4$ Mo-DC and $1 \times 10^5$ CD4+ T cell per well +/− test IgG antibodies for 4 days. Single cell type (T cell/Mo-DC) controls were included in each assay. Supernatants were collected at the end of culture period and assessed for IFN-γ by ELISA.

Charge Variant Analyses

Charge variant profiling of test articles was determined by Protein Charge Variant Assay on a LabChip GXII Touch HT (Perkin Elmer, Beaconsfield, UK), according to the manufacturer's protocol.

DSC Analyses

The Tm of test articles was analysed using a MicroCal PEAQ-DSC (Malvern Instruments, Malvern, UK) running version 1.22 software. The samples were heated at a rate of 200° C./hour over a range of 20–110° C. Thermal data was normalised based on protein concentration. The Tm of the protein was determined from the heating scan data.

Forced Oxidation Analyses

For forced oxidation analysis, test articles in PBS were treated with 0.5% H2O2 at room temperature for 2 hours and then stored at −80° C. prior to SEC, HIC and RP analysis (intact antibodies and subunits) on a Dionex Ultimate 3000RS HPLC system (ThermoFisher Scientific, Hemel Hempstead, UK), as detailed below. For intact antibody reduction, DTT was added to a final concentration of 0.33 M and samples were incubated for 1 hour at room temperature and immediately analysed by RP.

RP analysis of intact antibodies and subunits—Chromatographic separation was performed using a PLRP-S 1000, 5 µm, 2.1 mm×50 mm column (Agilent Technologies, Stockport, UK) connected to a Dionex Ultimate 3000RS HPLC system (ThermoFisher Scientific, Hemel Hempstead, UK). The method consisted of a linear gradient from 75% buffer A (0.075% TFA, 7.5% acetonitrile in H2O) to 50% buffer B (0.075% TFA, 7.5% H2O in acetonitrile) for mAbs 1-4, or 90% buffer B for mAb 5, over 24 minutes. The flow rate was 0.5 mL/minute and the temperature was maintained at 70° C. throughout the analysis. Detection was carried out by UV absorption at 280 nm.

SEC Analysis—Chromatographic separation was performed using an Acquity UPLC Protein BEH SEC Column, 200 Å, 1.7 µm, 4.6 mm×150 mm (Waters, Elstree, UK) and an Acquity UPLC Protein BEH SEC guard column 30×4.6 mm, 1.7 µm, 200 Å (Waters, Elstree, UK) connected to a Dionex Ultimate 3000RS HPLC system (ThermoFisher Scientific, Hemel Hempstead, UK). The method consisted of an isocratic elution over 15 minutes and the mobile phase was 0.2 M potassium phosphate pH 6.8, 0.2 M potassium chloride. The flow rate was 0.25 mL/minute. Detection was carried out by UV absorption at 280 nm.

HIC Analysis—Chromatographic separation was performed using a TSKgel Butyl-NPR 4.6 mm×35 mm HIC column (TOSOH Bioscience Ltd., Reading, UK) connected to a Dionex Ultimate 3000RS HPLC system (ThermoFisher Scientific, Hemel Hempstead, UK). The method consisted of a linear gradient from 60% Buffer A (100 mM sodium phosphate pH 7.0, 2 M ammonium sulphate) to 90% Buffer B (100 mM sodium phosphate pH 7.0) over 9 minutes. The flow rate was 1.2 mL/minute. Detection was carried out by UV absorption at 280 nm.

Antibody v-Domain Specificity Testing: Human Receptor Array Analyses

Human cell membrane receptor proteome arrays were performed at Retrogenix Ltd. Primary screens: 2 µg/ml of each antibody was screened for binding against fixed HEK293 cells/slides expressing 5528 human plasma membrane and tethered secreted proteins individually. All transfection efficiencies exceeded the minimum threshold. Antibody binding was detected using AF647 fluorescent secondary anti-human IgG1 antibody. Primary hits (duplicate spots) were identified by analysing fluorescence (AF647 and ZsGreen1) on ImageQuant. Confirmation/specificity screens: Expression vectors encoding ZsGreen1 only, or ZsGreen1 and CD20, PD1, BTN2A1, or LSAMP were transfected into human HEK293 cells. Each live transfectant was incubated with 2 µg/ml of each of the test antibodies, the positive control antibody Rituximab, or no primary antibody. Cells were washed, and incubated with the same AF647 anti-human IgG Fc detection antibody as used in the cell microarray screens. Cells were again washed, and analysed by flow cytometry using an Accuri flow cytometer (BD). A 7AAD live/dead dye was used to exclude dead cells, and ZsGreen1-positive cells (i.e. transfected cells) were selected for analyses.

Results and Discussion

CDR Grafting onto Preferred Human Germline v-Genes

The CDRs of an agonistic murine anti-PD1 IgG Mu317 (WO2015/035606 A1 and Table 2) were initially introduced to human germline immunoglobulin v-domain framework sequence scaffolds using CDR grafting. To bias our engineering efforts towards final lead therapeutic IgG compounds with optimal drug-like properties, we chose to graft the CDRs of the parental antibody onto "preferred" germline scaffolds IGHV3-7 and IGKV4-1, which are known to have good solubility and drug development qualities, and are used at high frequency in the expressed human antibody repertoire.

Those scaffolds and grafted CDR definitions are outlined in Table 2. The heavy and light chain sequences for hu317 anti-PD1 antibody are also shown in Table 2. While this process of CDR grafting is well known, it is still problematic to predict whether a given set of human v-domain sequences will act as suitable acceptor frameworks for non-human CDR grafting. The use of unsuitable frameworks can lead to the loss of target binding function, protein stability issues or even impaired expression of the final IgG. The IGHV3-7/IGKV4-1 graft was therefore taken forward as the template for CDR mutagenesis and selection of improved clones.

Library Generation and Screening

The CDR-grafted IGHV3-7/IGKV4-1 v-domain sequences were combined into a Fab phage display format and a mutagenesis library cassette was generated by oligo synthesis and assembly. Two separate Fab libraries were initially constructed that sampled mutational diversity in either the heavy or light chain v-domain sequences in combination with the cognate paired grafted v-domain. Both VH and VL libraries were separately ligated into a phage display vector and transformed into $E.\ coli$ via electroporation to generate $3.15 \times 10^9$ and $2.27 \times 10^9$ independent clones, respectively. Library build quality was verified by sequencing 96 clones per library. This sequencing data showed that the positions encoding either the murine or human germline residue at each position of variance had been effectively sampled at a frequency of approximately 50% and that positions sampled with non-binary amino acid content sampled the position in question with the intended amino acids. Libraries were rescued using helper phage M13 and selections performed on biotinylated human and cynomolgus monkey PD1-Fc proteins. After an initial round of selection, the two pools of mutated VH and VL domains were recombined into a secondary library and three further rounds of standard selection, plus two 'hammer-hug' rounds performed.

Figure 1B:
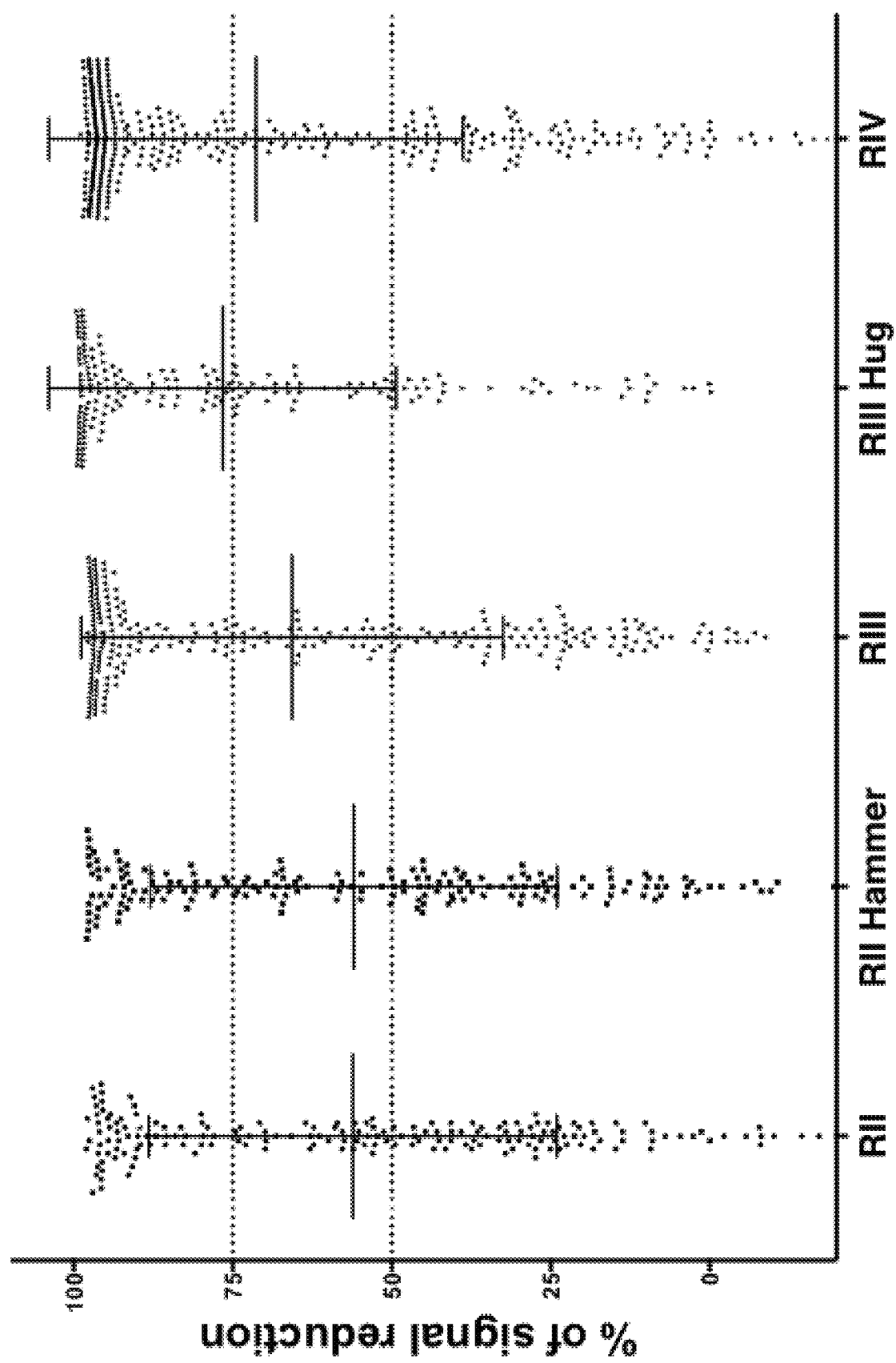

Post-selection screening (FIG. 1A, 1B) and DNA sequencing revealed the presence of 712 Fab clones that exhibited strong binding to human and cyno PD1 in ELISA and >50% inhibition of Mu317 IgG1 binding to human and cyno PD1 in Alphascreen assay. Amongst these 712 clones, germlining mutations were observed in all CDRs (Table 3). Lead clones were ranked based on level of CDR germ-lining versus ELISA signals for binding to both human and cyno PD1-Fc. The v-domains of the 7 top clones from this ranking were then sub-cloned into IgG expression vectors for further testing as below (Table 4).

Figure 2A:
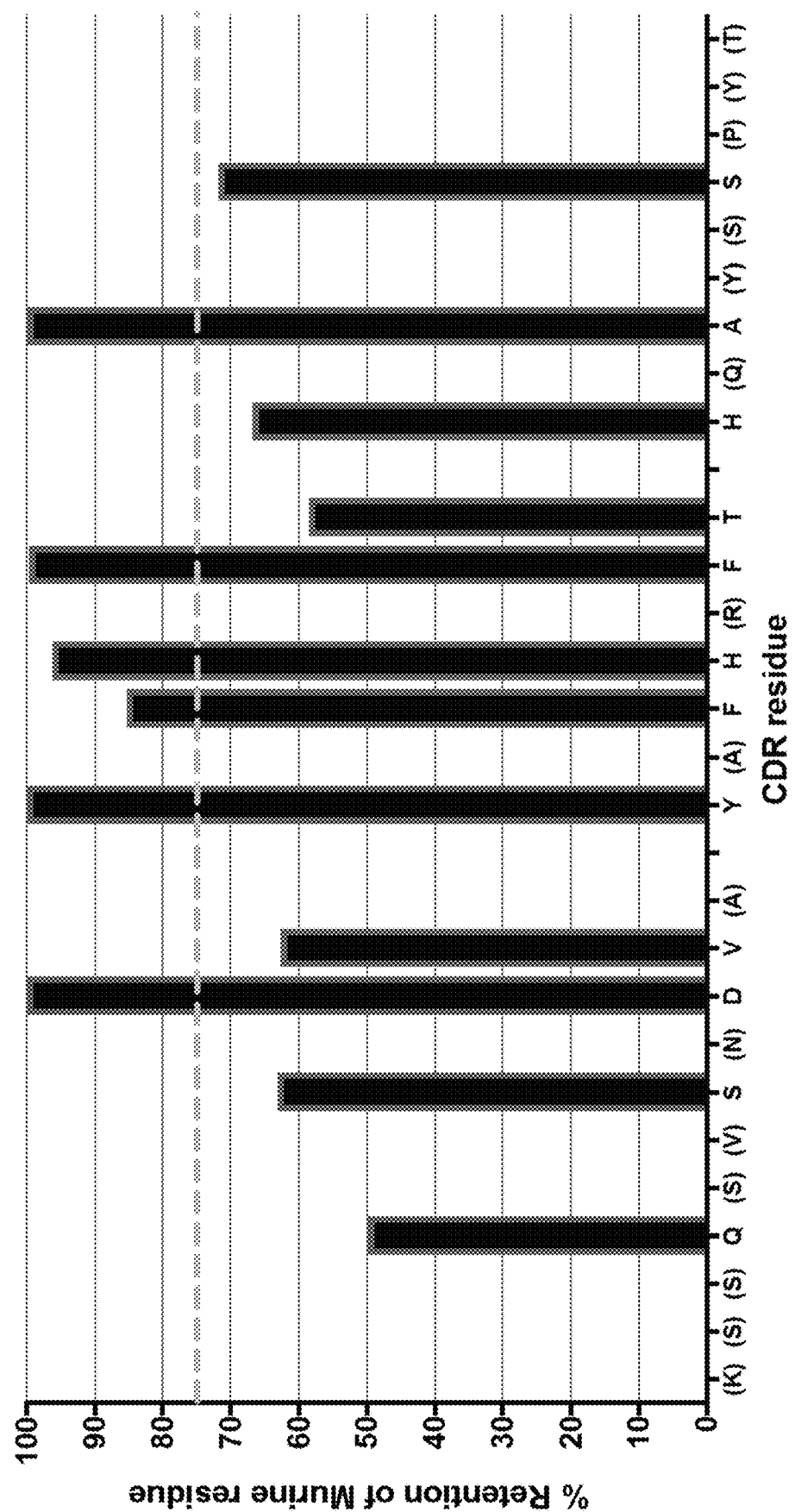
FIG. 2A-FIG. 2B. Analysis of CDR residue tolerance for mutation to germline. A plot of murine amino acid retention frequencies in the CDRs of the ELISA-positive population of 712 unique scFv clones is shown for $V_L$ (SEQ ID NOs: 409-411) (FIG. 2A) and $V_H$ (SEQ ID NOs: 412-414)(FIG. 2B) domains, respectively. Only those residues targeted for human/murine residue mutagenesis are plotted, other than in the HCDR3. CDR residues noted in parentheses on the X-axes were identical to those found in the human germlines used for grafting (IGKV4-1 and IGHV3-7). In both plots the dashed line in grey at 75% represents the cut-off for tolerance of murine residue replacement by human germline.
Figure 2B:
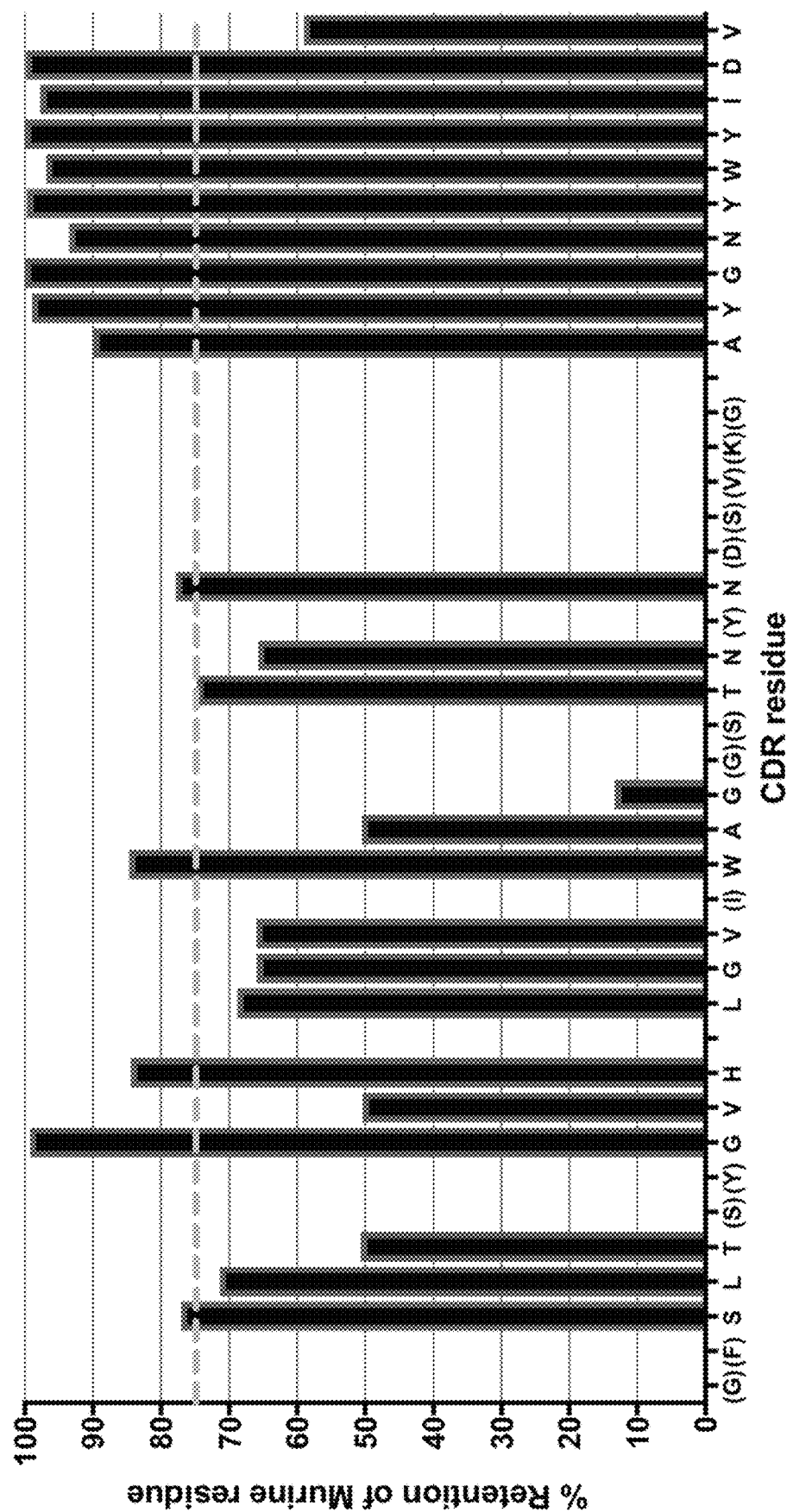

While germ-lining mutations were observed in all CDRs for the lead clones derived directly from library selections, it remained possible that sequence analyses might allow further clones to be designed to have maximal humanization. The 712 hits with binding signals against human and cyno protein were therefore used to analyse the retention frequency for murine amino acids in the CDRs of this functionally characterized population. Positional amino acid retention frequency was expressed as a percentage found in the $V_L$ and $V_H$ domains (FIG. 2A, 2B). Murine residues with RF<75% were regarded as positions that are possibly not essential to the target-binding paratope and are likely to be open to germ-lining, in a series of combinatorial designs (Table 4). In the $V_H$ domain (excluding the CDR-H3), only 5 of 15 murine residues in the CDR-H1 and H2 exhibited retention frequency above 75% (FIG. 2B). In the $V_L$ domain, only 6 of 12 murine CDR residues derived from the Mu317 sequence were retained with frequencies >75% (FIG. 2A). This analysis strongly suggested that the LCDR1 and LCDR3 sequences could be rendered close to germline identity to IGKV4-1.

Designs containing combination of those murine residues with RF>75% were given the prefix "MH" (MH=Maximally Humanized). In total 12 initial designer $V_H$ and $V_L$ designer domain combinations were generated: MH1-MH12 (Table 4). The MH clones were generated by gene synthesis and (along with the 7 library-derived clones outlined above and positive controls Mu317 and hu317), cloned into human expression vectors for production in IgG1null format. All IgGs were readily expressed and purified from transient transfections of mammalian cells.

Lead IgG Specificity and Potency Characteristics

Figure 3A:
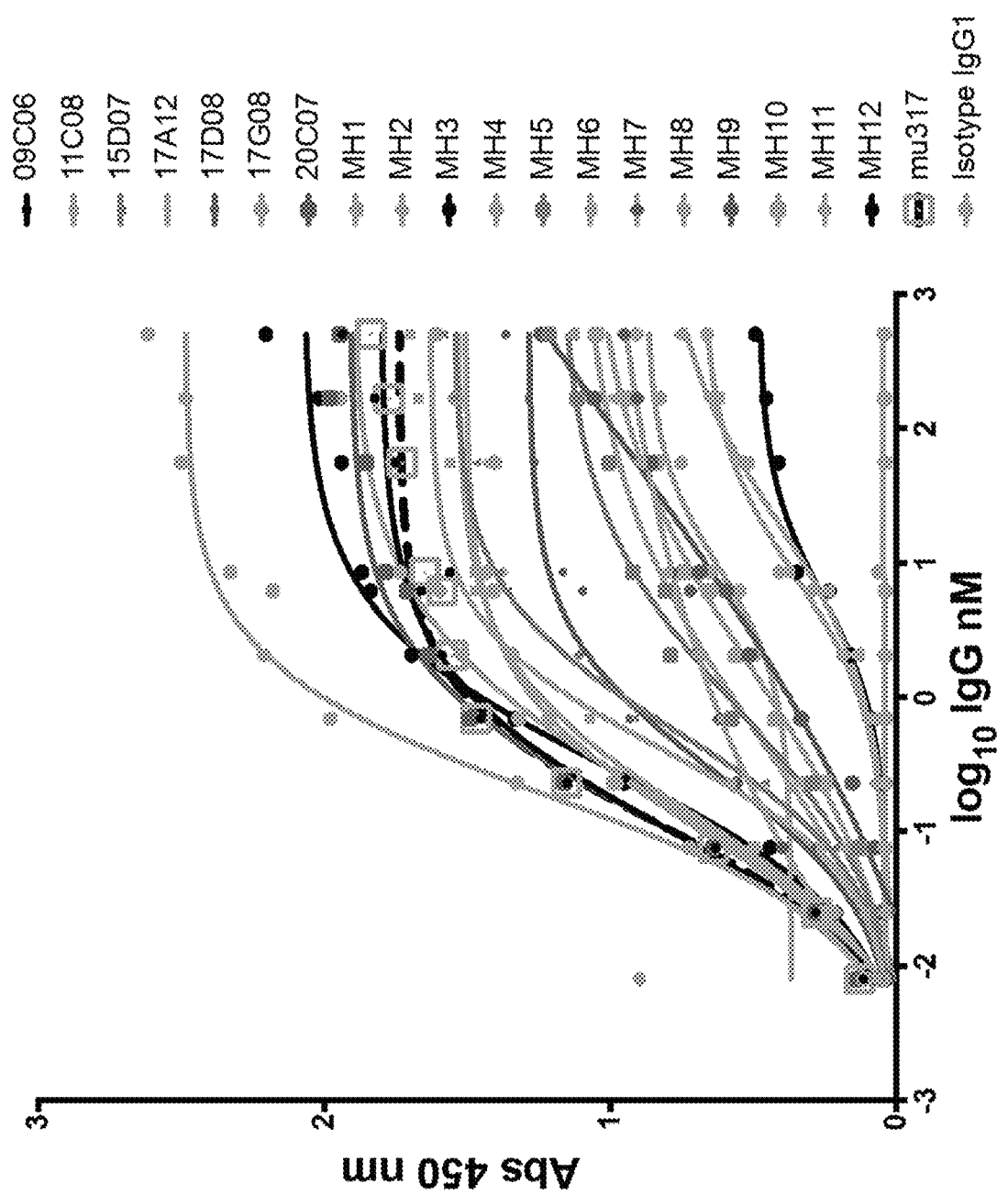
FIG. 3A-FIG. 3B. Direct titration ELISA for library-derived IgG1null clones binding to human and cyno PD1-Fc proteins. Mu317 and library-derived IgGs were titrated (in nM) in a direct binding ELISA against human (FIG. 3A) and cyno (FIG. 3B) PD1-Fc proteins.
Figure 3B:
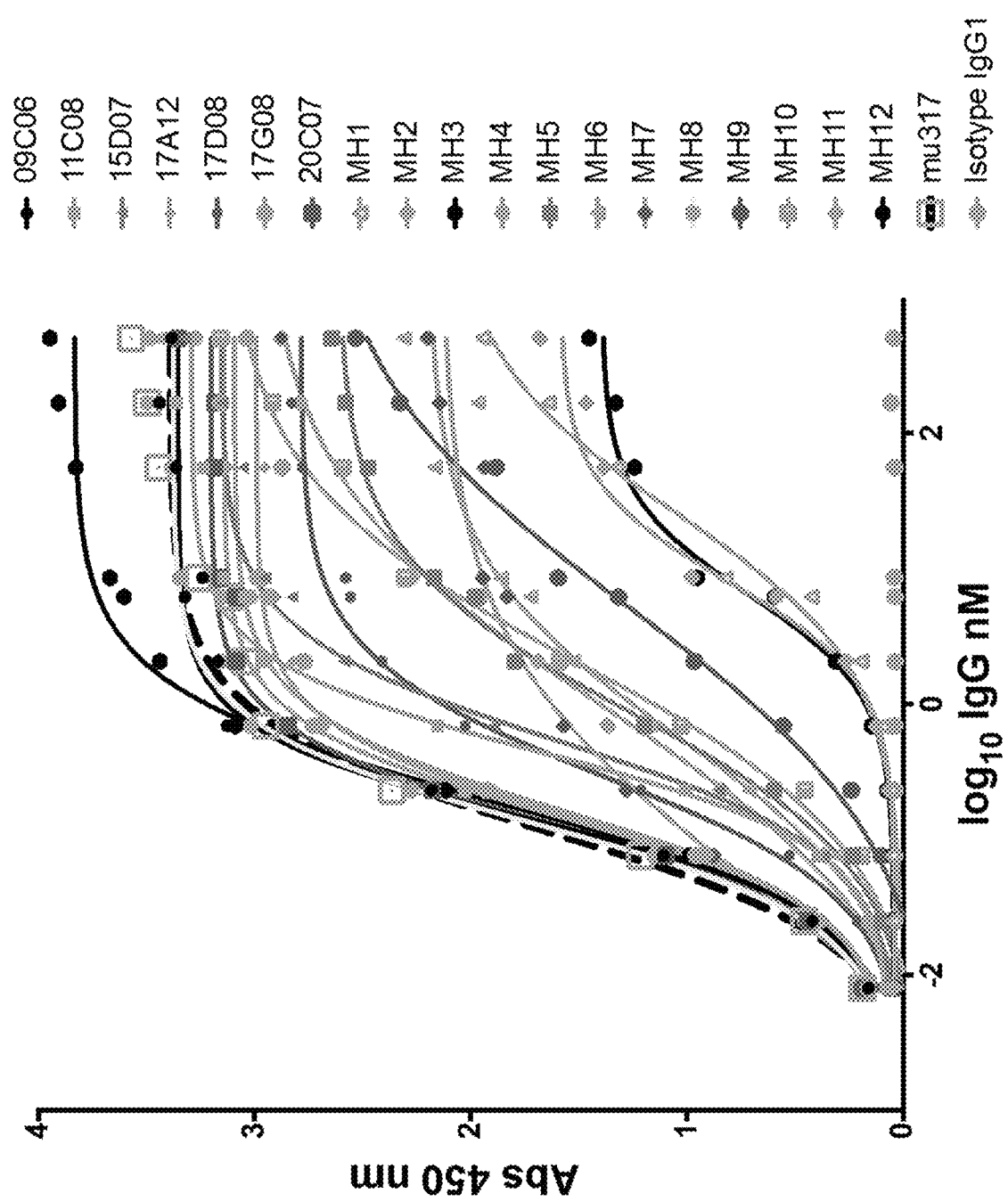

The purified IgGs described above were then tested for binding to human and cyno PD1-Fc in direct titration ELISA format. This analysis demonstrated that all library-derived clones and a select subset of designer clones (MH4, MH8, MH12) had human and cyno PD1 binding profiles similar to, or improved over, Mu317 (FIG. 3A, 3B). The majority of designer clones (MH1, MH2, MH3, MH5, MH6, MH7, MH9, MH19, MH11) exhibited reduced binding to one or both orthologs of PD1, demonstrating that the mutations found in these clones are disruptive to binding when used in combination. This finding highlighted the inability to predict precisely which combinations of mutations will lead to an optimal outcome, even in the possession of the mutational map outlined in FIGS. 2A and 2B.

An Alphascreen assay was established to allow the testing of designer IgGs for PD1 binding affinity and epitope competition with mu317 IgG binding to biotinylated monomeric human PD1. In this assay, while all 3 clones exhibited full epitope competition with Mu317, clone MH8 exhibited an IC50 value closest to mu317 (mu317—0.37 nM, MH8—0.39 nM, MH12 0.624 nM, MH4, 0.630 nM).

Figure 4A:
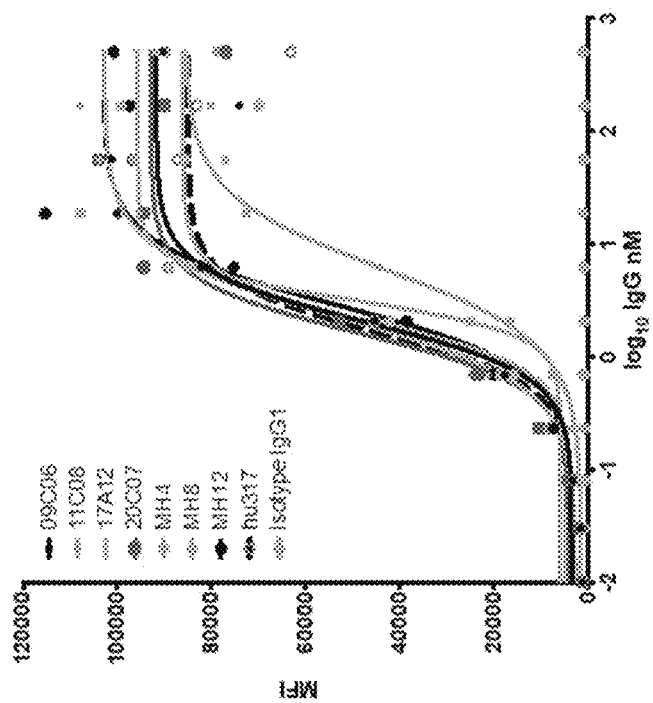
FIG. 4A-FIG. 4B. Flow cytometric binding to human and cyno PD1+CHO cells. Mu317, lead library-derived and designer IgGs were examined for specific binding on human (FIG. 4A) and cyno (FIG. 4B) CHO cells expressing human PD1. Concentration-dependent binding was observed against human PD1 for all clones, with no binding being observed for Isotype control IgG1. No binding signal was observed for any clone against untransfected CHO cells.
Figure 4B:
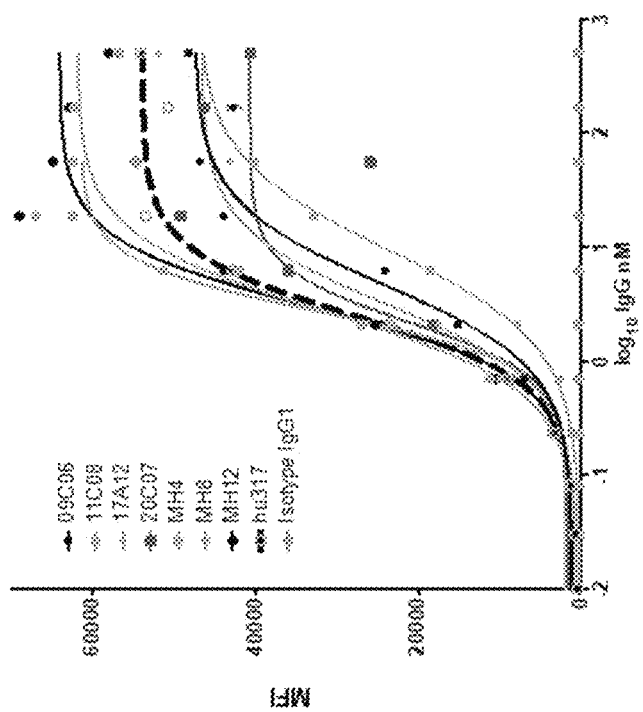

Flow cytometric analyses of lead IgG binding specificity at the cell membrane Antibodies to PD1 were analysed for concentration-dependent binding at the cell surface via flow cytometry. Initial analyses were performed on CHO cells stably-transfected with human or cyno PD1. These analyses showed that lead library-derived and designer clones exhibit concentration-dependent binding to membrane-presented human or cyno PD1 (FIG. 4A, 4B) with potencies similar to, or improved over, the hu317. No binding signals were observed for any clone, even at the highest concentrations, on untransfected CHO cells.

Lead IgG Analyses in PD1-PDL1 Blockade Assay

Figure 5:
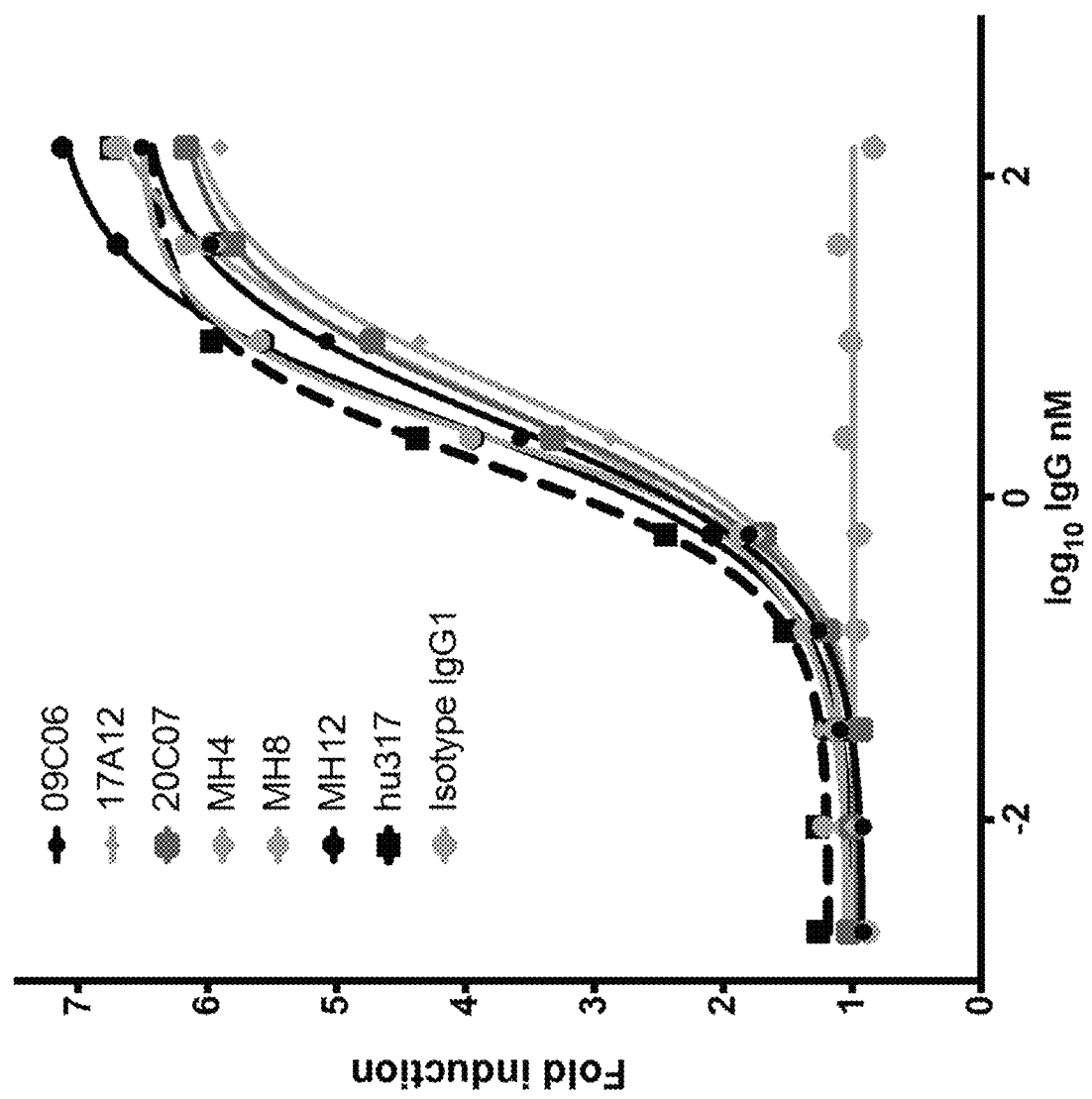
FIG. 5. Cell-based PD1/PD-L1 antagonism assay. Analyses of antagonism of human PD1 function at the cell surface, for multiple lead clones in human IgG1null format, showed that all novel clones exhibited strong, concentration-dependent, antagonistic activity.
Figure 6C:
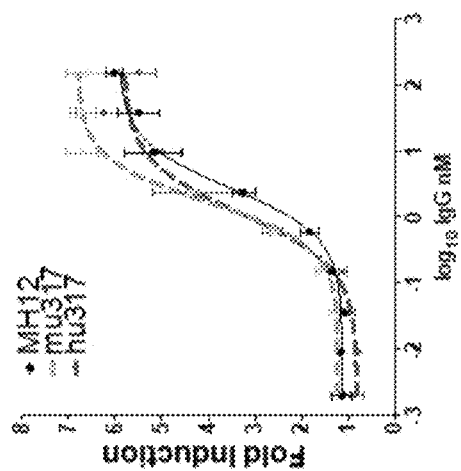
FIG. 6A-FIG. 6C. Cell-based PD1/PD-L1 antagonism assay for maximally humanized lead clones MH4, MH8 AND MH12 versus mu317 and hu317. Analyses of antagonism of human PD1 function, for multiple lead clones in human IgG1null format. These analyses showed that clones MH4 (FIG. 6A), MH8 (FIG. 6B) and MH12 (FIG. 6C) exhibited antagonistic potency overlapping with both mu317 and hu317. Values expressed as Mean±SD fold induction.
Figure 6B:
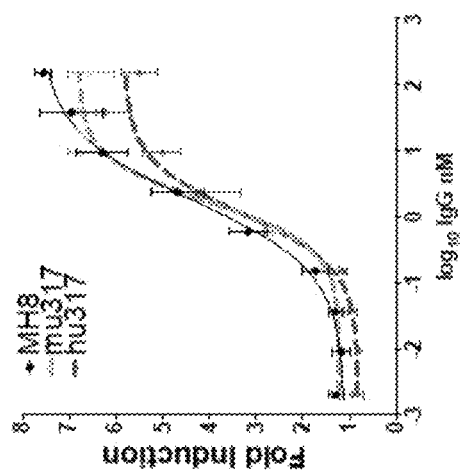
Figure 6A:
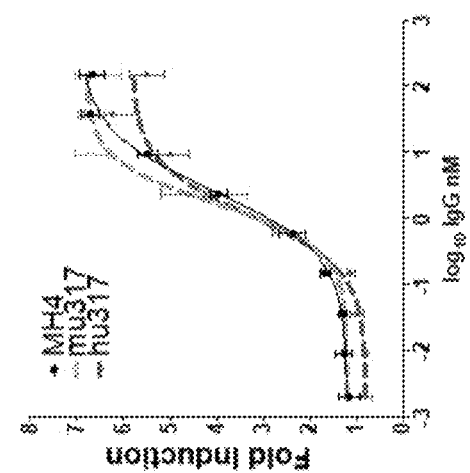

In a cell-based PD1/PD-L1 blockade reporter assay, all clones tested exhibited concentration-dependent antagonism of PD1. Lead clones MH4, MH8, MH12, 09C06, 17A12 and 20007 demonstrated fold induction curves and maximal signal values highly similar to mu317 (FIG. 5). Maximally humanized clones MH4, MH8 and MH12 (FIG. 6A, 6B, 6C, respectively) were then re-examined in this assay, being run alongside both mu317 and hu317 IgG1. These analyses showed that these three clones had fully maintained the potency of both mu317 and hu317, with concentration-dependent fold induction curves that are overlapping.

Antibody v-Domain T Cell Epitope Analyses

In silico technologies (Abzena, Ltd.), which are based on identifying the location of T cell epitopes in therapeutic antibodies and proteins, were used for assessing the immunogenicity of both the Hu317 and lead antibody v-domains. Analysis of the v-domain sequences was performed with overlapping 9mer peptides (with each overlapping the last peptide by 8 residues) which were tested against each of the 34 MHC class II allotypes. Each 9mer was scored based on the potential 'fit' and interactions with the MHC class II molecules. The peptide scores calculated by the software lie between 0 and 1. Peptides that produced a high mean binding score (>0.55 in the iTope™ scoring function) were highlighted and, if >50% of the MHC class II binding peptides (i.e. 17 out of 34 alleles) had a high binding affinity (score >0.6), such peptides were defined as 'high affinity' MHC class II binding peptides which are considered a high risk for containing CD4+ T cell epitopes. Low affinity MHC class II binding peptides bind a high number of alleles (>50%) with a binding score >0.55 (but without a majority >0.6). Further analysis of the sequences was performed using the TCED™. The sequences were used to interrogate the TCED™ by BLAST search in order to identify any high sequence homology between peptides (T cell epitopes) from unrelated proteins/antibodies that stimulated T cell responses in previous in vitro T cell epitope mapping studies performed at Abzena Ltd.

Peptides were grouped into four classes: High Affinity Foreign ('HAF'—high immunogenicity risk), Low Affinity Foreign ('LAF'—lower immunogenicity risk), TCED+ (previously identified epitope in TCED™ database), and Germline Epitope ('GE'—human germline peptide sequence with high MHC Class II binding affinity). Germline Epitope 9mer peptides are unlikely to have immunogenic potential due to T cell tolerance, as validated by previous studies with a wide range of germline peptides. Importantly, such germline v-domain epitopes (aided further by similar sequences that are found in the human antibody constant regions) also compete for MHC Class II occupancy at the membrane of antigen presenting cells, reducing the risk of foreign peptide presentation being sufficient to achieve the 'activation threshold' required for T cell stimulation. High GE content is therefore a beneficial quality in clinical development of an antibody therapeutic.

Figures 7A, 7B, 7C, 7D:
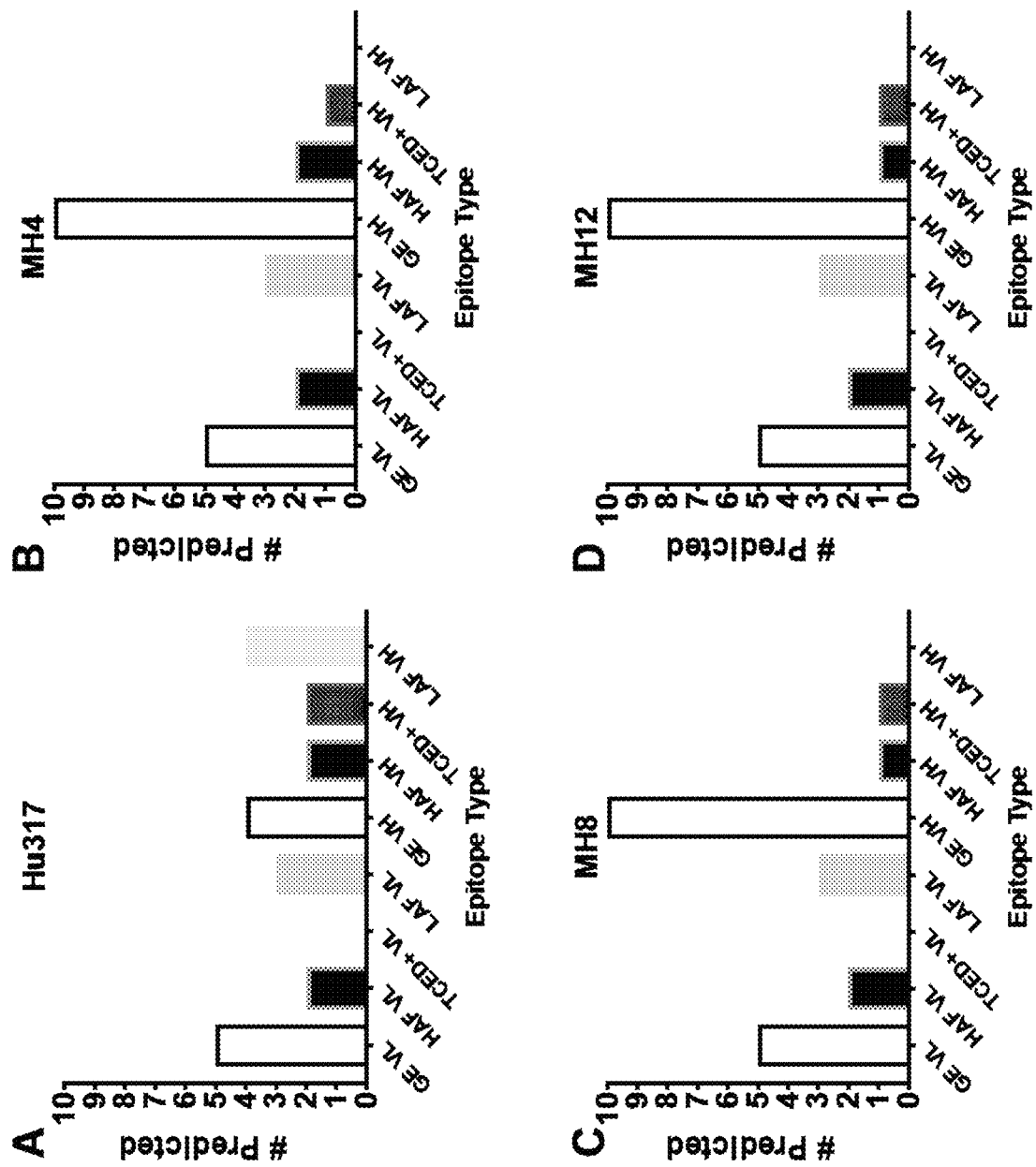
FIG. 7A-FIG. 7H. T cell epitope peptide content in lead antibody v-domains. The v-domains of Hu317 and multiple lead antibodies were examined for the presence of Germline (GE), High Affinity Foreign (HAF), Low Affinity Foreign (LAF) and TCED+ T cell receptor epitopes. Both the VH and VL domains of Hu317 were found to contain multiple high-risk human T cell epitopes and few germline epitopes. In all lead clones, the high-risk epitope content was significantly reduced and germline epitope content significantly improved.
Figures 7E, 7F, 7G, 7H:
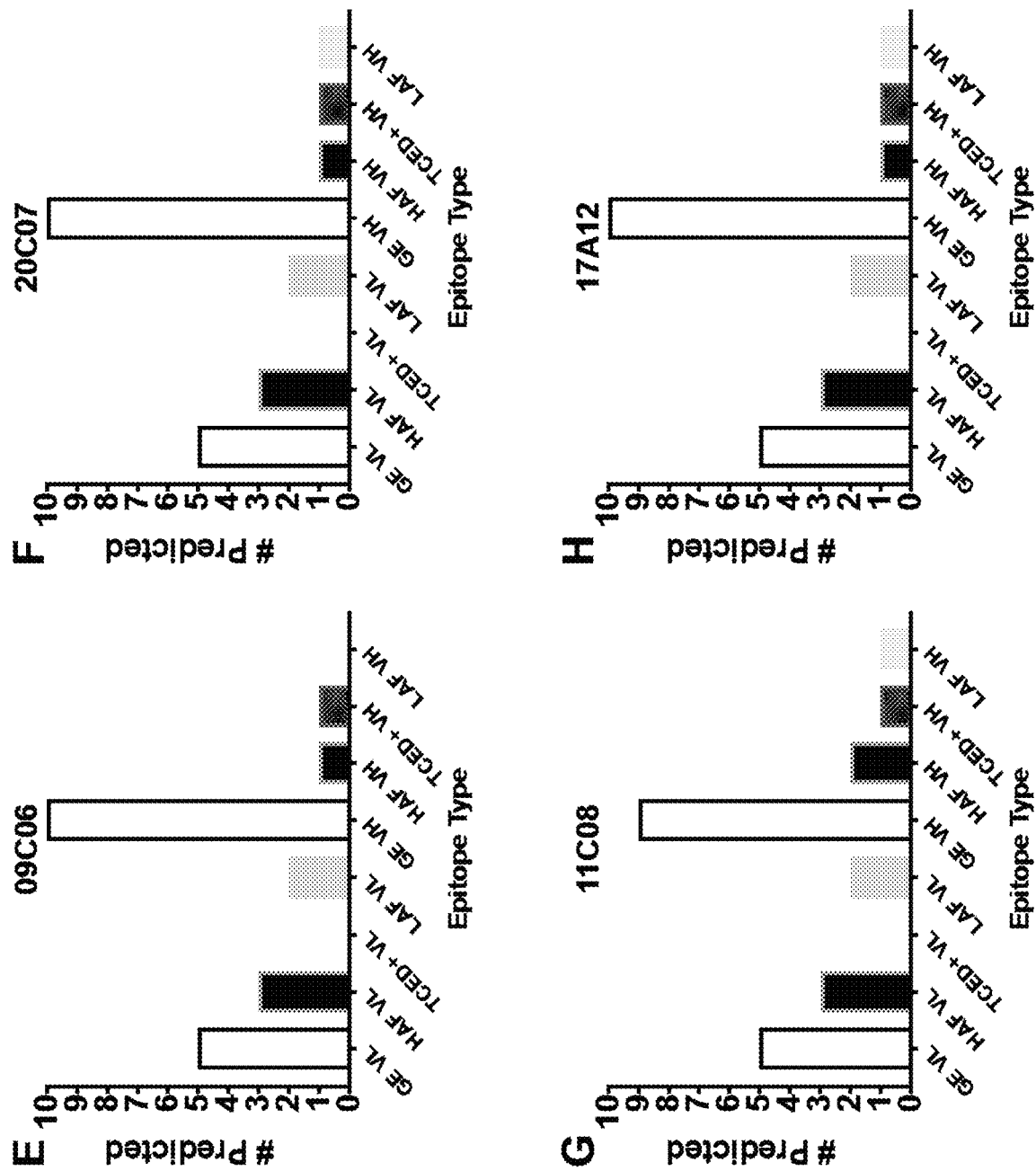

As shown in FIG. 7 and Table 5, key lead v-domains exhibited significant beneficial changes in peptide epitope content in comparison to Hu317. As the v-domain engineering process undertaken here had successfully selected for antibodies that maintained anti-PD1 potency while humanizing a significant number of the murine residues included in the CDRs of Hu317 (Table 2), multiple HAF and LAF epitopes found in the v-domains of Hu317 (FIG. 7A) were absent in library-derived and designer leads (Table 5). Unexpectedly, GE epitope content was found to be significantly increased (from 5 to ≥14 in all leads), particularly in the VH regions of lead clones (FIG. 7B-H), and TCED+ epitopes were reduced in all leads (Table 5). The marked improvements in immunogenicity risk in the VH domain were mediated specifically by adapting the CDRs of Hu317 to fit the IGHV3-7 germline, which we have now shown (for the first time) contains more GE epitopes in its frameworks than are found in the IGHV4-4 VH grafted Hu317 frameworks. For example, the germlining of the last 7 residues of the HCDR2 sequence to match IGHV3-7 (YVDSVKG (SEQ ID NO:80) in all lead clones, Table 4) allowed a GE to be restored that spans the c-terminal HCDR2 and n-terminal framework 3 regions (VKGRFTISR (SEQ ID NO:81)). In addition, mutation of the HCDR1 sequence from 'GFSLTSYGVH' (SEQ ID NO:82) to the sequence 'GFTFSSYGMH' (SEQ ID NO:57) (found in clones 09C06, 17A12, 17D08, 17G08 and 15D07) not only ablated the LAF sequence 'LTSYGVHWI' (SEQ ID NO:83) which spans the HCDR1 and framework 2 regions of Hu317, but also rendered this CDR fully germline identity to the human v-genes IGHV3-33 and IGHV3-30-5. The HCDR1 sequence 'GFTFSSYGMS' (SEQ ID NO:33) (found in clones 20007 and all designer clones MH1-MH18, Table 4) also ablated the LAF sequence 'LTSYGVHWI' (SEQ ID NO:83). Both humanized CDR1 sequences encoded a GE peptide sequence 'YGM(H/S)WVRQA' (SEQ ID NO:84) that was not found in either Hu317 or the library-derived clone 11C08, due to the presence of the residue valine in their HCDR1s at position 9 (e.g. GFSLTSYG$\underline{V}$H (SEQ ID NO:82)).

Importantly, multiple foreign epitopes were also eliminated by germlining mutations found in the other CDRs of lead clones. For example, a TCED+ and LAF peptide 'YWYIDVWGQ' (SEQ ID NO:85) which spans the HCDR3 and framework 4 of Hu317 was eliminated in the majority of lead clones by the mutation V>R at position 6 (Table 4). Similarly, in clones MH1-MH18 and 09C06, the HAF peptide 'LEWIGVIYA' (SEQ ID NO:86) and LAF peptide 'IGVIYADGS' (SEQ ID NO:87) which are both found in Hu317 were simultaneously ablated by mutation of the residues 'IGV' to 'VAN' (Table 4, Table 5). A HAF peptide 'LEWVGVIWQ' (SEQ ID NO:88) was found in the VH domain of clone 11C08, which overlaps with the 'LEWIGVIYA' (SEQ ID NO:86) HAF from Hu317, while the LAF peptide 'IGVIYADGS' (SEQ ID NO:87) was ablated. In clone 17A12, the 'LEWIGVIYA' (SEQ ID NO:86) HAF from Hu317 was partially ablated, by mutation to the LAF peptide 'LEWLANIWQ'.

In the VL region of Hu317 and all leads, the total balance of GE versus foreign epitopes was not increased (FIG. 7, TABLE 5), despite the introduction of the mutations outlined above that ablated the oxidation risk in the LCDR2 by mutating the F at position 3 of the LCDR2 (YAFHRFT (SEQ ID NO:31)). In total, the immunogenicity findings outlined above demonstrated that through extensive, yet unpredictable germlining of multiple CDR positions in the VH domain (specifically into the IGHV3-7 framework), the lead antibodies achieved the removal of several significant high-risk human t cell epitope peptide sequences and acquired several GEs with the potential to reduce immunogenicity, greatly improving the ratio of GE to foreign epitopes.

Lead IgG Potency in MLR Assay

Figure 8A:
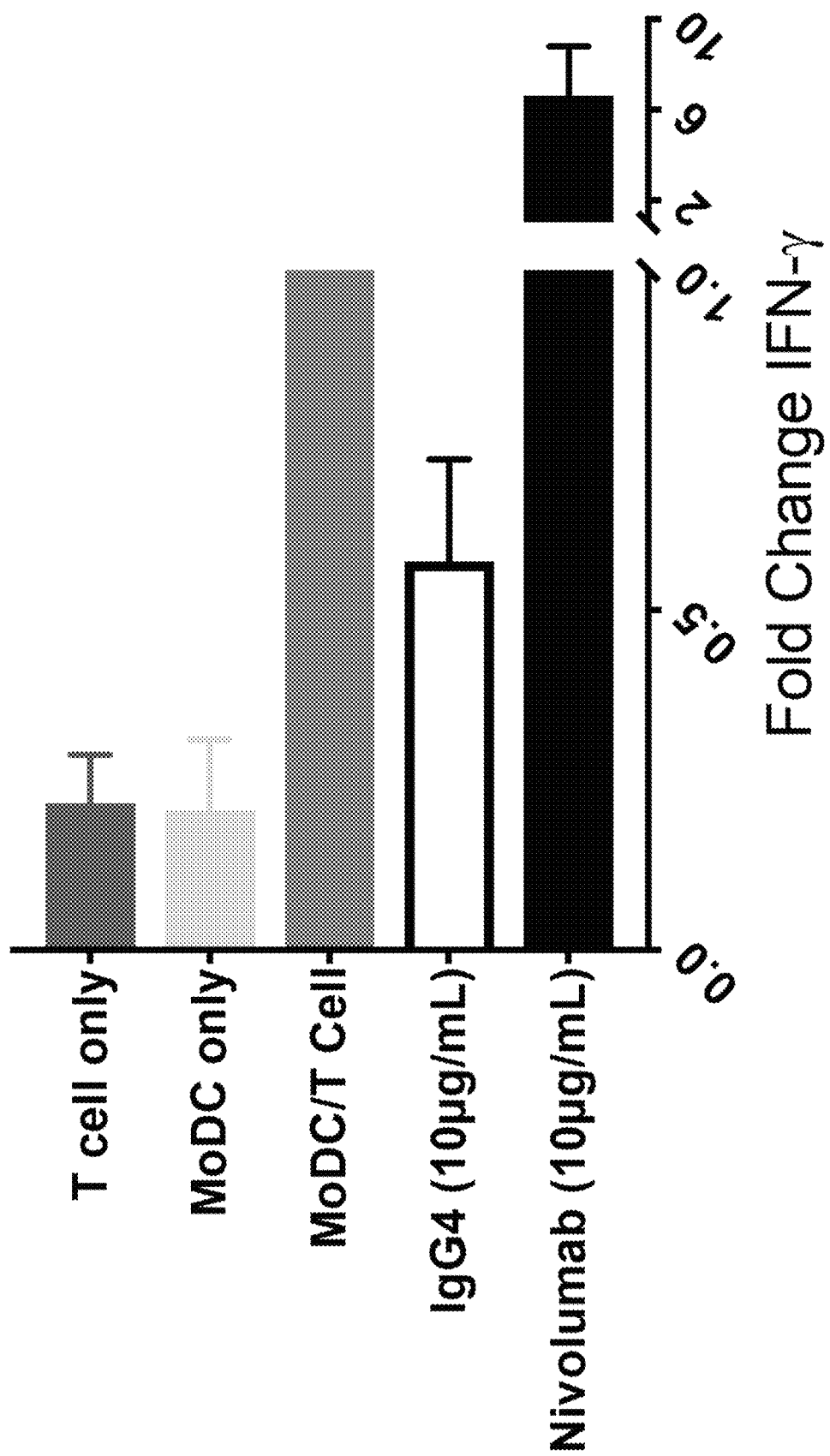
FIG. 8A-FIG. 8C. MLR cell-based PD1/PD-L1 antagonism assay. Effect of anti-PD1 IgGs on IFN-γ Production in an Allogeneic MLR assay. Control analyses (FIG. 8A), 3-point analyses for lead clones 09C06, MH4, MH8, MH12 (FIG. 8B), and multi-point analyses for clones MH4, MH8 and Hu317 (FIG. 8C) are shown. In each case, Isotype controls were used (human IgG4, or IgG1).

The aim of this study was to characterise the potency of lead PD-1 targeted antibodies in an human allogeneic MLR, by measurement of IFN-γ in the culture supernatants. In control conditions (FIG. 8A) the cytokine levels demonstrated that a Nivolumab analog significantly increased IFN-γ levels compared to isotype control human IgG4. Isotype showed no difference compared to cells only, and the single cell conditions showed little to no measurable cytokine.

Figure 8B:
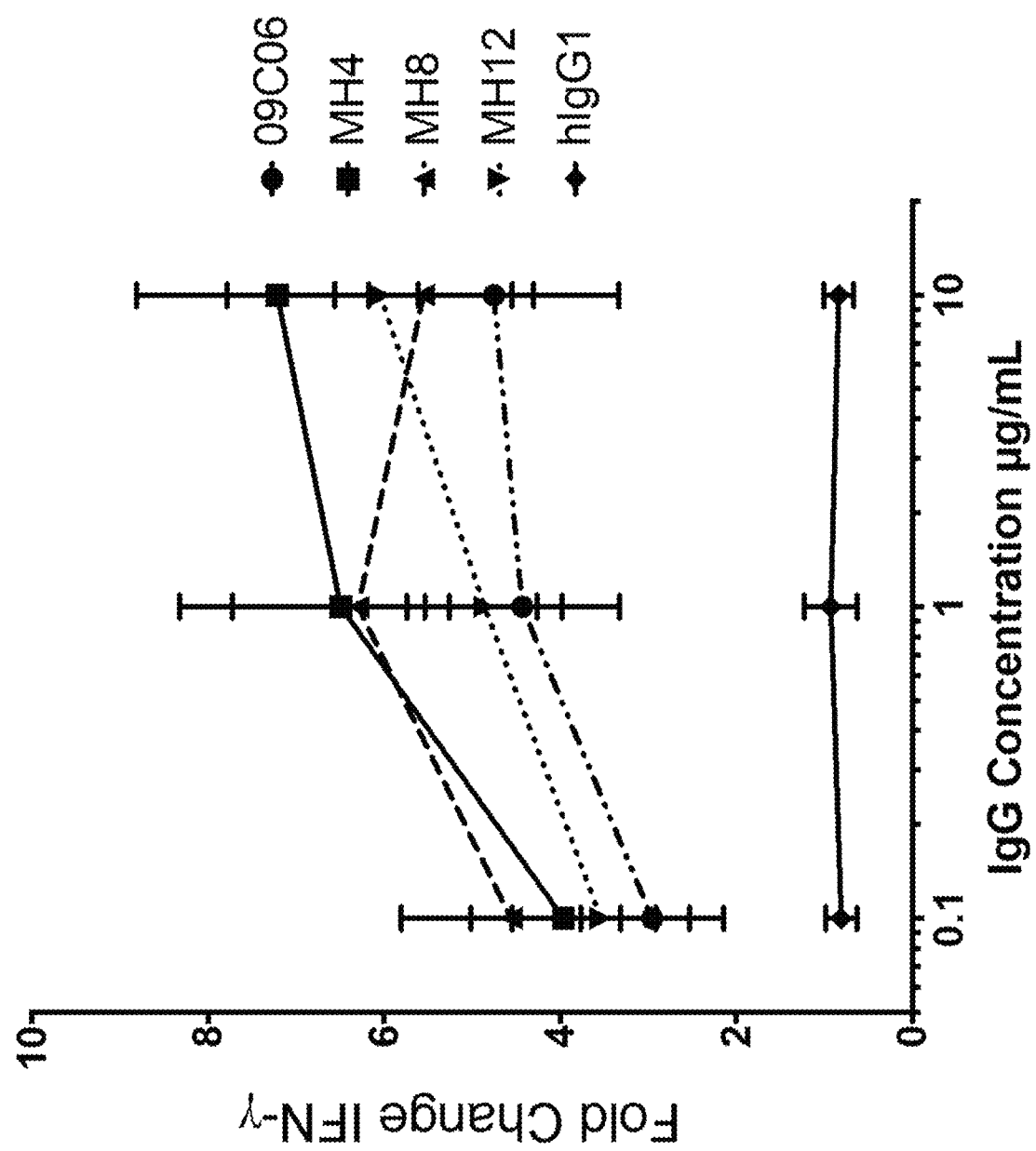
Figure 8C:
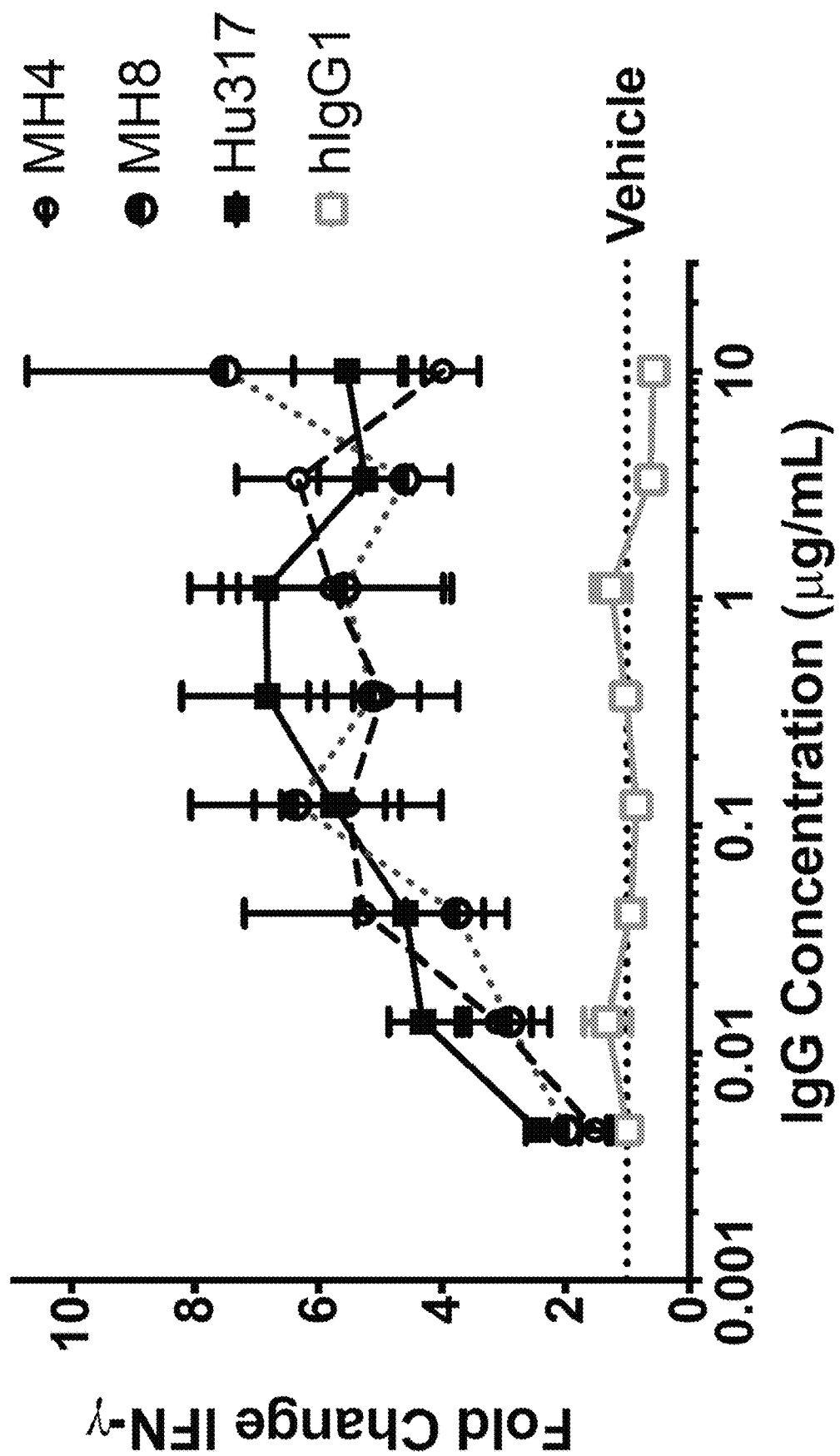

As all controls had demonstrated the expected signals, clones 09C06, MH4, MH8 and MH12 were examined for activity in the assay. The four test antibodies were used at three concentrations (0.1, 1 and 10 µg/mL) and compared to the appropriate isotype control, human-IgG1. All four test antibodies significantly increased IFN-γ production within the cell culture supernatants in a dose-dependent manner (FIG. 8B). The data shows that all four test antibodies provided could enhance IFN-γ production in an allogeneic MLR when compared to hIgG1. Finally, clones Hu317, MH4 and MH8 were tested in the assay across a wide concentration range (FIG. 8C). This analysis demonstrated that both clones MH4 and MH8 retained fully overlapping concentration-dependent activity with Hu317 in a relevant human ex-vivo potency assay.

Charge Variant Analyses

Charge heterogeneity analysis is used widely in the characterisation of monoclonal antibodies because it provides important information about product quality and uniformity. Heterogeneity can be caused by enzymatic post-translational modifications such as glycosylation, lysine truncation, oxidation or deamidation. Heterogeneity in IgGs is a manufacturing risk and can cause increased complexity in bioprocessing protocols.

Figure 9:
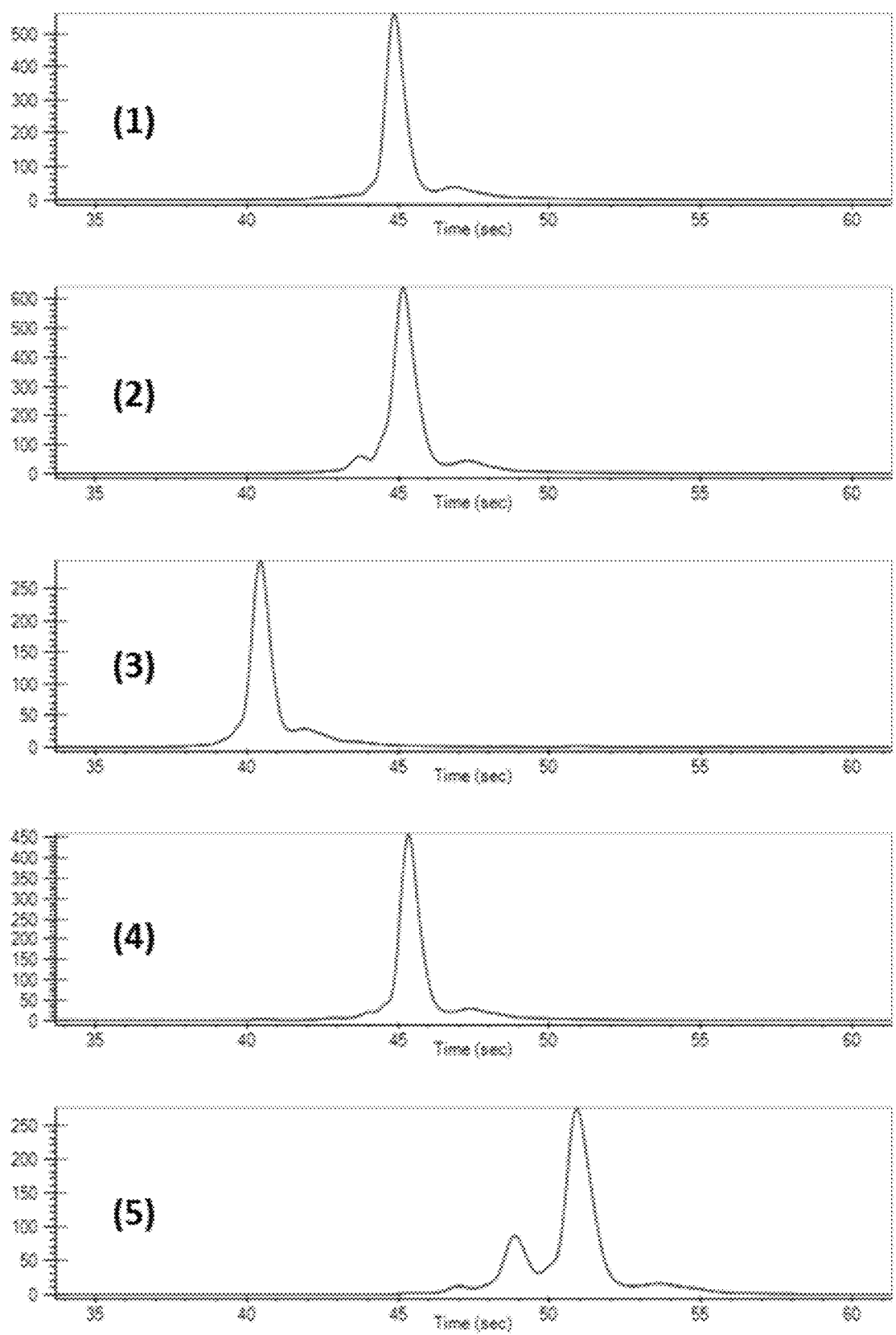
FIG. 9. Charge variant profiles of purified IgGs. (1) 09C06, (2) MH4, (3) MH8, (4) MH12 and (5) Hu317 are shown. Y axis signals measured in Fluorescence Units.

The Protein Charge Variant Assay allows identification of basic and acidic protein variants relative to the dominant product peak. The microfluidics chip technology resolves protein charge variants after fluorescent labelling. The charge variant profiles for 09C06, MH4, MH8 MH12 and hu317 IgGs are depicted in FIG. 9. All of mAbs 09C06, MH4, MH8 and MH12 display a highly homogeneous profile, with the main isoform comprising 77.4-82.8% of the total protein (Table 6). In contrast, however, Hu317 showed an unexpectedly more complex profile with 4 distinct peaks, a higher percentage of basic isoforms (23.1%) and with the main isoform representing <69% of total. These significant improvements in charge homogeneity for clones 09C06, MH4, MH8 and MH12 over Hu317 were not immediately explained by the removal of potential post-translational modification sites in the CDRs of the lead IgGs, as any potential o-link glycosylation, deamidation or isomerisation sites in the CDRs were maintained and no n-link glycosylation sites had been introduced (Tables 2 and 4). As such improved homogeneity could also be caused by improvements in thermal stability, or improved resistance to oxidation, we investigated those characteristics.

Thermal Stability Evaluation Using DSC

A protein's DSC profile provides information about its total structural stability, via its thermal stability, but can also represent a structural 'fingerprint' for assessing structural modifications. The thermogram of an intact antibody could present two or three peaks, with the largest peak containing the contribution from the Fab fragment. Usually the first transition covers the unfolding of the CH2 domain, while the last one would include the unfolding of the CH3 domain. The Fab unfolding could occur at a distinct temperature compared to the unfolding of CH2 and CH3 domains, but it is also possible that the Fab fragment unfolding 'buries' the unfolding of either CH2 or CH3 domains, resulting in peak overlap. As the constant domains are virtually identical for antibodies of the same subclass, the CH2 and CH3 domains should have comparable Tm, while the Fab's Tm will vary from antibody to antibody.

Figure 10:
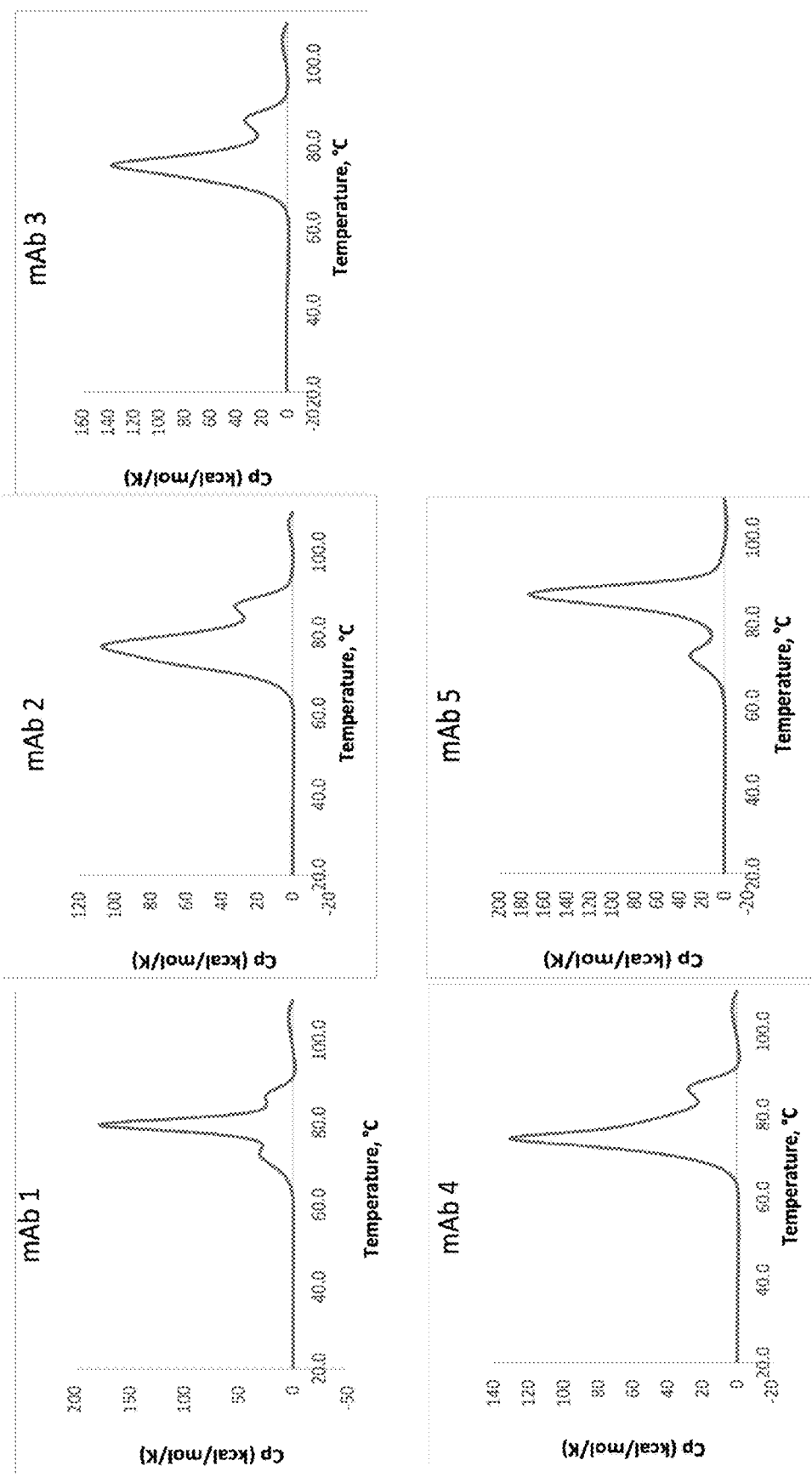
FIG. 10. DSC Thermograms of purified IgGs. (1) 09C06, (2) MH4, (3) MH8, (4) MH12 and (5) Hu317 are shown.

All five IgGs tested (09C06, MH4, MH8, MH12 and Hu317) were fully compatible with DSC analysis and gave good resolution data (FIG. 10), presenting comparable sample homogeneity and cooperativity. In FIG. 10A (09C06 IgG), the first transition represents CH2 domain unfolding, the second transition represents the unfolding of the Fab fragment and the third transition represents CH3 domain unfolding. For clones MH4, MH8 and MH12, the major Fab transition is lower, overlapping with the CH2 domain (FIG. 10B-D). For clone Hu317, the Fab domain transition is actually higher and overlapping with the CH3 (FIG. 10E). Overall, the Fab unfolding Tm values demonstrated that the v-domains of lead clones 09C06, MH4, MH8 and MH12, while still relatively stable, were actually reduced in overall stability in comparison to those of Hu317 (Table 7).

Forced Oxidation Analyses

Oxidation of exposed amino acid residues, such as tryptophan and methionine is a common degradation pathway for mAbs, altering their structural integrity with potential impact on their biological activity and heterogeneity. In this study, forced oxidation using 0.5% H2O2 for 2 hours at room temperature was applied to IgGs 09C06, MH4, MH8, MH12 and Hu317. As oxidation can alter overall hydrophobicity of an antibody, either by increasing the polarity of the oxidised form or through conformational changes, potential changes induced by forced oxidation were analysed by Size Exclusion (SEC), Reverse Phase (RP) and Hydrophobic Interaction (HIC) Chromatographies.

SEC analysis—No significant changes in SEC profile, induced by forced oxidation, were observed for any of the five IgGs, with higher molecular weight isoforms remaining below 0.6% of total protein (Table 8).

RP analysis—No significant changes in the retention time of intact mAbs (non-reduced and reduced) were observed upon H2O2 treatment, implying minimal oxidation of exposed amino acids (Table 8).

HIC analysis—H2O2 treatment induced only a minor (0.4-0.6) minutes decrease in the retention on HIC for all 5 test articles, implying limited oxidation of exposed amino acids (Table 8).

Together, these data confirmed that the lead IgGs 09C06, MH4, MH8 and MH12 did not exhibit improved stability or reduced oxidative degradation potential in comparison to Hu317 and that neither stability changes nor changes in post-translational CDR modification motifs were responsible for the observed improvements in charge homogeneity.

Antibody Binding Specificity Analyses

Figure 11:
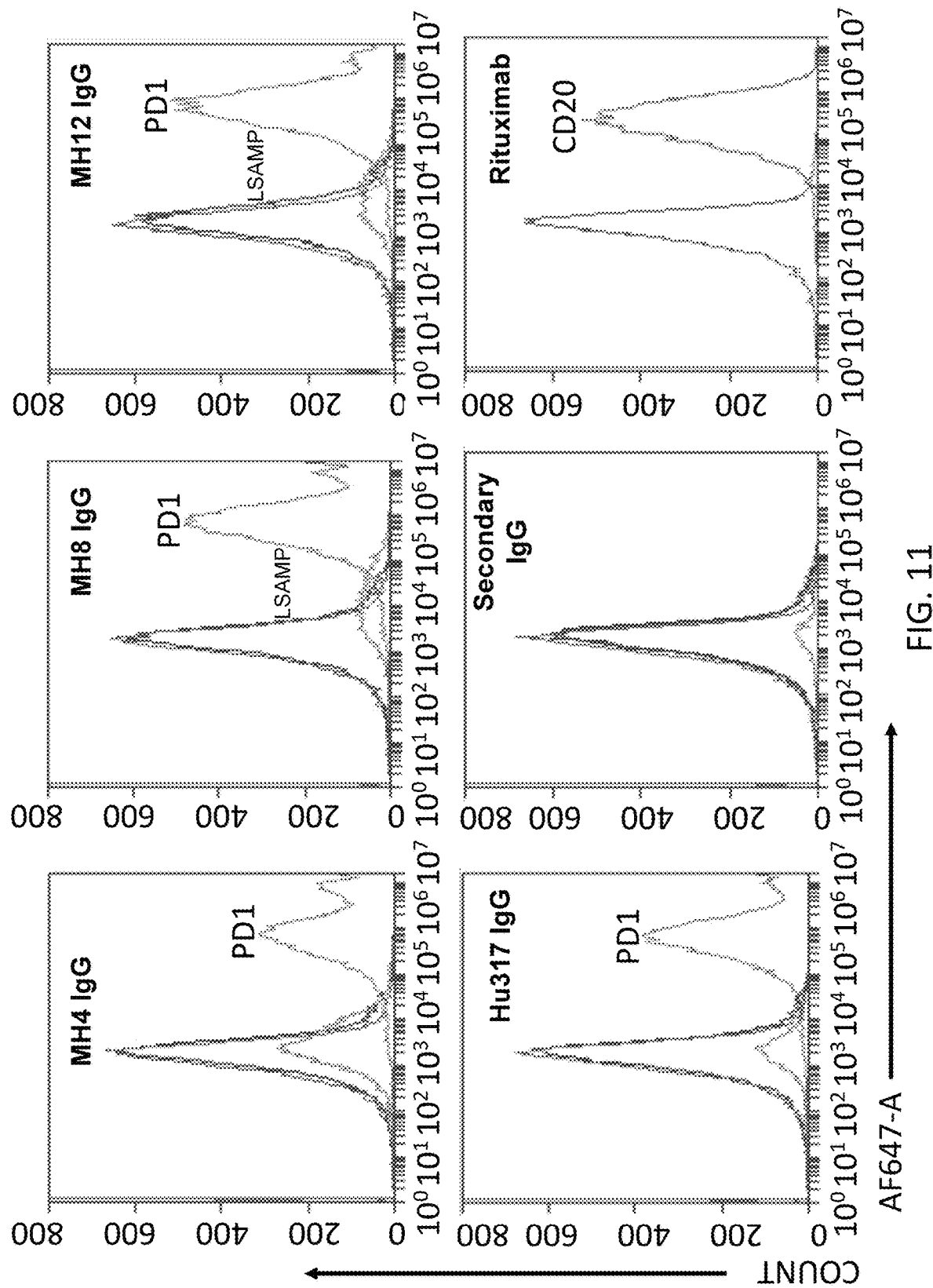
FIG. 11. Flow cytometric binding of Hu317, lead and control IgGs to HEK293 cells transfected with PD1 or potential off-target binding proteins. Analyses of binding specificity were performed on HEK293 cells transiently transfected with plasmids encoding either human PD1, human BTN2A1, human LSAMP, human CD20 or ZS green marker only. Each antibody was used in staining at 2 µg/ml concentration and histograms are indicated per antibody in this figure. In each panel of this figure, where target binding events were observed (indicated by a movement of all, or the major portion of the requisite histogram towards higher AF647 signal), the peak of interest is named (PD1, CD20, LSAMP). No binding signals were observed for any IgG against BTN2A1.

To examine the proteomic selectivity of Hu317 and clones MH4, MH8 and MH12, in vitro technologies (Retrogenix, Ltd.), which are based on using high-density arrays of cells expressing 5528 unique human membrane receptors and tethered secreted proteins, were used to screen for off-target binding specificities in purified IgG form. This receptor array binding screen identified that Hu317 exhibited strong binding to membrane-expressed PD1 exclusively, with no measurable binding to any other proteins (Table 12). In contrast, clones MH4, MH8 and MH12 also exhibited very limited signals, with strongest signal for PD1, but also had 2 potential new binding specificities: BNT2A1 (accession number NM_007049) and LSAMP (BC033803). MH12 was the only clone to show any binding signal to BNT2A1. To examine these findings with an orthogonal, high-sensitivity assay, the plasmids encoding for CD20, PD1, BTN2A1, LSAMP, and ZS green only (negative control) were used to perform transient transfection of the human cell line HEK293. Transfected cells were then stained using Hu317, MH4, MH8, MH12 and Rituximab IgGs. In staining of PD1-transfected cells at 2 µg/ml, all tested antibodies other than the Rituximab and secondary only controls showed the expected strong, specific staining of PD1-transfected cells but not ZS green-transfected (FIG. 11). Hu317 IgG showed no binding to any cells other than PD1-transfected cells, confirming the findings of the chip analyses, where this IgG was fully PD1 selective. Rituximab positive control exhibited strong, specific staining of CD20-transfected cells and the negative control (secondary labelled antibody only) exhibited no binding to any cells (FIG. 11). In contrast, only clones MH8 and MH12 exhibited clear binding signal on both PD1 and LSAMP, but no binding of BTN2A1, both in histogram analysis (FIG. 11) and in median fold-change of mean fluorescence measurements over ZSgreen-only transfected cells (Table 13). This unexpected, newly-acquired, reactivity to a single new protein in the human receptor proteome for clones MH8 and MH12 may be of potential therapeutic benefit, as LSAMP is a cell surface receptor whose expression has been shown to be upregulated in specific tumour types such as Acute Myeloid Leukaemia (Coccaro, N. et al. Cancer Genetics 2015, 208(10):517-522) and may therefore be of value in co-targeting along with PD1.

Although the present invention has been described with reference to preferred or exemplary embodiments, those skilled in the art will recognize that various modifications and variations to the same can be accomplished without departing from the spirit and scope of the present invention and that such modifications are clearly contemplated herein. No limitation with respect to the specific embodiments disclosed herein and set forth in the appended claims is intended nor should any be inferred.

All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls. However, mention of any reference, article, publication, patent, patent publication, and patent application cited herein is not, and should not be taken as an acknowledgment, or any form of suggestion, that they constitute valid prior art or form part of the common general knowledge in any country in the world.

TABLE 1

Amino acid sequences murine anti-PD1 CDRs as defined here ("Unified" scheme) in comparison to alternative definitions.

| Scheme | HCDR1 | HCDR2 | HCDR3 | LCDR1 | LCDR2 | LCDR3 |
|---|---|---|---|---|---|---|
| Unified | GFSLTSYGVH (SEQ ID NO:89) | LGVIWAGGSTNYNSALMS (SEQ ID NO:94) | AYGNYWYIDV (SEQ ID NO:101) | KASQSVSNDVA (SEQ ID NO:105) | YAFHRFT (SEQ ID NO:109) | HQAYSSPYT (SEQ ID NO:111) |
| Kabat | SYGVH (SEQ ID NO:90) | VIWAGGSTNYNSALMS (SEQ ID NO:95) | AYGNYWYIDV (SEQ ID NO:101) | KASQSVSNDVA (SEQ ID NO:105) | YAFHRFT (SEQ ID NO:109) | HQAYSSPYT (SEQ ID NO:111) |
| Chotia | GFSLTSY (SEQ ID NO:91) | WAGGST (SEQ ID NO:96) | AYGNYWYIDV (SEQ ID NO:101) | KASQSVSNDVA (SEQ ID NO:105) | YAFHRFT (SEQ ID NO:109) | HQAYSSPYT (SEQ ID NO:111) |
| IMGT | GFSLTSYG (SEQ ID NO:92) | IWAGGSTN (SEQ ID NO:97) | ARAYGNYWYIDV (SEQ ID NO:102) | QSVSND (SEQ ID NO:106) | YAF | HQAYSSPYT (SEQ ID NO:111) |
| AHo | GFSLTSYGVH (SEQ ID NO:89) | IWAGGSTNYNSALMS (SEQ ID NO:98) | AYGNYWYID (SEQ ID NO:103) | ASQSVSND (SEQ ID NO:107) | YAFHRFT (SEQ ID NO:109) | AYSSPY (SEQ ID NO:112) |
| AbM | GFSLTSYGVH (SEQ ID NO:89) | VIWAGGSTNY (SEQ ID NO:99) | AYGNYWYIDV (SEQ ID NO:101) | KASQSVSNDVA (SEQ ID NO:105) | YAFHRFT (SEQ ID NO:109) | HQAYSSPYT (SEQ ID NO:111) |
| Contact | TSYGVH (SEQ ID NO:93) | LGVIWAGGSTNY (SEQ ID NO:100) | ARAYGNYWYID (SEQ ID NO:104) | SNDVAWY (SEQ ID NO:108) | LLIYYAFHRF (SEQ ID NO:110) | HQAYSSPY (SEQ ID NO:113) |

TABLE 2

Amino acid sequence of MU317 murine anti-PD1 v-domains (mVH/mVL) and human germline CDR grafts (VH1/VL1).

| V DOMAIN | Human germline[1] | Amino acid sequence[2] |
|---|---|---|
| Mu317 VH | n/a | QVQLKESGPGLVAPSKNLSITCTVSGF SLTSYGVHWIRQPPGKGLEWLGVIWAG GSTNYNSALMSRLSISKDNSRSQVFLR MNSLQTDDTAMYYCARAYGNYWYIDVW GAGTTVTVSS (SEQ ID NO: 114) |

TABLE 2-continued

Amino acid sequence of MU317 murine anti-PD1 v-domains (mVH/mVL) and human germline CDR grafts (VH1/VL1).

| V DOMAIN | Human germline[1] | Amino acid sequence[2] |
|---|---|---|
| Hu317 VH | IGHV4-4 | QVQLQESGPGLVKPSETLSLTCTVSGF SLTSYGVHWIRQPPGKGLEWIGVIYAD GSTNYNPSLKSRVTISKDTSKNQVSLK LSSVTAADTAVYYCARAYGNYWYIDVW GQGTTVTVSS (SEQ ID NO: 115) |
| VH GRAFT | IGHV3-7[3] | EVQLVESGGGLVQPGGSLRLSCAASGF SLTSYGVHWVRQAPGKGLEWLGVIWAG GSTNYNDSVKGRFTISRDNAKNSLYLQ MNSLRAEDTAVYYCARAYGNYWYIDVW GQGTTVTVSS (SEQ ID NO: 116) |
| Mu317 VL | n/a | DIVMTQTPKFLLVSAGDRVTITCKASQ SVSNDVAWYQQKPGQSPKLLINYAFHR FTGVPDRFTGSGYGTDFIFTISTVQAE DLAVYFCHQAYSSPYTFGGGTKLEMK (SEQ ID NO: 117) |
| Hu317 VL | IGKV4-1 | DIVMTQSPDSLAVSLGERATINCKSSE SVSNDVAWYQQKPGQPPKLLINYAFHR FTGVPDRFSGSGYGTDFTLTISSLQAE DVAVYYCHQAYSSPYTFGQGTKLEIK (SEQ ID NO: 118) |
| VL GRAFT | IGKV4-1[3] | DIVMTQSPDSLAVSLGERATINCKSSQ SVSNDVAWYQQKPGQPPKLLINYAFHR FTGVPDRFSGSGYGTDFTLTISSLQAE DVAVYYCHQAYSSPYTFGQGTKLEIK (SEQ ID NO: 119) |

[1]Human germline definitions used for grafting, based on IMGT system.
[2]CDR residues are in bold and underlined. As noted above, the "Unified" CDR definitions used in this manuscript are an expanded definition in comparison to the classical Kabat definition. Each sequence above shows the framework regions (FRs) and the CDRs in the following order: FR1-CDR1-FR2-CDR2-FR3-CDR3-FR4.
[3]Grafts used for library construction.

TABLE 3

Unique CDRs from Fab clones shown to bind human and cyno PD1 proteins.

| HCDR1 | HCDR2 | HCDR2 contd | HCDR2 contd | HCDR3 | LCDR1 | LCDR2 | LCDR3 |
|---|---|---|---|---|---|---|---|
| GFNFSSYGMH (SEQ ID NO: 120) | LANIKADGSEKYVDSVKG (SEQ ID NO: 147) | LGNIKQGGSENYNDSVKG (SEQ ID NO: 210) | VANIWQDGSTNYNDSVKG (SEQ ID NO: 233) | AFGNYWYIDV (SEQ ID NO: 337) | KSSESVGNDLA (SEQ ID NO: 397) | YAFHRES (SEQ ID NO: 400) | HQAYSNPYT (SEQ ID NO: 407) |
| GFSFSSYGMH (SEQ ID NO: 42) | LANIKADGSENYVDSVKG (SEQ ID NO: 148) | LGNIKQGGSTKYVDSVKG (SEQ ID NO: 211) | VANIWQGGSEKYNDSVKG (SEQ ID NO: 275) | AWGNYWYIDV (SEQ ID NO: 338) | KSSESVGNDVA (SEQ ID NO: 398) | YAFHRET (SEQ ID NO: 401) | HQAYSTPYT (SEQ ID NO: 46) |
| GFSFSSYGMS (SEQ ID NO: 121) | LANIKADGSTKYVDSVKG (SEQ ID NO: 149) | LGNIKQGGSTNYVDSVKG (SEQ ID NO: 212) | VANIWQGGSTKYNDSVKG (SEQ ID NO: 276) | AYGAYWYIDV (SEQ ID NO: 339) | KSSESVSNDLA (SEQ ID NO: 399) | YAFHRFA (SEQ ID NO: 402) | QQAYSSPYT (SEQ ID NO: 75) |
| GFSFSSYGVH (SEQ ID NO: 122) | LANIKADGSTNYVDSVKG (SEQ ID NO: 150) | LGNIWADGSEKYNDSVKG (SEQ ID NO: 213) | VAVIKADGSTNYNDSVKG (SEQ ID NO: 277) | AYGEYWYIDV (SEQ ID NO: 340) | KSSQSVGNDLA (SEQ ID NO: 77) | YAFHRFS (SEQ ID NO: 403) | QQAYSTPYT (SEQ ID NO: 52) |
| GFSFSSYGVS (SEQ ID NO: 123) | LANIKAGGSEKYNDSVKG (SEQ ID NO: 151) | LGNIWADGSEKYVDSVKG (SEQ ID NO: 214) | VAVIKQDGSENYVDSVKG (SEQ ID NO: 278) | AYGFYWYIDV (SEQ ID NO: 341) | KSSQSVGNDVA (SEQ ID NO: 74) | YAFPRFT (SEQ ID NO: 404) | QQSYSTPYT (SEQ ID NO: 408) |
| GFSFSSYWMH (SEQ ID NO: 124) | LANIKAGGSEKYNDSVKG (SEQ ID NO: 152) | LGNIWADGSENYNDSVKG (SEQ ID NO: 215) | VAVIKQDGSTKYNDSVKG (SEQ ID NO: 279) | AYGGYWYIDV (SEQ ID NO: 342) | KSSQSVSNDLA (SEQ ID NO: 51) | YAFTRFS (SEQ ID NO: 405) | |
| GFSFTSYGMH (SEQ ID NO: 59) | LANIKAGGSENYNDSVKG (SEQ ID NO: 153) | LGNIWADGSENYVDSVKG (SEQ ID NO: 216) | VAVIKQDGSTNYNDSVKG (SEQ ID NO: 280) | AYGHYWYIDV (SEQ ID NO: 343) | KSSQSVSNDVA (SEQ ID NO: 44) | YAFTRFT (SEQ ID NO: 406) | |
| GFSFTSYGMS (SEQ ID NO: 47) | LANIKQDGSEKYVDSVKG (SEQ ID NO: 154) | LGNIWADGSTKYVDSVKG (SEQ ID NO: 217) | VAVIKQDGSTNYVDSVKG (SEQ ID NO: 281) | AYGIYWYIDN (SEQ ID NO: 344) | KSSQSVTNDVA (SEQ ID NO: 36) | YASHRFS (SEQ ID NO: 79) | |
| GFSFTSYGVH (SEQ ID NO: 125) | LANIKQDGSENYVDSVKG (SEQ ID NO: 155) | LGNIWADGSTKYVDSVKG (SEQ ID NO: 218) | VAVIWADGSEKYVDSVKG (SEQ ID NO: 282) | AYGNVWYIDV (SEQ ID NO: 396) | | YASHRFT (SEQ ID NO: 45) | |
| GFSFTSYGVS (SEQ ID NO: 126) | LANIKQDGSTKYVDSVKG (SEQ ID NO: 156) | LGNIWADGSTNYVDSVKG (SEQ ID NO: 219) | VAVIWADGSENYNDSVKG (SEQ ID NO: 283) | AYGNWWYIDV (SEQ ID NO: 345) | | YAYHRFT (SEQ ID NO: 37) | |
| GFSFTSYWMH (SEQ ID NO: 127) | LANIKQDGSTKYVDSVKG (SEQ ID NO: 157) | LGNIWADGSTNYVDSVKG (SEQ ID NO: 220) | VAVIWADGSTKYNDSVKG (SEQ ID NO: 284) | AYGNYFYIDV (SEQ ID NO: 346) | | YAYHRFS (SEQ ID NO: 78) | |

TABLE 3-continued

Unique CDRs from Fab clones shown to bind human and cyno PDI proteins.

| HCDR1 | HCDR2 | HCDR2 contd | HCDR2 contd | HCDR3 | LCDR1 | LCDR2 | LCDR3 |
|---|---|---|---|---|---|---|---|
| GFSLSSYG IS (SEQ ID NO: 128) | LANIWADGSEK YNDSVKG (SEQ ID NO: 158) | LGNIWAGGSEN YVDSVKG (SEQ ID NO: 221) | VAVIWADGSTK YVDSVKG (SEQ ID NO: 285) | AYGNYFYIDW (SEQ ID NO: 347) | | | |
| GFSLSSYG MH (SEQ ID NO: 129) | LANIWADGSEK YVDSVKG (SEQ ID NO: 159) | LGNIWQDGSEK YNDSVKG (SEQ ID NO: 222) | VAVIWADGSTN YNDSVKG (SEQ ID NO: 286) | AYGNYHYIDV (SEQ ID NO: 348) | | | |
| GFSLSSYG MS (SEQ ID NO: 39) | LANIWADGSEN YNDSVKG (SEQ ID NO: 160) | LGNIWQDGSEN YVDSVKG (SEQ ID NO: 223) | VAVIWQDGSEK YNDSVKG (SEQ ID NO: 287) | AYGNYMYIDV (SEQ ID NO: 56) | | | |
| GFSLSSYG VH (SEQ ID NO: 130) | LANIWADGSEN YVDSVKG (SEQ ID NO: 161) | LGNIWQDGSEN YNDSVKG (SEQ ID NO: 224) | VAVIWQDGSEN YNDSVKG (SEQ ID NO: 288) | AYGNYPYIDV (SEQ ID NO: 349) | | | |
| GFSLSSYG VS (SEQ ID NO: 131) | LANIWADGSTK YNDSVKG (SEQ ID NO: 162) | LGNIWQDGSEN YVDSVKG (SEQ ID NO: 225) | VAVIWQDGSEN YVDSVKG (SEQ ID NO: 289) | AYGNYQYIDV (SEQ ID NO: 350) | | | |
| GFSLSSYW MH (SEQ ID NO: 132) | LANIWADGSTK YVDSVKG (SEQ ID NO: 163) | LGNIWQDGSTK YNDSVKG (SEQ ID NO: 226) | VAVIWQDGSTK YNDSVKG (SEQ ID NO: 290) | AYGNYSYIDV (SEQ ID NO: 351) | | | |
| GFSLTSYW MH (SEQ ID NO: 133) | LANIWADGSTN YNDSVKG (SEQ ID NO: 164) | LGNIWQDGSTK YVDSVKG (SEQ ID NO: 227) | VAVIWQDGSTN YNDSVKG (SEQ ID NO: 291) | AYGNYVYIDV (SEQ ID NO: 352) | | | |
| GFTFSSYG MH (SEQ ID NO: 57) | LANIWADGSTN YVDSVKG (SEQ ID NO: 165) | LGNIWQDGSTN YNDSVKG (SEQ ID NO: 228) | VAVIWQDGSTN YNDSVKG (SEQ ID NO: 292) | AYGNYWYADV (SEQ ID NO: 353) | | | |
| GFTFSSYG MS (SEQ ID NO: 33) | LANIWAGGSTN YNDSVKG (SEQ ID NO: 166) | LGNIWQDGSTN YVDSVKG (SEQ ID NO: 229) | VAVIWQDGSTN YVDSVKG (SEQ ID NO: 40) | AYGNYWYGDV (SEQ ID NO: 354) | | | |
| GFTFSSYG VH (SEQ ID NO: 49) | LANIWQDGSEK YNDSVKG (SEQ ID NO: 167) | LGNIWQGGSTN YNDSVKG (SEQ ID NO: 230) | VAVIWQGGSTK YNDSVKG (SEQ ID NO: 293) | AYGNYWYIDA (SEQ ID NO: 355) | | | |
| GFTFSSYG VS (SEQ ID NO: 134) | LANIWQDGSEK YVDSVKG (SEQ ID NO: 168) | LGVIKADGSEN YNDSVKG (SEQ ID NO: 231) | VGNIKADGSEN YNDSVKG (SEQ ID NO: 294) | AYGNYWYIDE (SEQ ID NO: 356) | | | |
| GFTFTSYG MH (SEQ ID NO: 135) | LANIWQDGSEN YNDSVKG (SEQ ID NO: 169) | LGVIKADGSTK YNDSVKG (SEQ ID NO: 232) | VGNIKADGSTK YNDSVKG (SEQ ID NO: 295) | AYGNYWYIDF (SEQ ID NO: 357) | | | |
| GFTFTSYG MS (SEQ ID NO: 136) | LANIWQDGSEN YVDSVKG (SEQ ID NO: 53) | LGVIKADGSTN YNDSVKG (SEQ ID NO: 234) | VGNIKADGSTN YNDSVKG (SEQ ID NO: 296) | AYGNYWYIDG (SEQ ID NO: 358) | | | |
| GFTFTSYG VH (SEQ ID NO: 137) | LANIWQDGSTK YVDSVKG (SEQ ID NO: 170) | LGVIKQDGSEN YVDSVKG (SEQ ID NO: 235) | VGNIKAGGSTN YVDSVKG (SEQ ID NO: 297) | AYGNYWYIDH (SEQ ID NO: 359) | | | |
| GFTFTSYG VS (SEQ ID NO: 138) | LANIWQDGSTK YVDSVKG (SEQ ID NO: 171) | LGVIKQDGSTK YVDSVKG (SEQ ID NO: 236) | VGNIKQDGSEN YNDSVKG (SEQ ID NO: 298) | AYGNYWYIDI (SEQ ID NO: 360) | | | |
| GFTLSSYG MH (SEQ ID NO: 54) | LANIWQDGSTN YNDSVKG (SEQ ID NO: 172) | LGVIKQDGSTK YVDSVKG (SEQ ID NO: 237) | VGNIKQDGSEN YVDSVKG (SEQ ID NO: 299) | AYGNYWYIDK (SEQ ID NO: 361) | | | |
| GFTLSSYG MS (SEQ ID NO: 139) | LANIWQDGSTN YVDSVKG (SEQ ID NO: 48) | LGVIKQDGSTN YNDSVKG (SEQ ID NO: 238) | VGNIKQDGSTK YNDSVKG (SEQ ID NO: 300) | AYGNYWYIDL (SEQ ID NO: 362) | | | |
| GFTLSSYG VH (SEQ ID NO: 140) | LANIWQGGSEN YVDSVKG (SEQ ID NO: 173) | LGVIKQGGSEN YNDSVKG (SEQ ID NO: 239) | VGNIKQDGSTN YNDSVKG (SEQ ID NO: 301) | AYGNYWYIDM (SEQ ID NO: 363) | | | |
| GFTLSSYG VS (SEQ ID NO: 141) | LAVIKADGSEK YNDSVKG (SEQ ID NO: 174) | LGVIWADGSEK YNDSVKG (SEQ ID NO: 240) | VGNIKQDGSTN YVDSVKG (SEQ ID NO: 302) | AYGNYWYIDR (SEQ ID NO: 35) | | | |

TABLE 3-continued

Unique CDRs from Fab clones shown to bind human and cyno PDI proteins.

| HCDR1 | HCDR2 | HCDR2 contd | HCDR2 contd | HCDR3 | LCDR1 | LCDR2 | LCDR3 |
|---|---|---|---|---|---|---|---|
| GFTLSSYW MH (SEQ ID NO: 142) | LAVIKADGSEN YNDSVKG (SEQ ID NO: 175) | LGVIWADGSEN YNDSVKG (SEQ ID NO: 241) | VGNIKQGGSTK YNDSVKG (SEQ ID NO: 303) | AYGNYWYIDS (SEQ ID NO: 364) | | | |
| GFTLTSYG MH (SEQ ID NO: 143) | LAVIKADGSTK YVDSVKG (SEQ ID NO: 176) | LGVIWADGSTK YNDSVKG (SEQ ID NO: 242) | VGNIWADGSEN YNDSVKG (SEQ ID NO: 304) | AYGNYWYIDT (SEQ ID NO: 365) | | | |
| GFTLTSYG MS (SEQ ID NO: 144) | LAVIKADGSTN YNDSVKG (SEQ ID NO: 177) | LGVIWADGSTN YVDSVKG (SEQ ID NO: 243) | VGNIWADGSTK YVDSVKG (SEQ ID NO: 305) | AYGNYWYIDW (SEQ ID NO: 366) | | | |
| GFTLTSYG VH (SEQ ID NO: 145) | LAVIKAGGSTN YVDSVKG (SEQ ID NO: 178) | LGVIWADGSTN YNDSVKG (SEQ ID NO: 244) | VGNIWADGSTN YVDSVKG (SEQ ID NO: 306) | AYGNYWYIDY (SEQ ID NO: 367) | | | |
| GFTLTSYG VS (SEQ ID NO: 146) | LAVIKQDGSEK YNDSVKG (SEQ ID NO: 179) | LGVIWADGSTN YVDSVKG (SEQ ID NO: 245) | VGNIWADGSTN YVDSVKG (SEQ ID NO: 307) | AYGNYWYIEV (SEQ ID NO: 368) | | | |
| | LAVIKQDGSTN YNDSVKG (SEQ ID NO: 180) | LGVIWADGSTS YNDSVKG (SEQ ID NO: 246) | VGNIWQDGSEK YNDSVKG (SEQ ID NO: 308) | AYGNYWYLDV (SEQ ID NO: 369) | | | |
| | LAVIKQDGSTN YVDSVKG (SEQ ID NO: 181) | LGVIWAGGSTN YNDSVKG (SEQ ID NO: 247) | VGNIWQDGSEK YVDSVKG (SEQ ID NO: 309) | AYGNYWYMDV (SEQ ID NO: 370) | | | |
| | LAVIWADGSEK YNDSVKG (SEQ ID NO: 182) | LGVIWPDGSTN YNDSVKG (SEQ ID NO: 248) | VGNIWQDGSEN YVDSVKG (SEQ ID NO: 310) | AYGNYWYSDV (SEQ ID NO: 371) | | | |
| | LAVIWADGSEN YNDSVKG (SEQ ID NO: 183) | LGVIWQDGSEK YNDSVKG (SEQ ID NO: 249) | VGNIWQDGSTK YNDSVKG (SEQ ID NO: 311) | AYGNYWYTDV (SEQ ID NO: 372) | | | |
| | LAVIWADGSEN YVDSVKG (SEQ ID NO: 184) | LGVIWQDGSEK YVDSVKG (SEQ ID NO: 250) | VGNIWQDGSTK YVDSVKG (SEQ ID NO: 312) | AYGNYWYVDV (SEQ ID NO: 373) | | | |
| | LAVIWADGSTK YVDSVKG (SEQ ID NO: 185) | LGVIWQDGSEN YNDSVKG (SEQ ID NO: 251) | VGNIWQDGSTN YNDSVKG (SEQ ID NO: 313) | AYGNYWYYDV (SEQ ID NO: 374) | | | |
| | LAVIWADGSTK YVDSVKG (SEQ ID NO: 186) | LGVIWQDGSEN YVDSVKG (SEQ ID NO: 252) | VGNIWQDGSTN YVDSVKG (SEQ ID NO: 314) | AYGQYWYIDV (SEQ ID NO: 375) | | | |
| | LAVIWADGSTN YNDSVKG (SEQ ID NO: 187) | LGVIWQDGSTK YVDSVKG (SEQ ID NO: 253) | VGNIWQGGSEK YNDSVKG (SEQ ID NO: 315) | AYGRYWYIDV (SEQ ID NO: 376) | | | |
| | LAVIWADGSTN YVDSVKG (SEQ ID NO: 55) | LGVIWQDGSTK YVDSVKG (SEQ ID NO: 254) | VGVIKADGSTK YNDSVKG (SEQ ID NO: 316) | AYGSYWYIDV (SEQ ID NO: 377) | | | |
| | LAVIWAGGSEK YNDSVKG (SEQ ID NO: 188) | LGVIWQDGSTN YNDSVKG (SEQ ID NO: 255) | VGVIKADGSTN YNDSVKG (SEQ ID NO: 317) | AYGTYWYIDV (SEQ ID NO: 378) | | | |
| | LAVIWAGGSEN KYNDSVG (SEQ ID NO: 189) | LGVIWQDGSTN YVDSVKG (SEQ ID NO: 256) | VGVIKADGSTN YVDSVKG (SEQ ID NO: 318) | AYGVYWYIDR (SEQ ID NO: 379) | | | |
| | LAVIWAGGSTK YNDSVKG (SEQ ID NO: 190) | LGVIWQGGSTK YNDSVKG (SEQ ID NO: 257) | VGVIKQDGSEN YNDSVKG (SEQ ID NO: 319) | AYGVYWYIDV (SEQ ID NO: 380) | | | |
| | LAVIWQDGSEK YNDSVKG (SEQ ID NO: 191) | LGVIWQGGSTN YNDSVKG (SEQ ID NO: 258) | VGVIKQDGSTK YNDSVKG (SEQ ID NO: 320) | AYGWYWYIDV (SEQ ID NO: 381) | | | |
| | LAVIWQDGSEK YVDSVKG (SEQ ID NO: 192) | VANIKADGSEK YVDSVKG (SEQ ID NO: 259) | VGVIKQDGSTN YNDSVKG (SEQ ID NO: 321) | AYGYYWYIDV (SEQ ID NO: 382) | | | |

TABLE 3-continued

Unique CDRs from Fab clones shown to bind human and cyno PDI proteins.

| HCDR1 | HCDR2 | HCDR2 contd | HCDR2 contd | HCDR3 | LCDR1 | LCDR2 | LCDR3 |
|---|---|---|---|---|---|---|---|
| | LAVIWQDGSEN YNDSVKG (SEQ ID NO: 193) | VANIKADGSEN YVDSVKG (SEQ ID NO: 260) | VGVIWADGSEK YNDSVKG (SEQ ID NO: 322) | DYGNYWYIDV (SEQ ID NO: 383) | | | |
| | LAVIWQDGSEN YVDSVKG (SEQ ID NO: 194) | VANIKADGSTK YVDSVKG (SEQ ID NO: 261) | VGVIWADGSEN YNDSVKG (SEQ ID NO: 323) | EYGNYWYIDR (SEQ ID NO: 384) | | | |
| | LAVIWQDGSTK YNDSVKG (SEQ ID NO: 195) | VANIKQDGSEK YNDSVKG (SEQ ID NO: 262) | VGVIWADGSEN YVDSVKG (SEQ ID NO: 324) | EYGNYWYIDV (SEQ ID NO: 385) | | | |
| | LAVIWQDGSTK YVDSVKG (SEQ ID NO: 196) | VANIKQDGSEK YVDSVKG (SEQ ID NO: 263) | VGVIWADGSTK YNDSVKG (SEQ ID NO: 325) | GYGNYWYIDV (SEQ ID NO: 61) | | | |
| | LAVIWQDGSTN YNDSVKG (SEQ ID NO: 197) | VANIKQDGSTK YNDSVKG (SEQ ID NO: 264) | VGVIWADGSTK YVDSVKG (SEQ ID NO: 326) | HYGNYWYIDV (SEQ ID NO: 386) | | | |
| | LAVIWQDGSTN YVDSVKG (SEQ ID NO: 198) | VANIKQDGSTN YNDSVKG (SEQ ID NO: 265) | VGVIWADGSTN YNDSVKG (SEQ ID NO: 327) | IYGNYWYIDR (SEQ ID NO: 387) | | | |
| | LAVIWQGGSEK YNDSVKG (SEQ ID NO: 199) | VANIWADGSEK YNDSVKG (SEQ ID NO: 266) | VGVIWADGSTN YVDSVKG (SEQ ID NO: 328) | IYGNYWYIDV (SEQ ID NO: 388) | | | |
| | LAVIWQGGSEN YNDSVKG (SEQ ID NO: 200) | VANIWADGSTK YNDSVKG (SEQ ID NO: 267) | VGVIWQDGSEK YNDSVKG (SEQ ID NO: 329) | LYGNYWYIDV (SEQ ID NO: 389) | | | |
| | LGNIKADGSEN YNDSVKG (SEQ ID NO: 201) | VANIWADGSTN YNDSVKG (SEQ ID NO: 268) | VGVIWQDGSEK YVDSVKG (SEQ ID NO: 330) | MYGNYWYIDV (SEQ ID NO: 390) | | | |
| | LGNIKADGSTK YNDSVKG (SEQ ID NO: 202) | VANIWADGSTN YVDSVKG (SEQ ID NO: 269) | VGVIWQDGSEN YNDSVKG (SEQ ID NO: 331) | QYGNYWYIDR (SEQ ID NO: 391) | | | |
| | LGNIKADGSTK YVDSVKG (SEQ ID NO: 203) | VANIWAGGSEN YNDSVKG (SEQ ID NO: 270) | VGVIWQDGSEN YVDSVKG (SEQ ID NO: 50) | QYGNYWYIDV (SEQ ID NO: 392) | | | |
| | LGNIKADGSTN YNDSVKG (SEQ ID NO: 204) | VANIWQDGSEK YNDSVKG (SEQ ID NO: 271) | VGVIWQDGSTK YNDSVKG (SEQ ID NO: 332) | SYGNYWYIDV (SEQ ID NO: 393) | | | |
| | LGNIKAGGSTN YNDSVKG (SEQ ID NO: 205) | VANIWQDGSEK YVDSVKG (SEQ ID NO: 41) | VGVIWQDGSTK YVDSVKG (SEQ ID NO: 333) | VYGNYWYIDV (SEQ ID NO: 394) | | | |
| | LGNIKAGGSTN YVDSVKG (SEQ ID NO: 206) | VANIWQDGSEN YVDSVKG (SEQ ID NO: 272) | VGVIWQDGSTN YNDSVKG (SEQ ID NO: 334) | WYGNYWYIDV (SEQ ID NO: 395) | | | |
| | LGNIKQDGSEN YNDSVKG (SEQ ID NO: 207) | VANIWQDGSEN YVDSVKG (SEQ ID NO: 273) | VGVIWQDGSTN YVDSVKG (SEQ ID NO: 60) | | | | |
| | LGNIKQDGSTK YNDSVKG (SEQ ID NO: 208) | VANIWQDGSTK YNDSVKG (SEQ ID NO: 274) | VGVIWQGGSEK YVDSVKG (SEQ ID NO: 335) | | | | |
| | LGNIKQDGSTN YNDSVKG (SEQ ID NO: 209) | | VGVIWQGGSTN YNDSVKG (SEQ ID NO: 336) | | | | |

TABLE 4

CDR sequences of unique, library-derived and designer, PD1 antagonistic IgGs.

| Clone name | LCDR1 | LCDR2 | LCDR3 | HCDR1 | HCDR2 | HCDR3 |
|---|---|---|---|---|---|---|
| 20C07 | KSSQSVSNDVA (SEQ ID NO: 44) | YASHRFT (SEQ ID NO: 45) | HQAYSTPYT (SEQ ID NO: 46) | GFSFTSYGMS (SEQ ID NO: 47) | LANIWQDGSTNYVDSVKG (SEQ ID NO: 48) | AYGNYWYIDR (SEQ ID NO: 35) |
| 11C08 | KSSQSVSNDLA (SEQ ID NO: 51) | YASHRFT (SEQ ID NO: 45) | QQAYSTPYT (SEQ ID NO: 52) | GFTFSSYGVH (SEQ ID NO: 49) | VGVIWQDGSENYVDSVKG (SEQ ID NO: 50) | AYGNYWYIDR (SEQ ID NO: 35) |
| 09C06 | KSSQSVSNDVA (SEQ ID NO: 44) | YASHRFT (SEQ ID NO: 45) | HQAYSTPYT (SEQ ID NO: 46) | GFSFSSYGMH (SEQ ID NO: 42) | VANIWQDGSTNYVDSVKG (SEQ ID NO: 43) | AYGNYWYIDR (SEQ ID NO: 35) |
| 17A12 | KSSQSVSNDVA (SEQ ID NO: 44) | YASHRFT (SEQ ID NO: 45) | QQAYSTPYT (SEQ ID NO: 52) | GFSFSSYGMH (SEQ ID NO: 42) | LANIWQDGSENYVDSVKG (SEQ ID NO: 53) | AYGNYWYIDR (SEQ ID NO: 35) |
| 17D08 | KSSQSVSNDVA (SEQ ID NO: 44) | YASHRFT (SEQ ID NO: 45) | HQAYSTPYT (SEQ ID NO: 46) | GFTLSSYGMH (SEQ ID NO: 54) | LAVIWADGSTNYVDSVKG (SEQ ID NO: 55) | AYGNYMYIDV (SEQ ID NO: 56) |
| 17G08 | KSSQSVSNDVA (SEQ ID NO: 44) | YASHRFT (SEQ ID NO: 45) | HQAYSTPYT (SEQ ID NO: 46) | GFTFSSYGMH (SEQ ID NO: 57) | VGVIKQDGSENYVDSVKG (SEQ ID NO: 58) | AYGNYWYIDR (SEQ ID NO: 35) |
| 15D07 | KSSQSVSNDLA (SEQ ID NO: 51) | YASHRFT (SEQ ID NO: 45) | QQAYSTPYT (SEQ ID NO: 52) | GFSFTSYGMH (SEQ ID NO: 59) | VGVIWQDGSTNYVDSVKG (SEQ ID NO: 60) | GYGNYWYIDV (SEQ ID NO: 61) |
| MH1 | KSSQSVGNDVA (SEQ ID NO: 74) | YASHRFT (SEQ ID NO: 45) | QQAYSSPYT (SEQ ID NO: 75) | GFSLSSYGMS (SEQ ID NO: 39) | VAVIWQDGSTNYVDSVKG (SEQ ID NO: 40) | AYGNYWYIDR (SEQ ID NO: 35) |
| MH2 | KSSQSVTNDLA (SEQ ID NO: 76) | YASHRFT (SEQ ID NO: 45) | QQAYSTPYT (SEQ ID NO: 52) | GFSLSSYGMS (SEQ ID NO: 39) | VAVIWQDGSTNYVDSVKG (SEQ ID NO: 40) | AYGNYWYIDR (SEQ ID NO: 35) |
| MH3 | KSSQSVGNDLA (SEQ ID NO: 77) | YAYHRFS (SEQ ID NO: 78) | QQAYSTPYT (SEQ ID NO: 52) | GFSLSSYGMS (SEQ ID NO: 39) | VAVIWQDGSTNYVDSVKG (SEQ ID NO: 40) | AYGNYWYIDR (SEQ ID NO: 35) |
| MH4 | KSSQSVTNDVA (SEQ ID NO: 36) | YAYHRFT (SEQ ID NO: 37) | HQAYSTPYT (SEQ ID NO: 46) | GFSLSSYGMS (SEQ ID NO: 39) | VAVIWQDGSTNYVDSVKG (SEQ ID NO: 40) | AYGNYWYIDR (SEQ ID NO: 35) |
| MH5 | KSSQSVGNDVA (SEQ ID NO: 74) | YASHRFT (SEQ ID NO: 45) | QQAYSSPYT (SEQ ID NO: 75) | GFTFSSYGMS (SEQ ID NO: 33) | VANIWQDGSTKYVDSVKG (SEQ ID NO: 34) | AYGNYWYIDR (SEQ ID NO:35) |
| MH6 | KSSQSVTNDLA (SEQ ID NO: 76) | YASHRFT (SEQ ID NO: 45) | QQAYSTPYT (SEQ ID NO: 52) | GFTFSSYGMS (SEQ ID NO: 33) | VANIWQDGSTKYVDSVKG (SEQ ID NO: 34) | A YGNYWYIDR (SEQ ID NO: 35) |
| MH7 | KSSQSVGNDLA (SEQ ID NO: 77) | YAYHRFS (SEQ ID NO: 78) | QQAYSTPYT (SEQ ID NO: 52) | GFTFSSYGMS (SEQ ID NO: 33) | VANIWQDGSTKYVDSVKG (SEQ ID NO: 34) | AYGNYWYIDR (SEQ ID NO: 35) |
| MH8 | KSSQSVTNDVA (SEQ ID NO: 36) | YAYHRFT (SEQ ID NO: 37) | HQAYSTPYT (SEQ ID NO: 46) | GFTFSSYGMS (SEQ ID NO: 33) | VANIWQDGSTKYVDSVKG (SEQ ID NO: 34) | AYGNYWYIDR (SEQ ID NO: 35) |
| MH9 | KSSQSVGNDVA (SEQ ID NO: 74) | YASHRFT (SEQ ID NO: 45) | QQAYSSPYT (SEQ ID NO: 75) | GFTFSSYGMS (SEQ ID NO: 33) | VANIWQDGSEKYVDSVKG (SEQ ID NO: 41) | AYGNYWYIDR (SEQ ID NO: 35) |
| MH10 | KSSQSVTNDLA (SEQ ID NO: 76) | YASHRFT (SEQ ID NO: 45) | QQAYSTPYT (SEQ ID NO: 52) | GFTFSSYGMS (SEQ ID NO: 33) | VANIWQDGSEKYVDSVKG (SEQ ID NO: 41) | AYGNYWYIDR (SEQ ID NO: 35) |
| MH11 | KSSQSVGNDLA (SEQ ID NO: 77) | YAYHRFS (SEQ ID NO: 78) | QQAYSTPYT (SEQ ID NO: 52) | GFTFSSYGMS (SEQ ID NO: 33) | VANIWQDGSEKYVDSVKG (SEQ ID NO: 41) | AYGNYWYIDR (SEQ ID NO: 35) |
| MH12 | KSSQSVTNDVA (SEQ ID NO: 36) | YAYHRFT (SEQ ID NO: 37) | HQAYSTPYT (SEQ ID NO: 46) | GFTFSSYGMS (SEQ ID NO: 33) | VANIWQDGSEKYVDSVKG (SEQ ID NO: 41) | AYGNYWYIDR (SEQ ID NO: 35) |
| MH13 | KSSQSVTNDLA (SEQ ID NO: 76) | YAYHRFT (SEQ ID NO: 37) | HQAYSTPYT (SEQ ID NO: 46) | GFTFSSYGMS (SEQ ID NO: 33) | VANIWQDGSTKYVDSVKG (SEQ ID NO: 34) | AYGNYWYIDR (SEQ ID NO: 35) |
| MH14 | KSSQSVTNDLA (SEQ ID NO: 76) | YAYHRFS (SEQ ID NO: 78) | HQAYSTPYT (SEQ ID NO: 46) | GFTFSSYGMS (SEQ ID NO: 33) | VANIWQDGSTKYVDSVKG (SEQ ID NO: 34) | AYGNYWYIDR (SEQ ID NO: 35) |
| MH15 | KSSQSVTNDLA (SEQ ID NO: 76) | YASHRFS (SEQ ID NO: 79) | HQAYSTPYT (SEQ ID NO: 46) | GFTFSSYGMS (SEQ ID NO: 33) | VANIWQDGSTKYVDSVKG (SEQ ID NO: 34) | AYGNYWYIDR (SEQ ID NO: 35) |
| MH16 | KSSQSVTNDLA (SEQ ID NO: 76) | YAYHRFT (SEQ ID NO: 37) | HQAYSTPYT (SEQ ID NO: 46) | GFTFSSYGMS (SEQ ID NO: 33) | VANIWQDGSEKYVDSVKG (SEQ ID NO: 41) | AYGNYWYIDR (SEQ ID NO: 35) |
| MH17 | KSSQSVTNDLA (SEQ ID NO: 76) | YAYHRFS (SEQ ID NO: 78) | HQAYSTPYT (SEQ ID NO: 46) | GFTFSSYGMS (SEQ ID NO: 33) | VANIWQDGSEKYVDSVKG (SEQ ID NO: 41) | AYGNYWYIDR (SEQ ID NO: 35) |

TABLE 4-continued

CDR sequences of unique, library-derived and designer, PD1 antagonistic IgGs.

| Clone name | LCDR1 | LCDR2 | LCDR3 | HCDR1 | HCDR2 | HCDR3 |
|---|---|---|---|---|---|---|
| MH18 | KSSQSVTNDLA (SEQ ID NO: 76) | YASHRFS (SEQ ID NO: 79) | HQAYSTPYT (SEQ ID NO: 46) | GFTFSSYGMS (SEQ ID NO: 33) | VANIWQDGSEKYVDSVKG (SEQ ID NO: 41) | AYGNYWYIDR (SEQ ID NO: 35) |

TABLE 5

Predicted t cell epitope content scores for Hu317 and example lead clones.

| Clone Name | GE | HAF | LAF | TCED+ |
|---|---|---|---|---|
| Hu317 | 9 | 4 | 7 | 2 |
| 09C06 | 15 | 4 | 2 | 1 |
| 20C07 | 15 | 4 | 3 | 1 |
| 11C08 | 14 | 4 | 5 | 1 |
| 17A12 | 15 | 4 | 3 | 1 |
| MH4 | 15 | 4 | 3 | 1 |
| MH8 | 15 | 3 | 3 | 1 |
| MH12 | 15 | 3 | 3 | 1 |

TABLE 6

Charge isoform distributions for Hu317 and example lead clones.

| Clone Name | % Basic Isoforms | % Main Peak | % Acidic Isoforms |
|---|---|---|---|
| Hu317 | 23.1 | 68.9 | 8 |
| 09C06 | 3.5 | 82.8 | 13.7 |
| MH4 | 7 | 81.6 | 11.4 |
| MH8 | 6 | 77.4 | 16.6 |
| MH12 | 7.4 | 80.4 | 12.2 |

TABLE 7

Thermal transition midpoints for Hu317 and example lead clones.

| Clone | Tm1 °C. | Tm2 °C. | Tm3 °C. |
|---|---|---|---|
| Hu317 | 72.3 | 79.4* | 86.1 |
| 09C06 |  | 76.6* | 86.5 |
| MH4 |  | 75.3* | 86.2 |
| MH8 |  | 74.2* | 86.2 |
| MH12 | 71.9 |  | 86.5* |

*Fab Tm

TABLE 9

Examples of antibody variable region amino acid sequences.

Antibody MH8 heavy chain variable (VH) region
EVQLVESGGGLVQPGGSLRLSCAASGFTFSSYGMSVWRQAPGKGLEWVANI
WQDGSTKYVDSVKGRFTISRDNAKNSLYLQMNSLRAEDTAVYYCARAYGNY
WYIDRWGQGTTVTVSS (SEQ ID NO: 1)

Antibody MH8 light chain variable (VL) region
DIVMTQSPDSLAVSLGERATINCKSSQSVTNDVAWYQQKPGQPPKLLINYA
YHRFTGVPDRFSGSGYGTDFTLTISSLQAEDVAVYYCHQAYSTPYTFGQGT
KLEIK (SEQ ID NO: 2)

Antibody MH4 heavy chain variable (VH) region
EVQLVESGGGLVQPGGSLRLSCAASGFSLSSYGMSWVRQAPGKGLEWVAVI
WQDGSTNYVDSVKGRFTISRDNAKNSLYLQMNSLRAEDTAVYYCARAYGNY
WYIDRWGQGTTVTVSS (SEQ ID NO: 3)

Antibody MH4 light chain variable (VL) region
DIVMTQSPDSLAVSLGERATINCKSSQSVTNDVAWYQQKPGQPPKLLINYA
YHRFTGVPDRFSGSGYGTDFTLTISSLQAEDVAVYYCHQAYSTPYTFGQGT
KLEIK (SEQ ID NO: 4)

Antibody MH12 heavy chain variable (VH) region
EVQLVESGGGLVQPGGSLRLSCAASGFTFSSYGMSWVRQAPGKGLEWVANI
WQDGSEKYVDSVKGRFTISRDNAKNSLYLQMNSLRAEDTAVYYCARAYGNY
WYIDRWGQGTTVTVSS (SEQ ID NO: 5)

Antibody MH12 light chain variable (VL) region
DIVMTQSPDSLAVSLGERATINCKSSQSVTNDVAWYQQKPGQPPKLLINYA
YHRFTGVPDRFSGSGYGTDFTLTISSLQAEDVAVYYCHQAYSTPYTFGQGT
KLEIK (SEQ ID NO: 6)

Antibody 09C06 heavy chain variable (VH) region
EVQLVESGGGLVQPGGSLRLSCAASGFSFSSYGMHWVRQAPGKGLEWVANI
WQDGSTNYVDSVKGRFTISRDNAKNSLYLQMNSLRAEDTAVYYCARAYGNY
WYIDRWGQGTTVTVSS (SEQ ID NO: 7)

Antibody 09C06 light chain variable (VL) region
DIVMTQSPDSLAVSLGERATINCKSSQSVSNDVAWYQQKPGQPPKLLINYA
SHRFTGVPDRFSGSGYGTDFTLTISSLQAEDVAVYYCHQAYSTPYTFGQGT
KLEIK (SEQ ID NO: 8)

TABLE 8

IgGs shown high integrity before and after forced oxidation with 0.5% H2O2, measured by Size Exclusion (SEC), Reverse Phase (RP) and Hydrophobic Interaction (HIC) Chromatographies

| Clone | % HMW by SEC | | Retention RP (mins) | | Retention Heavy (mins) | | Retention Light (mins) | | Retention HIC (Mins) | |
|---|---|---|---|---|---|---|---|---|---|---|
| | 0 mins H2O2 | 120 min H2O2 | 0 mins H2O2 | 120 min H2O2 | 0 mins H2O2 | 120 min H2O2 | 0 mins H2O2 | 120 min H2O2 | 0 mins H2O2 | 120 min H2O2 |
| Hu317 | 0.13 | 0.17 | 8.3 | 8.2 | 7.7 | 7.7 | 6.5 | 6.5 | 7.2 | 6.9 |
| 09C06 | 0.27 | 0.27 | 12.8 | 12.7 | 11.7 | 11.6 | 8.6 | 8.6 | 6.3 | 5.7 |
| MH4 | 0.28 | 0.41 | 13.7 | 13.7 | 12.8 | 12.5 | 8.9 | 8.8 | 7.2 | 6.8 |
| MS8 | 0.3 | 0.25 | 13.2 | 13.1 | 12 | 11.9 | 8.8 | 8.8 | 6.9 | 6.5 |
| MH12 | 0.52 | 0.31 | 13.2 | 13.2 | 12 | 12 | 8.9 | 8.8 | 7 | 6.9 |

TABLE 10

Examples of antibody Fc region amino acid sequences.

Human IgG4 wild type
ASTKGPSVFPLAPCSRSTSESTAALGCLVKDYFPEPVTVSWNSGALTSGVH
TFPAVLQSSGLYSLSSVVTVPSSSLGTKTYTCNVDHKPSNTKVDKRVESKY
GPPCPSCPAPEFLGGPSVFLFPPKPKDTLMISRTPEVTCVVVDVSQEDPEV
QFNWYVDGVEVHNAKTKPREEQFNSTYRVVSVLTVLHQDWLNGKEYKCKVS
NKGLPSSIEKTISKAKGQPREPQVYTLPPSQEEMTKNQVSLTCLVKGFYPS
DIAVEWESNGQPENNYKTTPPVLDSDGSFFLYSRLTVDKSRWQEGNVFSCS
VMHEALHNHYTQKSLSLSLGK (SEQ ID NO: 9)

Human IgG4(S228P)
ASTKGPSVFPLAPCSRSTSESTAALGCLVKDYFPEPVTVSWNSGALTSGVH
TFPAVLQSSGLYSLSSVVTVPSSSLGTKTYTCNVDHKPSNTKVDKRVESKY
GPPCPPCPAPEFLGGPSVFLFPPKPKDTLMISRTPEVTCVVVDVSQEDPEV
QFNWYVDGVEVHNAKTKPREEQFNSTYRVVSVLTVLHQDWLNGKEYKCKVS
NKGLPSSIEKTISKAKGQPREPQVYTLPPSQEEMTKNQVSLTCLVKGFYPS
DIAVEWESNGQPENNYKTTPPVLDSDGSFFLYSRLTVDKSRWQEGNVFSCS
VMHEALHNHYTQKSLSLSLGK (SEQ ID NO: 10)

Human IgG1 wild type
ASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPKS
CDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKC
KVSNKALPAPIEKTISKAKGQPREPQVYTLPPS<u>RDELT</u>KNQVSLTCLVKGF
YPSDIAVEWESNGQPENNYKTTPPVLDSDGSFFLYSKLTVDKSRWQQGNVF
SCSVMHEALHNHYTQKSLSLSPGK (SEQ ID NO: 11)

Human IgG1-3M
ASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPKS
CDKTHTCPPCPAPEAAGAPSVFLFPPKPKDTLMISRTPEVTCVVVDVSHED
PEVKFNWYVDGVEVHNAKTKPREEQYNSTYRVVSVLTVLHQDWLNGKEYKC
KVSNKALPAPIEKTISKAKGQPREPQVYTLPPS<u>RDELT</u>KNQVSLTCLVKGF
YPSDIAVEWESNGQPENNYKTTPPVLDSDGSFFLYSKLTVDKSRWQQGNVF
SCSVMHEALHNHYTQKSLSLSPGK (SEQ ID NO: 12)

Human IgG2 wild type
ASTKGPSVFPLAPCSRSTSESTAALGCLVKDYFPEPVTVSWNSGALTSGVH
TFPAVLQSSGLYSLSSVVTVPSSNFGTQTYTCNVDHKPSNTKVDKTVERKC
CVECPPCPAPPVAGPSVFLFPPKPKDTLMISRTPEVTCVVVDVSHEDPEVQ
FNWYVDGVEVHNAKTKPREEQFNSTFRVVSVLTVVHQDWLNGKEYKCKVSN
KGLPAPIEKTISKTKGQPREPQVYTLPPSREEMTKNQVSLTCLVKGFYPSD
ISVEWESNGQPENNYKTTPPMLDSDGSFFLYSKLTVDKSRWQQGNVFSCSV
MHEALHNHYTQKSLSLSPGK (SEQ ID NO: 13)

Human IgG1 wild type "REEM" allotype
ASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPKS
CDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKC
KVSNKALPAPIEKTISKAKGQPREPQVYTLPPS<u>REEM</u>KNQVSLTCLVKGF
YPSDIAVEWESNGQPENNYKTTPPVLDSDGSFFLYSKLTVDKSRWQQGNVF
SCSVMHEALHNHYTQKSLSLSPGK (SEQ ID NO: 14)

Human IgG1-3M "REEM" allotype
ASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPKS
CDKTHTCPPCPAPEAAGAPSVFLFPPKPKDTLMISRTPEVTCVVVDVSHED
PEVKFNWYVDGVEVHNAKTKPREEQYNSTYRVVSVLTVLHQDWLNGKEYKC
KVSNKALPAPIEKTISKAKGQPREPQVYTLPPS<u>REEM</u>KNQVSLTCLVKGFY
PSDIAVEWESNGQPENNYKTTPPVLDSDGSFFLYSKLTVDKSRWQQGNVFS
CSVMHEALHNHYTQKSLSLSPGK (SEQ ID NO: 15)

TABLE 11

Examples of target protein amino acid sequences.

Human PD1 sequence
MQIPQAPWPVVWAVLQLGWRPGWFLDSPDRPWNPPTFSPALLVVTEGDNAT
FTCSFSNTSESFVLNWYRMSPSNQTDKLAAFPEDRSQPGQDCRFRVTQLPN
GRDFHMSVVRARRNDSGTYLCGAISLAPKAQIKESLRAELRVTERRAEVPT
AHPSPSPRPAGQFQTLVVGVVGGLLGSLVLLVWVLAVICSRAARGTIGARR
TGQPLKEDPSAVPVFSVDYGELDFQWREKTPEPPVPCVPEQTEYATIVFPS
GMGTSSPARRGSADGPRSAQPLRPEDGHCSWPL (SEQ ID NO: 16)

Cynomolgus monkey PD1 sequence
MQIPQAPWPVVWAVLQLGWRPGWFLESPDRPWNAPTFSPALLLVTEGDNAT
FTCSFSNASESFVLNWYRMSPSNQTDKLAAFPEDRSQPGQDCRFRVTRLPN
GRDFHMSVVRARRNDSGTYLCGAISLAPKAQIKESLRAELRVTERRAEVPT
AHPSPSPRPAGQFQALVVGVVGGLLGSLVLLVWVLAVICSRAAQGTIEARR
TGQPLKEDPSAVPVFSVDYGELDFQWREKTPEPPAPCVPEQTEYATIVFPS
GLGTSSPARRGSADGPRSPRPLRPEDGHCSWPL (SEQ ID NO: 17)

Human LSAMP sequence
MVRRVQPDRKQLPLVLLRLLCLLPTGLPVRSVDFNRGTDNITVRQGDTAIL
RCVVEDKNSKVAWLNRSGIIFAGHDKWSLDPRVELEKRHSLEYSLRIQKVD
VYDEGSYTCSVQTQHEPKTSQVYLIVQVPPKISNISSDVTVNEGSNVTLVC
MANGRPEPVITWRHLTPTGREFEGEEEYLEILGITREQSGKYECKAANEVS
SADVKQVKVTVNYPPTITESKSNEATTGRQASLKCEASAVPAPDFEWYRDD
TRINSANGLEIKSTEGQSSLTVTNVTEEHYGNYTCVAANKLGVTNASLVLF
RPGSVRGINGSISLAVPLWLLAASLLCLLSKC (SEQ ID NO: 415)

Human BTN2A1 sequence
MESAAALHFSRPASLLLLLSLCALVSAQFIVVGPTDPILATVGENTTLRC
HLSPEKNAEDMEVRWFRSQFSPAVFVYKGGRERTEEQMEEYRGRTTFVSKD
ISRGSVALVIHNITAQENGTYRCYFQEGRSYDEAILHLVVAGLGSKPLISM
RGHEDGGIRLECISRGWYPKPLTVWRDPYGGVAPALKEVSMPDADGLFMVT
TAVIIRDKSVRNMSCSINNTLLGQKKESVIFIPESFMPSVSPCAVALPIIV
VILMIPIAVCIYWINKLQEKKILSGEKEFERETREIALKELEKERVQKEE
ELQVKEKLQEELRWRRTFLHAVDVVLDPDTAHPDLFLSEDRRSVRRCPFRH
LGESVPDNPERFDSQPCVLGRESFASGKHYWEVEVENVIEWTVGVCRDSVE
RKGEVLLIPQNGFWTLEMHKGQYRAVSSPDRILPLKESLCRVGVFLDYEAG
DVSFYNMRDRSHIYTCPRSAFSVPVRPFFRLGCEDSPIFICPALTGANGVT
VPEEGLTLHRVGTHQSL (SEQ ID NO: 416)

TABLE 12

Target proteins identified via IgG screening of proteome arrays

| IgG clone | Number of hits in chip screen | PD1 (PDCD1) NM_005018 | BTN2A1 NM_007049 | LSAMP BC033803 |
|---|---|---|---|---|
| MH4 (2 μg/ml) | 2 | strong | | weak |
| MH8 (2 ug/ml) | 2 | strong | | weak |
| MH12 (2 ug/ml) | 3 | strong | weak/med | weak |
| Hu317 (2 ug/ml) | 1 | strong | | |
| Anti-fluorescein (4-4-20e) Human IgG4 kappa. Ab00102-13.0 negative control (2 ug/ml) | 0 | | | |
| PBS (secondary only) | 0 | | | |

TABLE 13

Fold fluorescence changes in IgG binding on non-target protein-transfected cells versus mock (ZSgreen only) cells

| IgG clone | BTN2A1 | LSAMP | CD20 |
|---|---|---|---|
| Hu317 | 1.2 | 1.5 | 1.4 |
| MH4 | 1.2 | 1.9 | 1.1 |
| MH8 | 1.1 | 7.1 | 0.9 |
| MH12 | 1.3 | 4.1 | 1.1 |
| Secondary only | 1.1 | 1.5 | 0.9 |

The invention claimed is:

1. An anti-PD1 antibody or an antigen-binding portion thereof, wherein the antibody or antigen-binding portion thereof comprises a heavy chain variable (VH) region and a light chain variable (VL) region, wherein (a) the VH region amino acid sequence comprises HCDR1 of GFTFSSYGMS (SEQ ID NO:33), HCDR2 of VANIWQDGSTKYVDSVKG (SEQ ID NO:34), and HCDR3 of AYGNYWYIDR (SEQ ID NO:35); and the VL region amino acid sequence comprises LCDR1 of KSSQSVTNDVA (SEQ ID NO:36), LCDR2 of YAYHRFT (SEQ ID NO:37), and LCDR3 of HQAY-STPYT (SEQ ID NO:46); or (b) the VH region amino acid sequence comprises HCDR1 of GFSLSSYGMS (SEQ ID NO:39), HCDR2 of VAVIWQDGSTNYVDSVKG (SEQ ID NO:40), and HCDR3 of AYGNYWYIDR (SEQ ID NO:35); and the VL region amino acid sequence comprises LCDR1 of KSSQSVTNDVA (SEQ ID NO:36), LCDR2 of YAYHRFT (SEQ ID NO:37), and LCDR3 of HQAY-STPYT (SEQ ID NO:46).

2. The antibody or antigen-binding portion of claim 1, wherein
(a) the VH region amino acid sequence comprises SEQ ID NO:1 and the VL region amino acid sequence comprises SEQ ID NO:2; or
(b) the VH region amino acid sequence comprises SEQ ID NO:3 and the VL region amino acid sequence comprises SEQ ID NO:4.

3. The antibody or antigen-binding portion of claim 1, wherein the antibody is humanized or chimeric.

4. The antibody or antigen-binding portion of claim 1, wherein the VH region, the VL region, or both the VH and the VL region comprise one or more human framework region amino acid sequences.

5. The antibody or antigen-binding portion of claim 1, wherein the VH region, the VL region, or both the VH and the VL region comprise a human variable region framework scaffold amino acid sequence into which the CDRs have been inserted.

6. The antibody or antigen-binding portion of claim 1, wherein the VH region comprises an IGHV3-7 human germline scaffold amino acid sequence into which the HCDR1, HCDR2 and HCDR3 amino acid sequences have been inserted.

7. The antibody or antigen-binding portion of claim 1, wherein the VL region comprises an IGKV4-1 human germline scaffold amino acid sequence into which the LCDR1, LCDR2 and LCDR3 amino acid sequences have been inserted.

8. The antibody or antigen-binding portion of claim 1, wherein the antibody comprises an immunoglobulin constant region.

9. The antibody or antigen-binding portion of claim 8, wherein the immunoglobulin constant region is IgG, IgE, IgM, IgD, IgA or IgY.

10. The antibody or antigen-binding portion of claim 9, wherein the immunoglobulin constant region is IgG1, IgG2, IgG3, IgG4, IgA1 or IgA2.

11. The antibody or antigen-binding portion of claim 8, wherein the immunoglobulin constant region is immunologically inert.

12. The antibody or antigen-binding portion of claim 11, wherein the immunoglobulin constant region comprises any one of SEQ ID NOS:9-15.

13. The antibody or antigen-binding portion of claim 8, wherein the immunoglobulin constant region is a wild-type human IgG4 constant region, a human IgG4 constant region comprising the amino acid substitution S228P, a wild-type human IgG1 constant region, a human IgG1 constant region comprising the amino acid substitutions L234A, L235A and G237A or a wild-type human IgG2 constant region wherein numbering is according to the EU index as in Kabat.

14. The antigen-binding portion of claim 1, wherein the antibody or antigen-binding portion is an Fab, an Fab', an F(ab')$_2$, an Fv, an scFv, a maxibody, a minibody, an intrabody, a diabody, a triabody, a tetrabody, or a bis-scFv.

15. The antibody or antigen-binding portion of claim 1, wherein the antibody is monoclonal.

16. The antibody or antigen-binding portion of claim 1, wherein the antibody or antigen-binding portion binds specifically to (a) human PD1 or (b) human PD1 and cynomolgus PD1.

17. An immunoconjugate comprising the antibody or antigen-binding portion of claim 1 linked to a therapeutic agent.

18. The immunoconjugate of claim 17, wherein the therapeutic agent is a cytotoxin, a radioisotope, a chemotherapeutic agent, an immunomodulatory agent, an anti-angiogenic agent, an antiproliferative agent, a pro-apoptotic agent, a cytostatic enzyme, a cytolytic enzymes, a therapeutic nucleic acid, an anti-angiogenic agent, an anti-proliferative agent, or a pro-apoptotic agent.

19. A pharmaceutical composition comprising the immunoconjugate of claim 17 and a pharmaceutically acceptable carrier, diluent or excipient.

20. A pharmaceutical composition comprising the antibody or antigen-binding portion claim 1 and a pharmaceutically acceptable carrier, diluent or excipient.

* * * * *